US006794126B2

(12) United States Patent
Troy

(10) Patent No.: US 6,794,126 B2
(45) Date of Patent: Sep. 21, 2004

(54) METHODS FOR PREVENTING OR INHIBITING NEURONAL CELL DEATH

(75) Inventor: Carol M. Troy, Hastings-on-Hudson, NY (US)

(73) Assignee: The Trustees of Columbia University in the City of New York, New York, NY (US)

(*) Notice: Subject to any disclaimer, the term of this patent is extended or adjusted under 35 U.S.C. 154(b) by 0 days.

(21) Appl. No.: 09/150,623

(22) Filed: Sep. 4, 1998

(65) Prior Publication Data

US 2002/0044931 A1 Apr. 18, 2002

Related U.S. Application Data

(63) Continuation of application No. PCT/US97/04158, filed on Mar. 4, 1997, which is a continuation-in-part of application No. 08/610,220, filed on Mar. 4, 1996, now Pat. No. 6,635,738.

(51) Int. Cl.$^7$ .......................... C12Q 1/00; G01N 33/53; G01N 33/567

(52) U.S. Cl. ............................ 435/4; 435/7.2; 435/7.21

(58) Field of Search ........................ 424/133.1; 435/7.2, 435/4, 7.21

(56) References Cited

U.S. PATENT DOCUMENTS

| 5,672,500 A | 9/1997 | Litwack et al. |
| 5,856,169 A | * 1/1999 | Litwack et al. |

FOREIGN PATENT DOCUMENTS

| EP | 425212 | 4/1999 |
| EP | 533350 | 5/1999 |

OTHER PUBLICATIONS

Jackowski (British Journal of Neurosurgery vol. 9 pp 303–317), 1995.*
Lazas et al (Molecullar & Cellular Biology vol. 8 (3) pp 1247–1252), Mar. 1988.*
Burgess et al (Journal of Cell Biology vol. 111, pp 2129–2138), Nov. 1990.*
Salgaller et al (Cancer Immunol. Immunother. vol. 39 pp. 105–116), 1994.*
Barinaga, M. (1994) Cell Suicide: By ICE, Not Fire. *Science* 263:754–756.
Casciola–Rosen, L.A. et al. (1994) Specific Cleavage of the 70–kDa Protein Component of the U1 Small Nuclear Ribonucleoprotein Is a Characteristic Biochemical Feature of Apoptotic Cell Death. *J. Bio. Chem.* 269(49):30757–30760.
Duggan, M.E. et al. (1995) Non–Peptide Fibrinogen Receptor Antagonists. 7. Design and Synthesis of a Potent, Orally Active Fibrinogen Receptor Antagonist. *J. of Med. Chem.* 38(17):3332–3341.

Enari, M., Hug, H. and Nagata, S. (1995) Involvement of an Ice–like protease in Fas–mediated apoptosis *Nature* 375:78–81.
Fernandes–Alnemri, T., Litwack, G. and Alnemri, E. S. (1995) Mch2, a New Member of the Apoptotic Ced–3/Ice Cysteine Protease Gene Family. *Cancer Res.* 55:2737–2742.
Koivunen, E., Gay, D.A. and Ruoslahti, E. (1993) Selection of Peptides Binding to the $\alpha_5\beta_1$ Integrin from Phage Display Library. *J. of Biol. Chem.* 27:20205–20210.
Los, M. et al. (1995) Requirement of an ICE/CED–3 protease for Fas/APO–1–mediated apoptosis. *Nature* 375:81–83.
Luo, A.–M. et al. (Nov. 1993) Antigen Mimicry in Autoimmune Disease, Sharing of Amino Acid Residues Critical for Pathogenic T Cell Activation. *Am. Soc. for Clin. Invest.* 92:2117–2123.
Mashima, T. et al. (1995) Aspartate–Based Inhibitor of Interleukin–1β–Converting Enzyme Prevents Antitumor Agent–Induced Apoptosis in Human Myeloid Leukemia U937 Cells. *Biochem. and Biophys. Res. Comm.* 209(3):907–915.
Milligan, C.E. et al. (1995) Peptide Inhibitors of the ICE Protease Family Arrest Programmed Cell Death of Motoneurons In Vivo and In Vitro. *Neuron* 15:385–393.
Munday, N.A. et al. (1995) Molecular Cloning and Pro–apoptotic Activity of ICE $_{rel}$ II and ICE $_{rel}$ III, Members of the ICE/CED–3 Family of Cysteine Proteases. *J. of Biol. Chem.* 270(26):15870–15876.
Wang, L. et al. (1994) Ich–1, an Ice/ced–3–Related Gene, Encodes Both Positive and Negative Regulators of Programmed Cell Death. *Cell* 78:739–750.
Wa ng, X. et al. (1995) Purification of an Interleukin–1β Converting Enzyme–related Cysteine Protease That Cleaves Sterol Regulatory Element–binding Proteins between the Leucine Zipper and Transmembrane Domains. *J. of Biol. Chem.* 270(30):18044–18055.
Xuan, J.–W. et al. (1995) Site–Directed Mutagenesis of the Arginine–Glycine–Aspartic Acid Sequence in Osteopontin Destroys Cell Adhesion and Migration Functions. *J. of Cell Biochem.* 57:680–690.
Derossi, D., et al. (1996) Cell Internalization of the third helix of *Antennapedia* homeodomain is receptor–independent. *J. Biol. Chem.* 271, 18188–93 (Exhibit 1).

(List continued on next page.)

*Primary Examiner*—Mark Navarro
(74) *Attorney, Agent, or Firm*—John P. White; Cooper & Dunham LLP

(57) ABSTRACT

The present invention provides for a compound having the structure: $(AA_1)_n$-Cys-$(AA_2)_m$ wherein n=0, 1, 2, 3, 4 or 5 and m=0, 1, 2, 3, 4 or 5, provided the sum of (n+m) is greater than or equal to two and less than or equal to five, if n=1, $(AA_1)_n$=Ala-, if n=2, $(AA_1)_n$=Gln-Ala-, if n≧3, $(AA_1)_n$= $(Xaa)_p$-Gln-Ala-, and Xaa=any amino acid and wherein if n=3, p=1, if n=4, p=2, if n=5, p=3, if m=1, $(AA_2)_m$=-Arg, if m=2, $(AA_2)_m$=-Arg-Gly, if m≧3, $(AA_2)_m$=-Arg-Gly-$(Xaa)_q$, wherein if m=3, q=1, if m=4, q=2, if m=5, q=3. The present invention provides for a method of inhibiting cell death and a method for alleviating symptoms of a neurodegenerative disorder in a subject.

6 Claims, 29 Drawing Sheets

OTHER PUBLICATIONS

Prochiantz, A. (1996) Getting hydrophilic compounds into cells: lessions from homeopeptides. Curr. Opin. Neurobiol. 6:629–34 (Exhibit 2).

Troy, C. M., et al. (1996) Downregulation of Cu/Zn superoxide dismutase leads to cell death via the nitric oxide–peroxynitrite pathway. J. Neurosci. 16:253–61 (Exhibit 3).

* cited by examiner

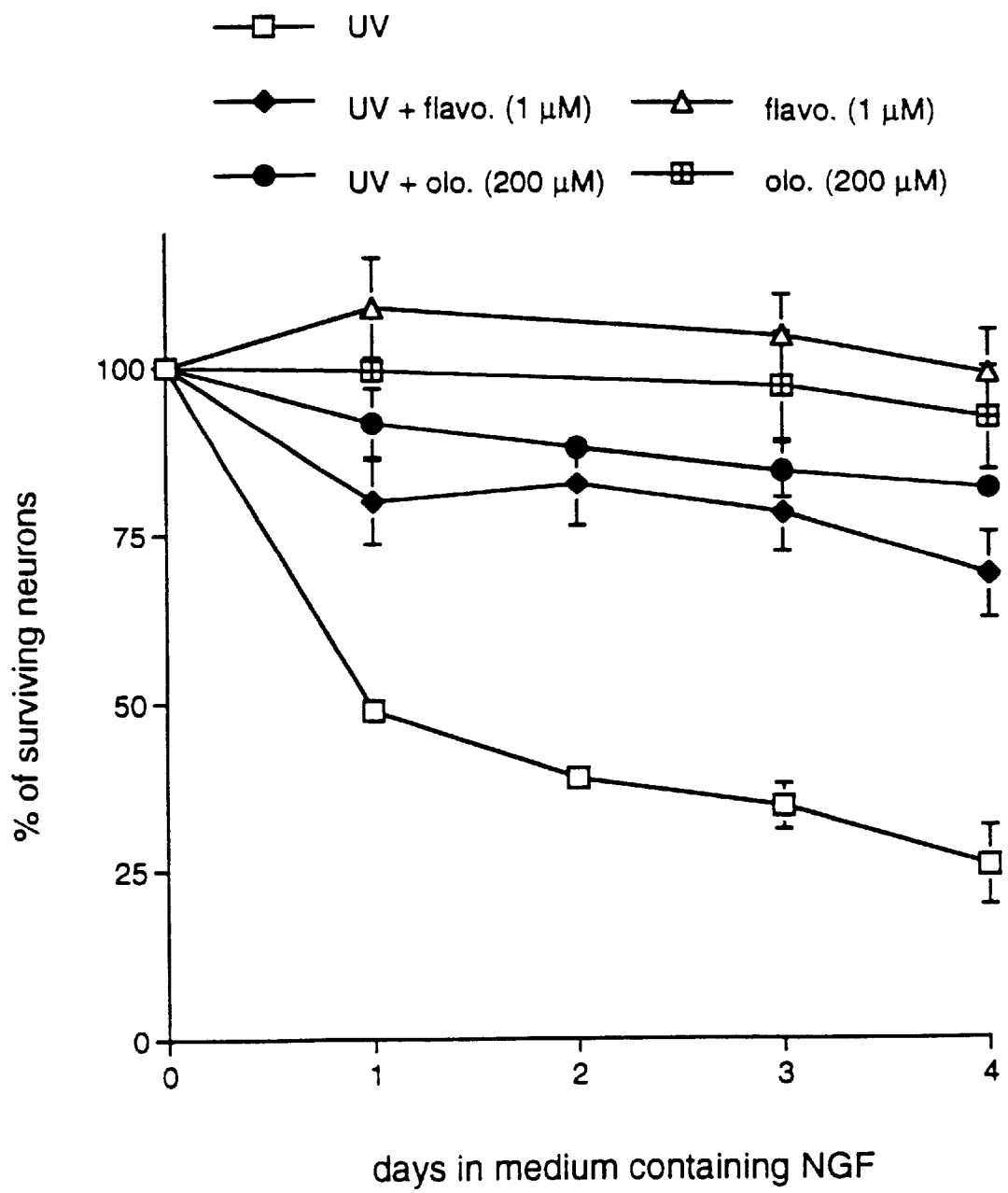

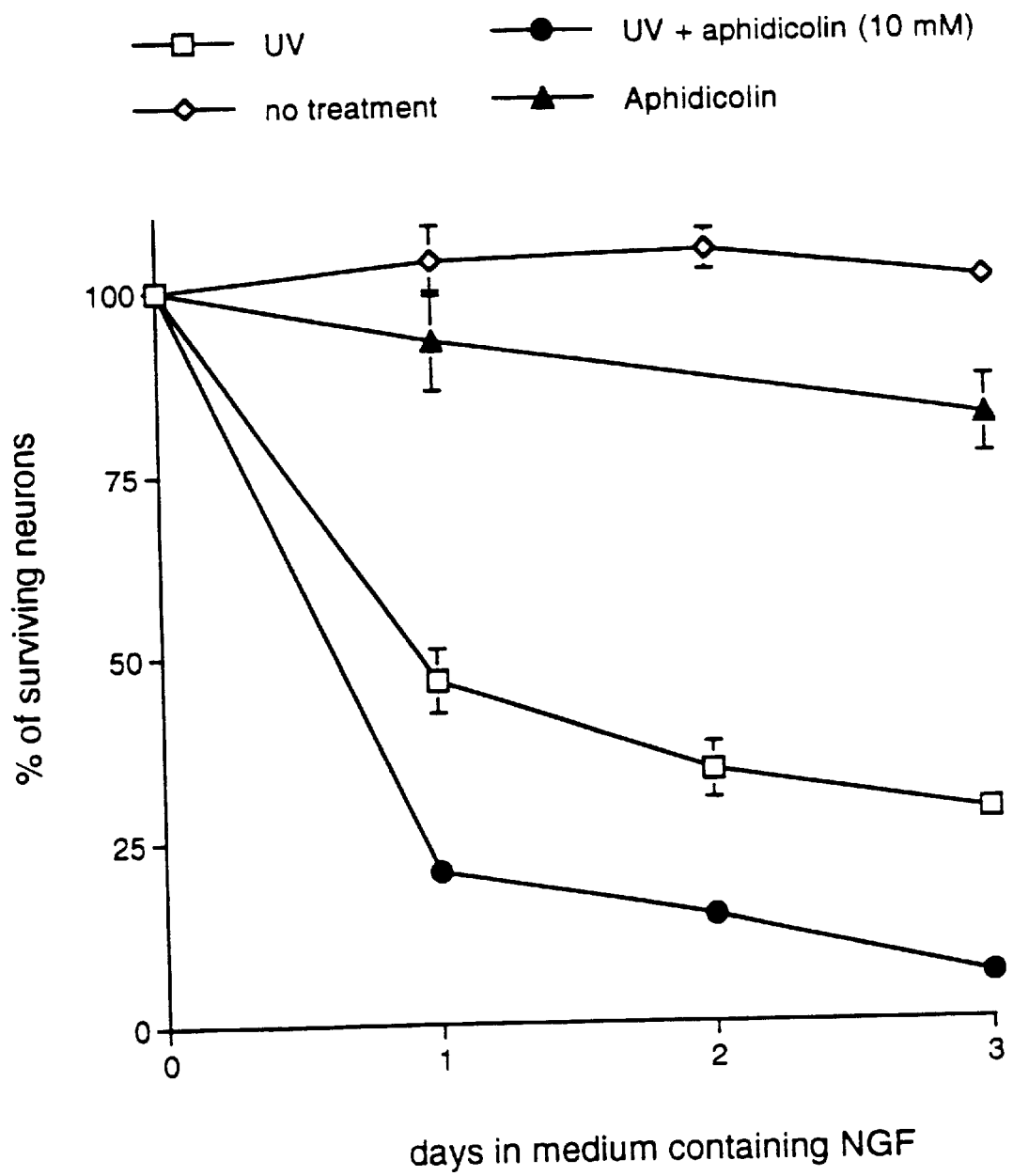

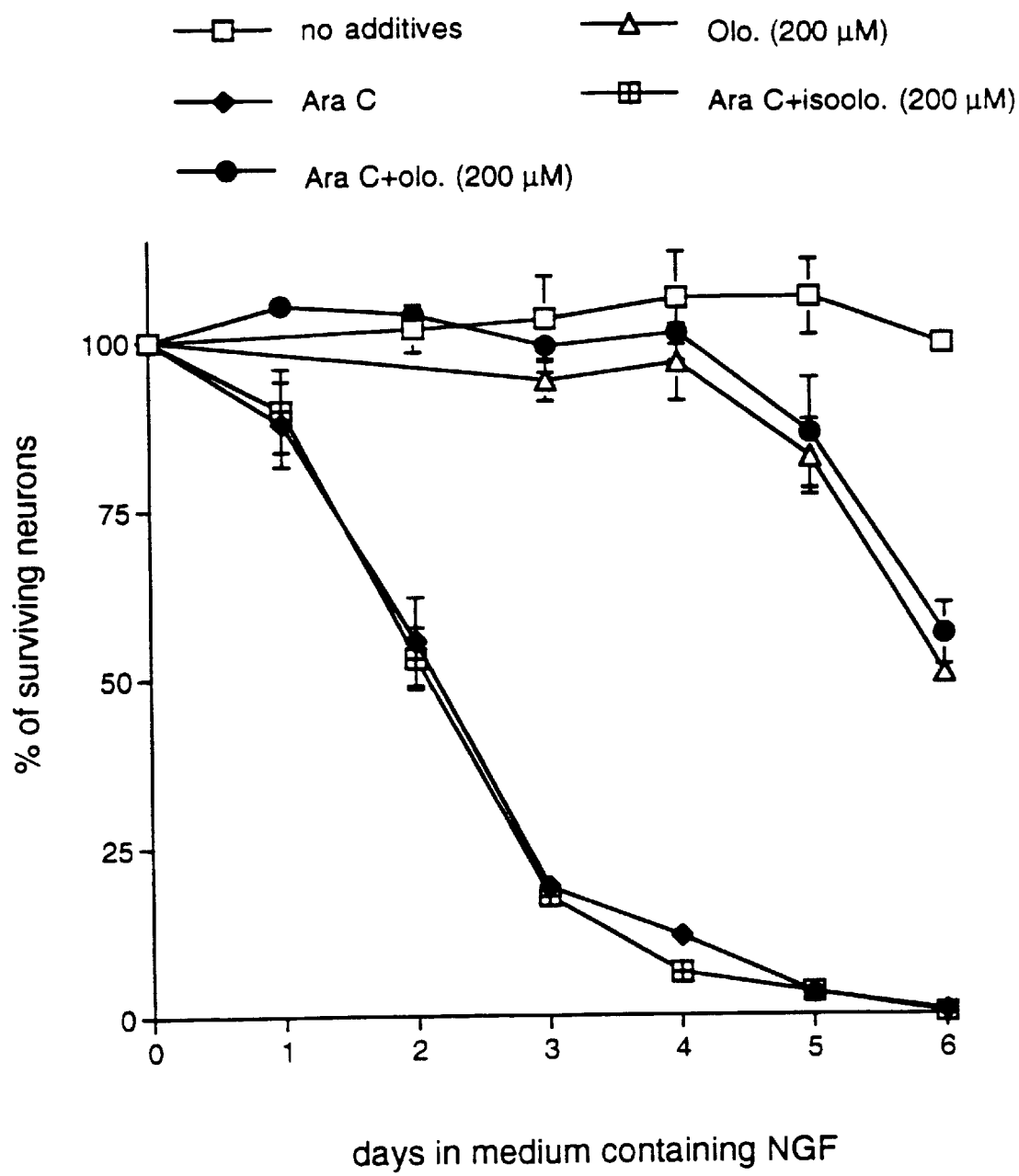

FIGURE 9A
FIGURE 9B
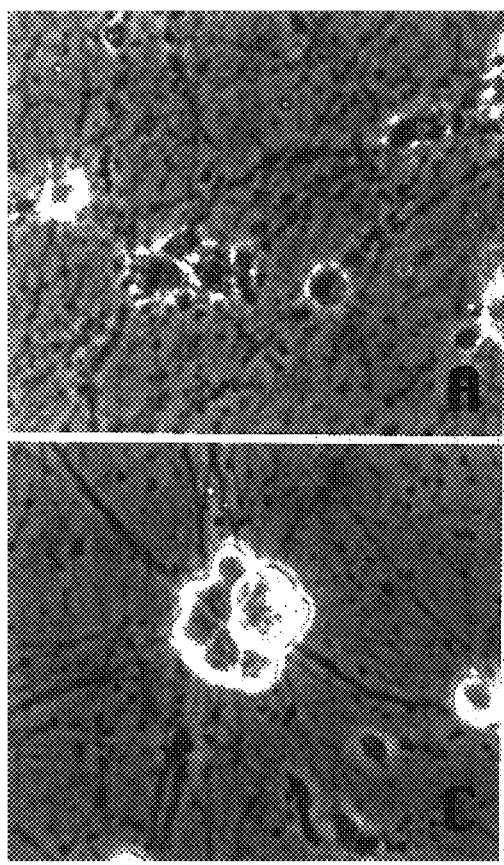
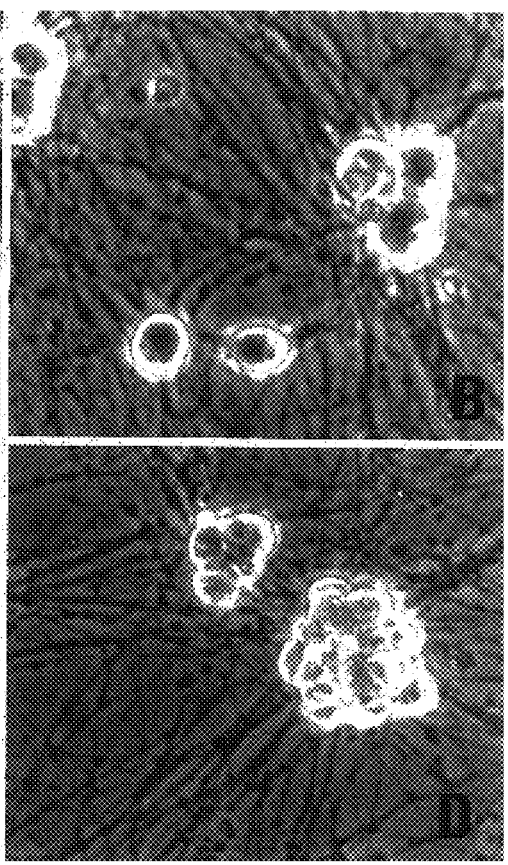
FIGURE 9C
FIGURE 9D

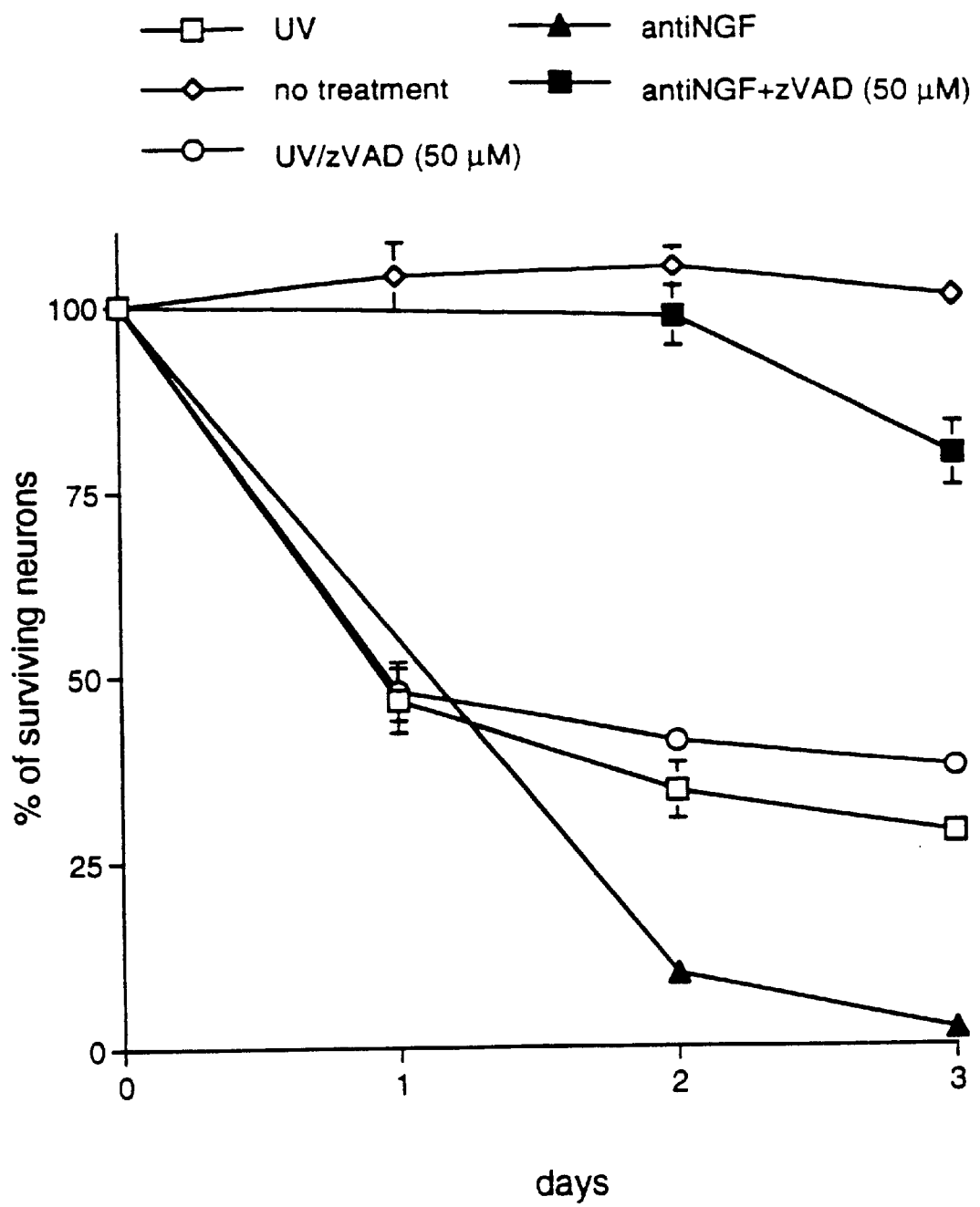

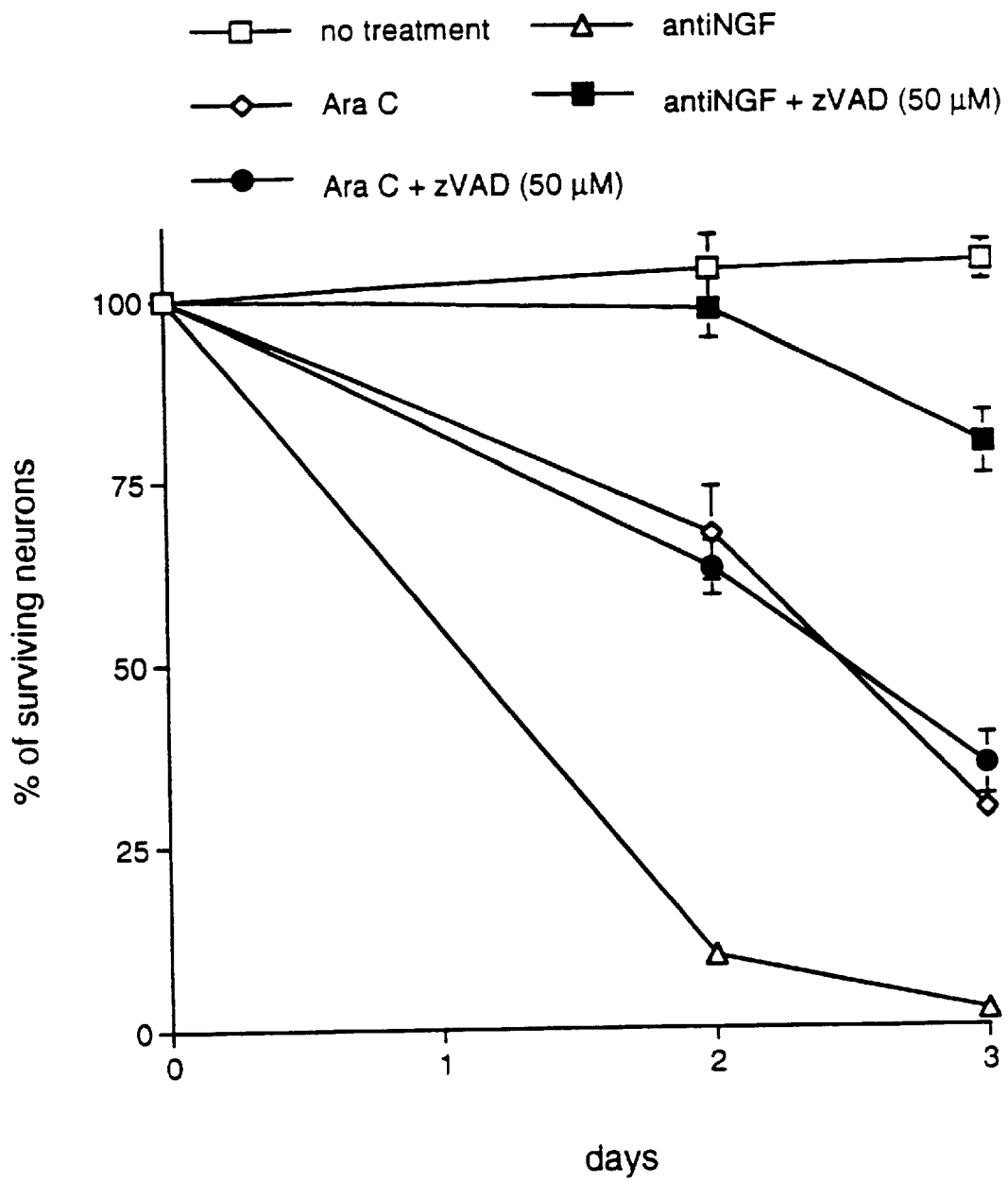

```
                       SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
         (A) LENGTH: 6 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:1:

Ile Gln Ala Cys Arg Gly
1               5

(2) INFORMATION FOR SEQ ID NO:2:

(i) SEQUENCE CHARACTERISTICS:
         (A) LENGTH: 4 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:2:

Glx Val Ala Asp
1

(2) INFORMATION FOR SEQ ID NO:3:

(i) SEQUENCE CHARACTERISTICS:
         (A) LENGTH: 5 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:3:

Gln Ala Cys Arg Gly
1               5

(2) INFORMATION FOR SEQ ID NO:4:

(i) SEQUENCE CHARACTERISTICS:
         (A) LENGTH: 6 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:4:
```

```
Gly Arg Cys Ala Gln Ile
1               5
```

(2) INFORMATION FOR SEQ ID NO:5:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

```
Ile Cys Gly Arg Ala Gln Ala
1               5
```

(2) INFORMATION FOR SEQ ID NO:6:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

```
Glx Tyr Val Ala Asp
1               5
```

(2) INFORMATION FOR SEQ ID NO:7:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

```
Tyr Val Ala Asp
1
```

(2) INFORMATION FOR SEQ ID NO:8:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

```
Asp Val Glu Asp
1
```

(2) INFORMATION FOR SEQ ID NO:9:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

-continued

```
Arg Gln Ile Lys Ile Trp Phe Gln Asn Arg Arg Met Lys Trp Lys Lys
1               5                   10                  15
```

(2) INFORMATION FOR SEQ ID NO:10:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

```
Arg Gln Ile Lys Ile Trp Phe Gln Asn Arg Arg Met Lys Trp Lys Lys
1               5                   10                  15

Ile Gln Ala Cys Arg Gly
            20
```

(2) INFORMATION FOR SEQ ID NO:11:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

```
Arg Gln Ile Lys Ile Trp Phe Gln Asn Arg Arg Met Lys Trp Lys Lys
1               5                   10                  15

Gln Ala Cys Arg Gly
        20
```

METHODS FOR PREVENTING OR INHIBITING NEURONAL CELL DEATH

This application is a continuation application of PCT International Application No. PCT/US97/04158, International Filing Date Mar. 4, 1997, which is a continuation-in-part application of U.S. Ser. No. 08/610,220, filed Mar. 4, 1996, now U.S. Pat. No. 6,635,738, the contents of which are hereby incorporated by reference into the present application.

The invention disclosed herein was made with Government support under NIH Grants No. MDA CU 50898501A1, NS 15076R35-AG10963, NS33689, NS25168, PO1-AG07232, RR00645 and P50-AG-08702 from the Department of Health and Human Services. Accordingly, the U.S. Government has certain rights in this invention.

BACKGROUND OF THE INVENTION

Throughout this application, various publications are referenced by author and date. Full citations for these publications may be found listed alphabetically at the end of the specification immediately preceding the Sequence Listing. The disclosures of these publications in their entireties are hereby incorporated by reference into this application in order to more fully describe the state of the art as known to those skilled therein as of the date of the invention described and claimed herein.

Members of the family of cysteine proteases related to the interleukin 1β converting enzyme (ICE) have been shown to be necessary for programmed cell death in a number of biological systems (Yuan et al., 1993). For example, mutations of the ICE homologue, ced3, inhibit cell death which normally occurs during development in *C. elegans* (Hengartner et al., 1992) and overexpression of ICE or the ICE-like proteases NEDD-2/ICH-1 and Yama/apopain/CPP32 induces apoptosis in primary neurons, rat fibroblasts and insect cells (Gagliardini et al., 1994; Miura et al., 1994; Wang et al., 1994; Kumar et al., 1994; and Fernandes-Alnemri et al., 1994). Mice lacking ICE are resistant to apoptosis induced by Fas antibody. In the mammary gland, ICE mRNA is expressed during involution, when apoptosis occurs in this tissue. The pox virus product crmA, a serpin-like pseudosubstrate for ICE, protects sensory neurons and fibroblasts from trophic factor withdrawal-induced death (Gagliardini et al., 1994 and Miura et al., 1994), while Fas/APO-1 mediated apoptosis is blocked by the inhibitory peptide YVAD (Seq. I.D. No. 7), as well as crmA (Tewari and Dixit, 1995; Enari et al., 1995; Los et al., 1995; and Tewari et al., 1995). Normal motor neuron loss in development is also blocked by YVAD (Seq. I.D. No. 7), a pseudosubstrate which mimics the pro-IL-1β cleavage site and thus inhibits ICE-like proteases (Milligan et al., 1995). While ICE cleaves pro-IL-1β to produce IL-1β, the role of IL-1β itself in apoptosis is unresolved and it has been suggested that other substrates may be critical in cell death (Lazebnik et al., 1994; Tewari et al., 1995; and Nicholson et al., 1995).

Although many researchers have focused their efforts on the identification and isolation of an inhibitor of the family of cysteine proteases related to the ICE enzyme, there has been little success in this area. Many of these research strategies involve searching through a multitude of compounds and agents which are extrinsic to the ICE protein normally. However, the present invention deviates from the established search strategies and provides for the surprising discovery that use of a piece of the ICE enzyme itself successfully inhibits ICE and thus prevents neuronal cell death.

SUMMARY OF THE INVENTION

This invention provides for a compound having the structure: $(AA_1)_n\text{-Cys-}(AA_2)_m$, wherein n=0, 1, 2, 3, 4 or 5 and m=0, 1, 2, 3, 4 or 5, provided the sum of (n+m) is greater than or equal to two and less than or equal to five, if n=1, $(AA_1)_n$=Ala-, if n=2, $(AA_1)_n$=Gln-Ala-, if n≧3, $(AA_1)_n$=$(Xaa)_p$-Gln-Ala-, and Xaa=any amino acid and wherein if n=3, p=1, if n=4, p=2, if n=5, p=3, if m=1, $(AA_2)_m$=-Arg, if m=2, $(AA_2)_m$=-Arg-Gly, if m≧3, $(AA_2)_m$=-Arg-Gly-$(Xaa)_q$ wherein if m=3, q=1, if m=4, q=2, if m=5, q=3. The present invention provides for a method of inhibiting cell death and a method for alleviating symptoms of a neurodegenerative disorder in a subject.

Legend: a=+NGF (control cells); b=−NGF+V-ICE$_{inh}$ (2 additions); c=−NGF+V-ICE$_{inh}$ (1 addition); d=−NGF. Data in all cases are presented as means ±SEM (n=3–5).

FIGS. 3A, 3B, 3C and 3D. V-ICE$_{inh}$ protects cultured sympathetic neurons from apoptotic death induced by NGF-withdrawal. (A) Time course of protection of sympathetic neurons by V-ICE$_{inh}$ (50 nM). (B–D) Photomicrographs of sympathetic neurons: (B) NGF; (C) anti-NGF; (D) anti-NGF+V-ICE$_{inh}$ (50 nM). Sympathetic neuron cultures were prepared from 2 day old rat pups. On the sixth day following plating, NGF was removed by washing the cultures three times with RPMI 1640 medium plus 10% horse serum, followed by the addition of medium containing anti-mouse NGF (1:200). V-ICE$_{inh}$ (50 nM) was added to certain cultures as indicated. Numbers of surviving neurons were assessed by counting the number of intact, phase bright neurons in each well by strip counting. This determination was made on the initial day of NGF deprivation and then on subsequent days. Results are expressed as the percentage of neurons present relative to that present immediately following NGF withdrawal.

Figure 4A:
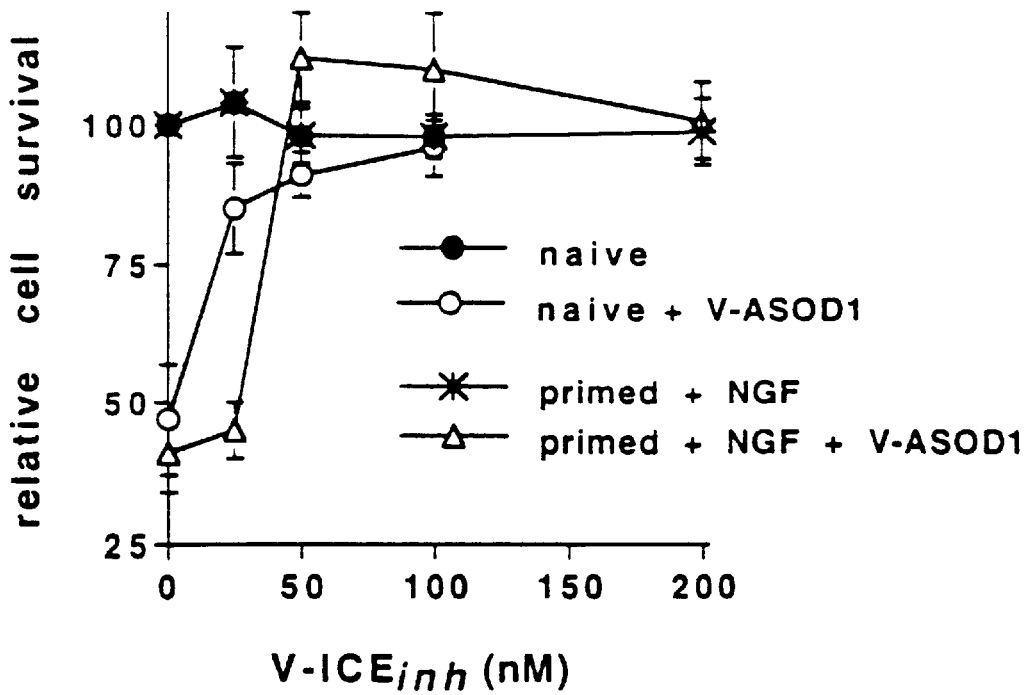
Figure 4B:
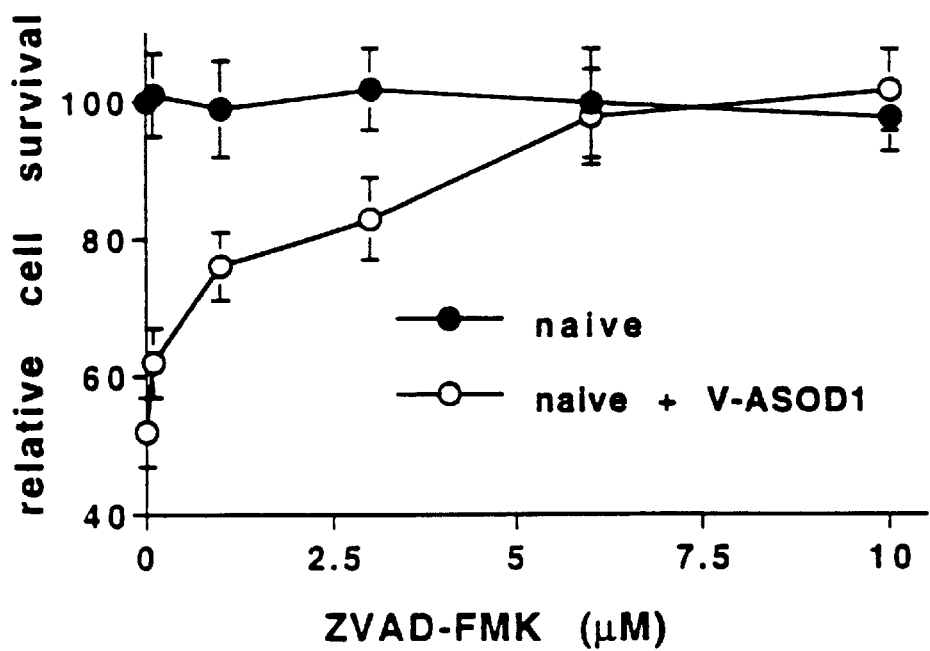

FIGS. 4A and 4B. V-ICE inh protects PC12 cells from death induced by down-regulation of SOD1. (A) Naive PC12 cells were washed and plated in RPMI 1640 medium with 10% horse serum and 5% fetal calf serum and incubated with or without V-ASOD1 (vector linked antisense oligonucleotide to superoxide dismutase) (50 nM) and the indicated concentrations of V-ICE$_{inh}$. Primed PC12 cells (PC12 cells treated with NGF for more than 7 days) were washed and replated in RPMI 1640 medium supplemented with 1% horse serum and NGF (100 ng/ml), and incubated with or without V-ASOD1 (50 nM) and the indicated concentrations of V-ICE$_{inh}$. Quantification of surviving cells was at one day. (B) ZVAD-FMK (Seq. I.D. No. 2) protects PC12 cells from V-ASOD1 induced death. Naive PC12 cells were treated as in FIG. 4A, incubated with V-ASOD1 (50 nM) together with the indicated concentrations of ZVAD-FMK (Seq. I.D. No. 2) and quantified at one day for proportion of surviving cells.

FIGS. 5A, 5B, 5C and 5D. Blockade of IL-1β protects from neurotrophin-deprivation induced and from SOD1 down-regulation-induced death. (A) IL-1β antibody protects from SOD1 down-regulation but not from trophic deprivation. For V-ASOD1 experiments, PC12 cells were replated as described in FIG. 4, with and without IL-1β antibody. For trophic deprivation, PC12 cells were extensively washed and plated as described in FIG. 2 in serum-free RPMI, with and without the IL-1β antibody. Quantification of surviving cells was at one day. V-ASOD1 treated cells had 47% survival, control cells received serum. Serum deprived cells had 48% survival, control cells received NGF. Data are reported as the percentage increase in surviving cells. (B) IL-1ra protects PC12 cells from SOD1 down-regulation completely and from trophic deprivation partially. PC12 cells were plated as described in FIG. 5A, with and without IL-1ra. Quantification of surviving cells was at one day. V-ASOD1-treated cells had 47% survival, serum-deprived cells had 26% survival. Data are reported as the percentage increase in surviving cells. (C) IL-1β levels are increased by NGF treatment or by V-ASOD1 treatment. PC12 cells were plated as described in FIGS. 2 and 4, with and without V-ICE$_{inh}$ (200 μM for trophic deprivation, 25 nM for V-ASOD1 treatment). After 20 hours, media was removed and IL-1β measured by ELISA. Surviving cells were quantified at 20 hrs. (D) IL-1β potentiates V-ASOD1 induced death. PC12 cells were plated as described in FIG. 4, with the indicated additives: IL-1β at 1 μg/ml, V-ASOD1 at 50 nM, and V-ICE$_{inh}$ at 25 nM.

FIGS. 6A, 6B, 6C, 6D and 6E. The CDK inhibitors, flavopiridol and olomoucine, inhibit the UV-irradiation-induced death of rat sympathetic neurons. Primary cultures of neonatal rat superior cervical ganglion neurons were grown in the presence of NGF for three days prior to UV exposure as indicated. Neurons were pretreated with the indicated drugs for 16 hours prior to UV irradiation. Each data point is the mean +/−SEM (n=3) and is expressed relative to the number of neurons present in each culture at the time of drug treatment. (FIG. 6A) Effects of flavopiridol (1 mM) and olomoucine (200 μM) on the time course of survival of sympathetic neurons exposed to UV irradiation. (FIG. 6B) Effects of various doses of flavopiridol on the survival of UV-treated sympathetic neurons at day 1. (FIG. 6C) Effects of various doses of olomoucine on the survival of UV-treated sympathetic neurons at day 1. (FIG. 6D) Effect of isoolomoucine (200 μM) on the time course of survival of sympathetic neurons exposed to UV irradiation. (FIG. 6E) Effect of aphidicolin (10 μM) on the time course of survival of sympathetic neurons exposed to UV irradiation.

FIGS. 7A, 7B, 7C and 7D. Phase contrast micrographs of primary sympathetic neurons maintained in medium containing NGF and treated with the following: (FIG. 7A) UV (FIG. 7B) no treatment; (FIG. 7C) UV+1 μM flavopiridol; (FIG. 7D) UV+200 μM olomoucine. Pictures are of cells at one day post-UV exposure.

FIGS. 8A, 8B, 8C, 8D and 8E. The CDK inhibitors, flavopiridol and olomoucine, inhibit AraC-induced death of rat sympathetic neurons. Primary cultures of neonatal rat superior cervical ganglion neurons were grown in the presence of NGF for three days prior to drug treatment. Replicate cultures were treated with AraC (100 μM) as indicated. Each data point is the mean +/−SEM (n=3) and is expressed relative to the number of neurons present in each culture at the time of drug treatment. (FIG. 8A) Effect of flavopiridol (1 mM) on the time course of survival of sympathetic neurons treated with AraC. (FIG. 8B) Effect of various doses of flavopiridol on the survival of AraC-treated sympathetic neurons at day 3. (FIG. 8C) Effects of olomoucine (200 mM) and isolomoucine (200 μM) on the time course of survival of sympathetic neurons treated with AraC. (FIG. 8D) Effect of various doses of olomoucine on the survival of AraC-treated sympathetic neurons at day 3. (FIG. 8E) Effect of aphidicolin (10 μM) on the time course of survival of sympathetic neurons treated with AraC.

FIGS. 9A, 9B, 9C and 9D. Phase contrast micrographs of primary sympathetic neurons maintained in medium containing NGF and treated with the following: (FIG. 9A) AraC; 100 μM (FIG. 9B) no treatment; (FIG. 9C) AraC+1 μM flavopiridol; (FIG. 9D) AraC+200 μM olomoucine. Pictures are of cells at three days after AraC treatment.

Figure 10:
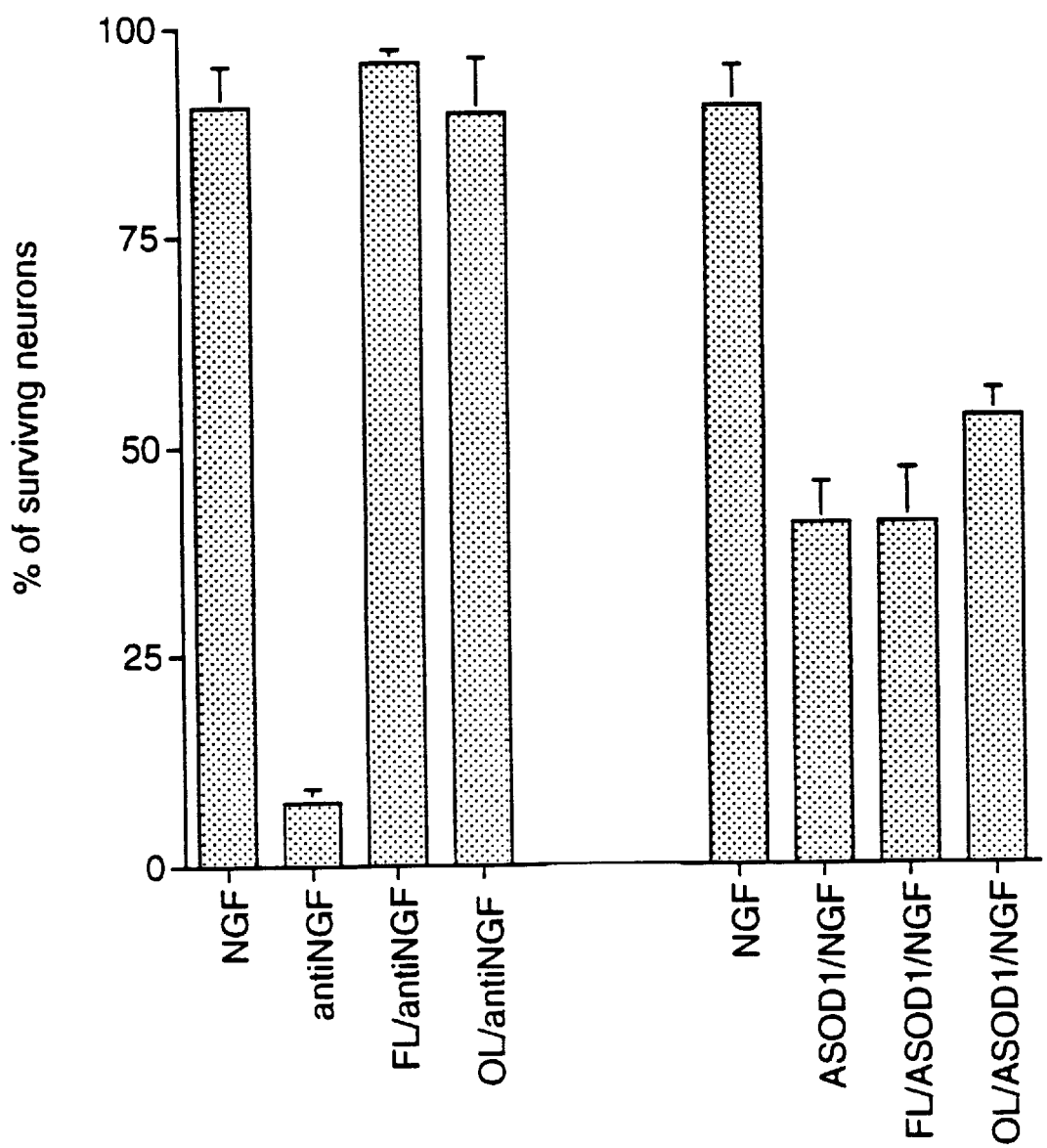

FIG. 10. The CDK inhibitors, flavopiridol (FL) and olomoucine (OL), do not inhibit death of sympathetic neurons depleted of SOD1. Primary cultures of neonatal rat superior cervical ganglion neurons were grown in the presence of NGF for three days prior to drug treatment. Replicate cultures were deprived of NGF (antiNGF) or treated with ASOD1 (50 nM) along with SNAP (100 μM) as indicated. Each data point is the mean +/−SEM (n=3) and is expressed relative to the number of neurons present in each culture at the time of drug treatment.

Figure 11C:
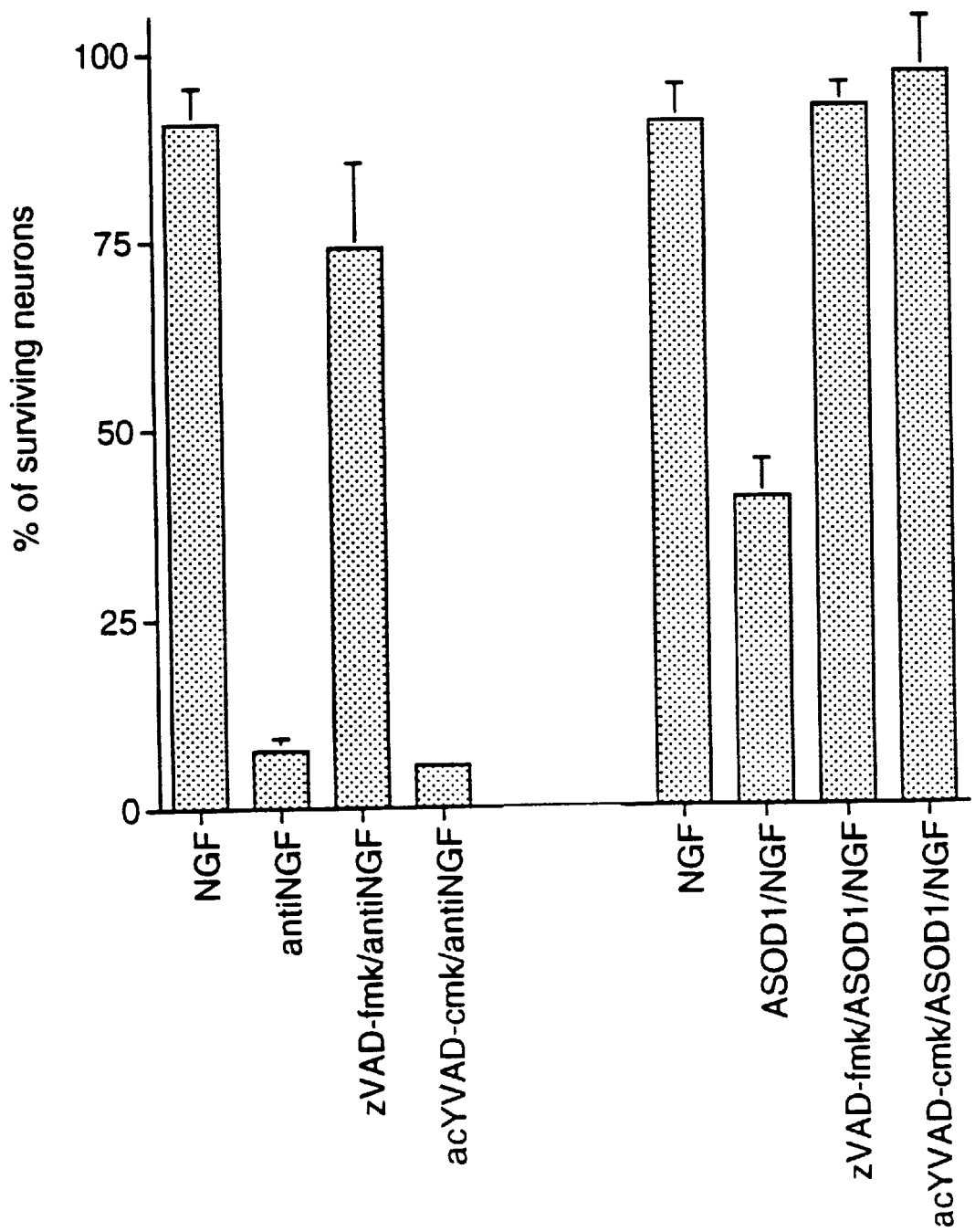

FIGS. 11A, 11B and 11C. The cysteine aspartase family protease inhibitors zVAD-fmk and acYVAD-cmk differentially promote survival of sympathetic neurons exposed to DNA damaging agents, deprived of NGF or depleted of SOD1. Primary cultures of neonatal rat superior cervical ganglion neurons were grown in the presence of NGF for three days prior to experimentation. Cultures were deprived of NGF and treated as indicated for three days before assessment of neuronal survival. Neurons exposed to UV irradiation were pretreated with zVAD-fmk for 16 hr. (FIG. 11A) Effect of zVAD-fmk (50 μM) on the time course of survival of sympathetic neurons exposed to UV irradiation and deprived of NGF. (FIG. 11B) Effect of zVAD-fmk (50 μM) on the time course of survival of sympathetic neurons treated with AraC (100 μM) and deprived of NGF. (FIG. 11C) Effect of acYVAD-fmk (250 μM) and zVAD-fmk (50 μM) on the survival of neurons deprived of NGF (antiNGF) or treated with antisense to SOD1 (ASOD1) along with SNAP (100 μM). Survival was measured two days after NGF deprivation or treatment with ASOD1/SNAP. Each data point is the mean +/−SEM (n=3) and is expressed relative to the number of neurons present in each well at the time of drug treatment.

Figure 12A:
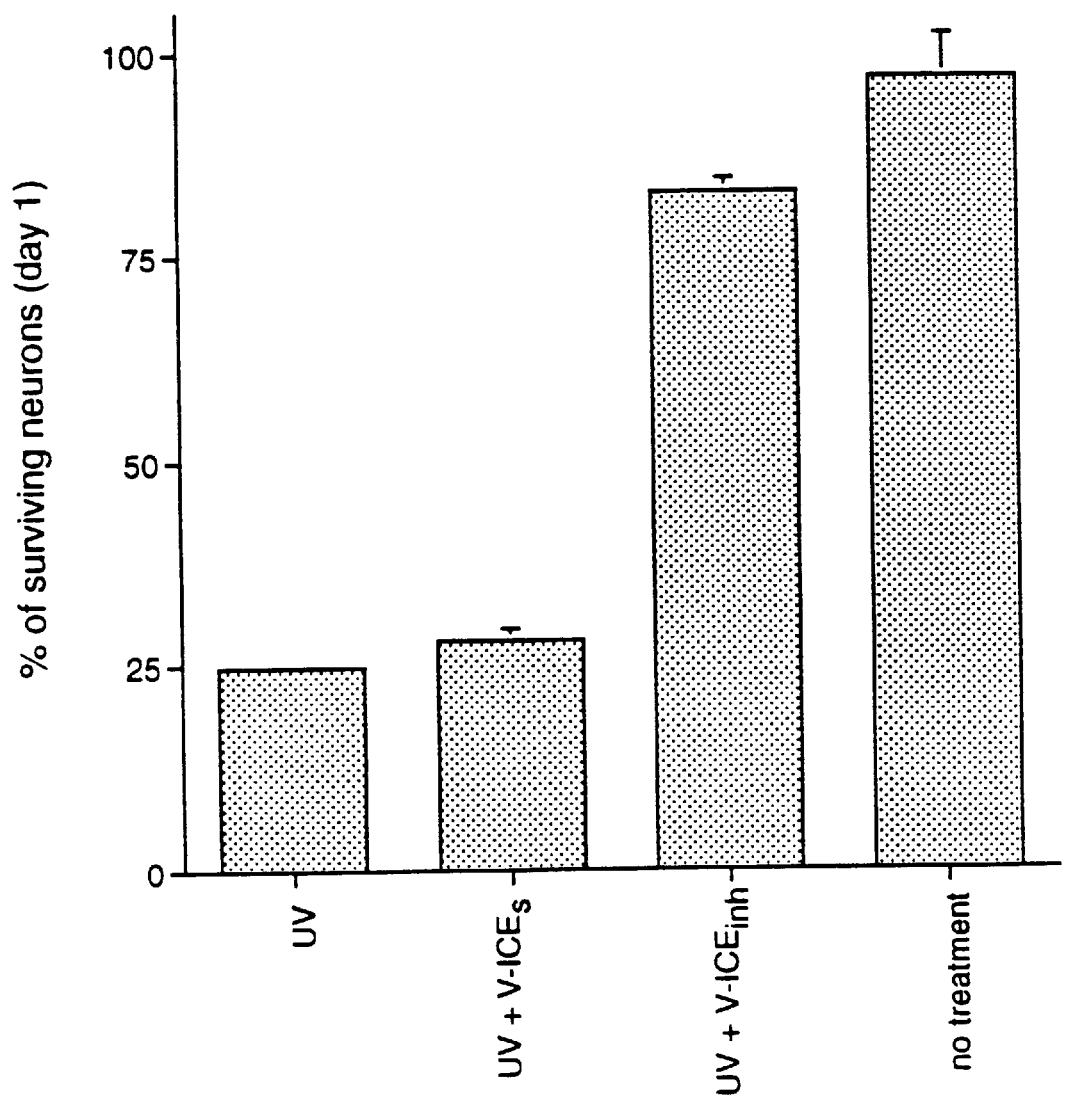
Figure 12B:
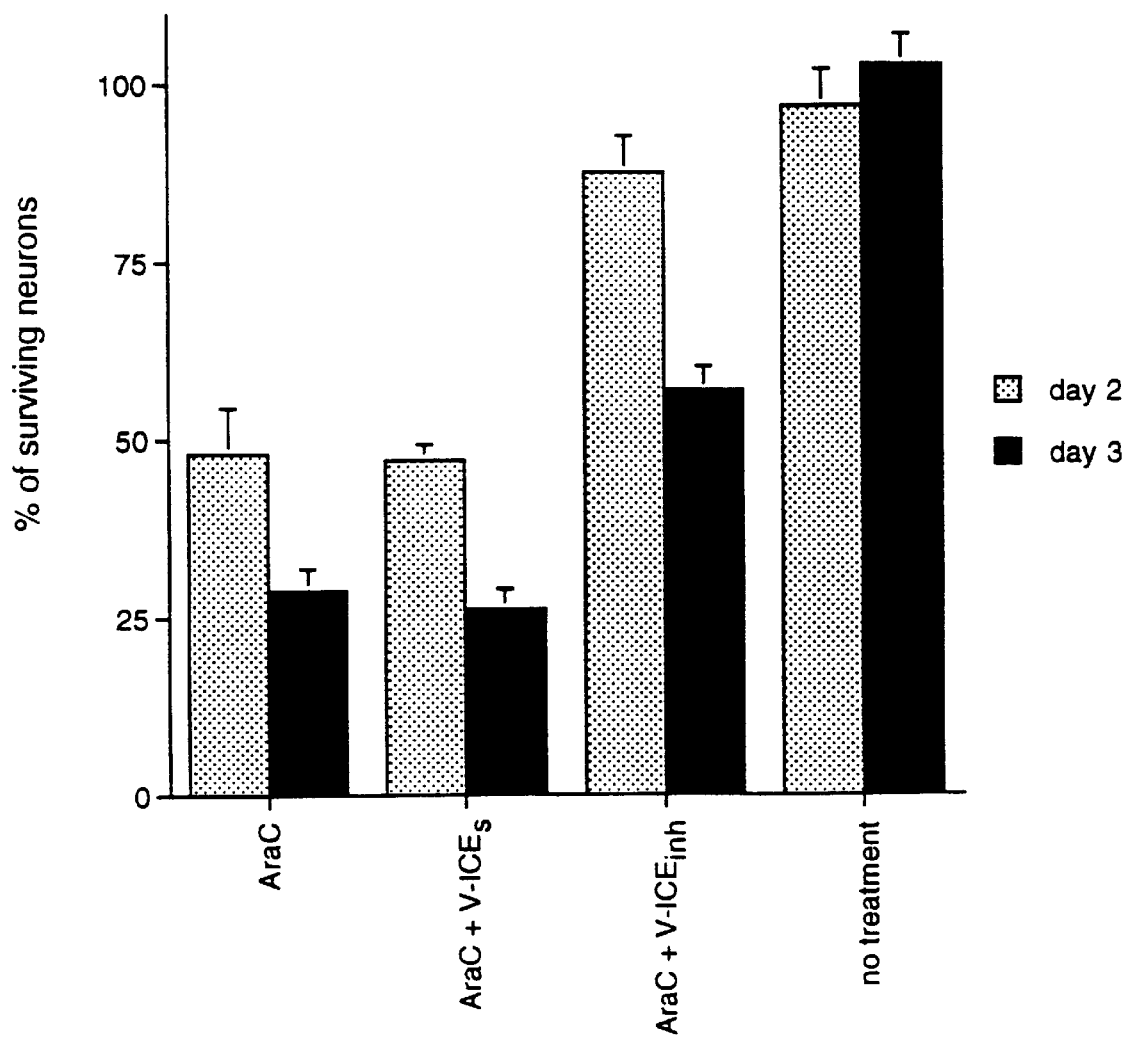
Figure 12C:
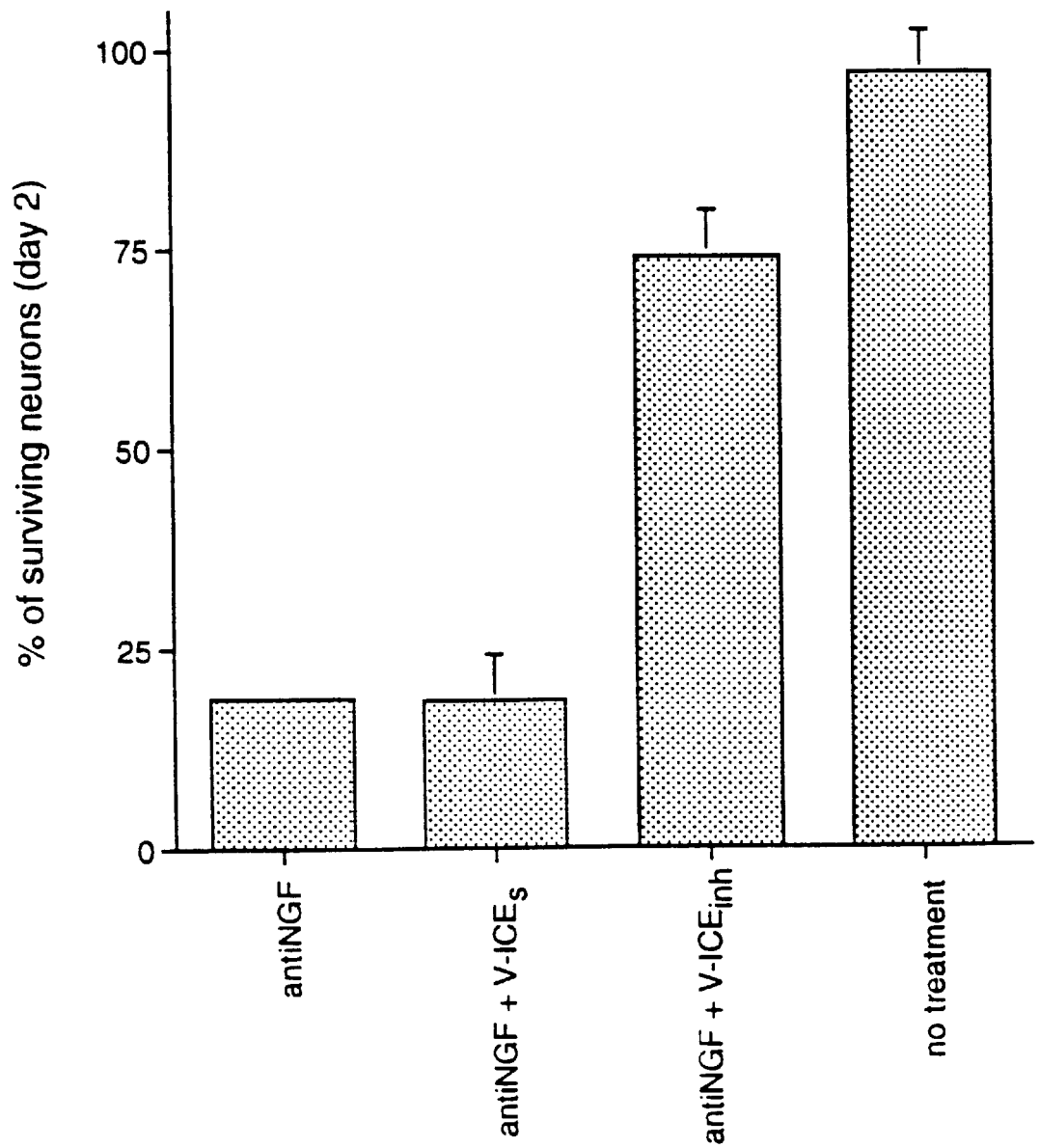

FIGS. 12A, 12B and 12C. The general cysteine aspartase family protease inhibitor V-ICE$_{inh}$ protects sympathetic neurons from NGF deprivation and UV- and AraC-induced apoptosis. Primary cultures of neonatal rat superior cervical ganglion neurons were grown in the presence of NGF for three days prior to experimentation. On the third day, neurons were pretreated 18 hr in the presence of NGF with the V-ICE$_{inh}$ inhibitor (200 nM) or the V-ICEs control (200 nM) as indicated. Neurons were then exposed to UV irradiation, AraC (100 μM) or deprived of NGF. (FIG. 12A) Effect of V-ICE$_{inh}$ inhibitor (200 nM) on the time course of survival of sympathetic neurons exposed to UV irradiation. (FIG. 12B) Effect of V-ICE$_{inh}$ inhibitor (200 nM) on the time course of survival of sympathetic neurons exposed to AraC. (FIG. 12C) Effect of V-ICE inh inhibitor (200 nM) on the time course of survival of sympathetic neurons deprived of NGF. Each data point is the mean +/−SEM (n=3) and is expressed relative to the number of neurons present in each well at the time of drug treatment.

Figure 13:
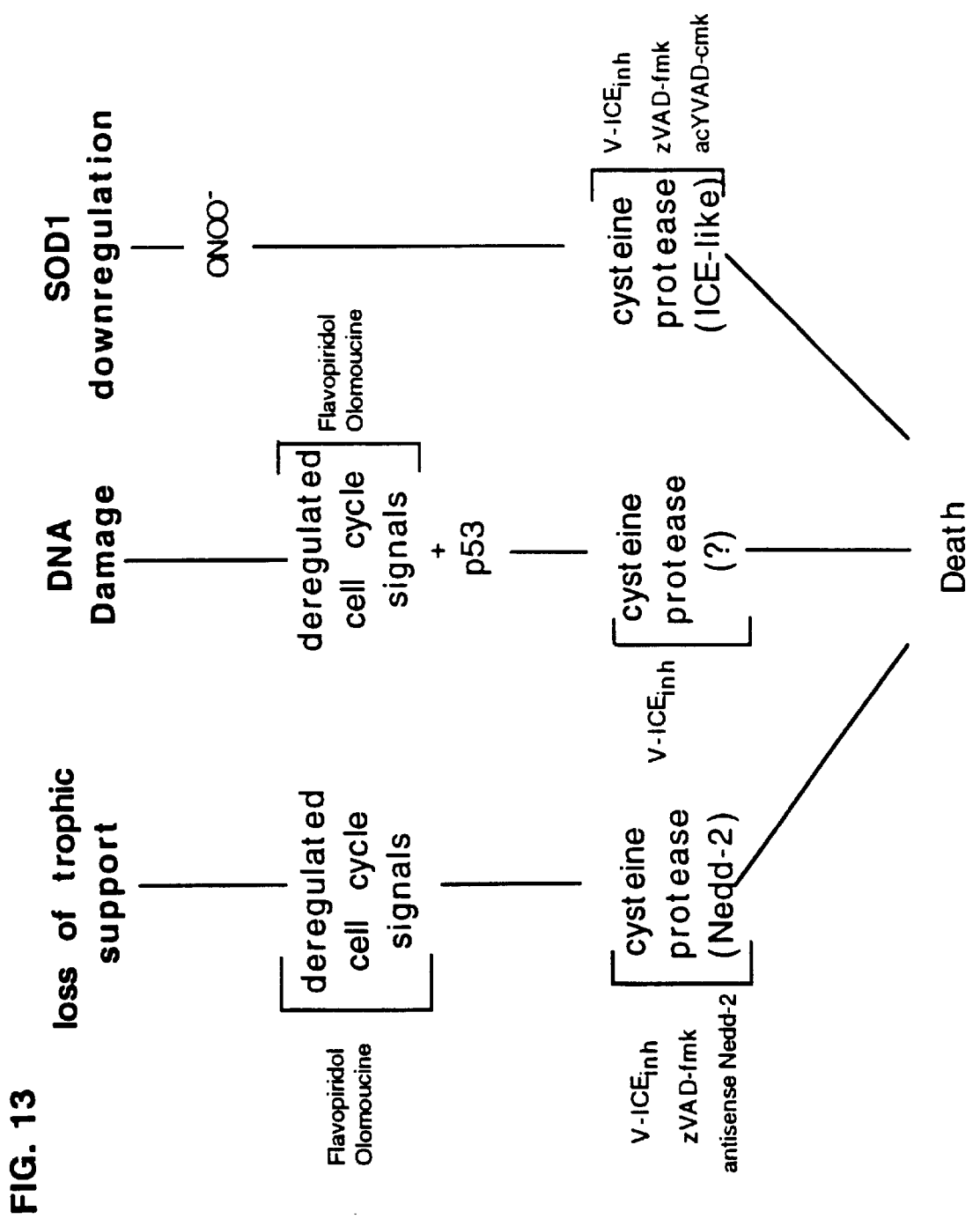

FIG. 13. Model for the differential death pathways induced by trophic factor deprivation, DNA damage, and superoxide dismutase 1 reduction in sympathetic neurons.

DETAILED DESCRIPTION OF THE INVENTION

The present invention provides for a compound having the structure: $(AA_1)_n$-Cys-$(AA_2)_m$ wherein n=0, 1, 2, 3, 4 or 5 and m=0, 1, 2, 3, 4 or 5, provided the sum of (n+m) is greater than or equal to two and less than or equal to five, if n=1, $(AA_1)_n$=Ala-, if n=2, $(AA_1)_n$=Gln-Ala-, if n≧3, $(AA_1)_n$=$(Xaa)_p$-Gln-Ala-, and Xaa=any amino acid and wherein if n=3, p=1, if n=4, p=2, if n=5, p=3, if m=1, $(AA_2)_m$=-Arg, if m=2, $(AA_2)_m$=-Arg-Gly, if m≧3, $(AA_2)_m$=-Arg-Gly-$(Xaa)_q$, wherein if m=3, q=1, if m=4, q=2, if m=5, q=3.

The present invention also provides for a compound having the structure: $(AA_1)_n$-Cys-$(AA_2)_m$ wherein n=0, 1, 2 or 3 and m=0, 1, 2 or 3, provided the sum of (n+m) is greater than or equal to two and less than or equal to five, if n=1, $(AA_1)_n$=Ala-, if n=2, $(AA_1)_n$=Gln-Ala-, if n=3, $(AA_1)_n$=$(Xaa)_p$-Gln-Ala-, and Xaa=any amino acid and wherein if n=3, p=1, if m=1,$(AA_2)_m$=-Arg, if m=2, $(AA_2)_m$=-Arg-Gly, if m=3, $(AA_2)_m$=-Arg-Gly-$(Xaa)_q$, wherein if m=3, q=1.

The present invention also provides for a compound having the structure: $(AA_1)_n$-Cys-$(AA_2)_m$ wherein n=2 or 3 and m=0, 1, 2 or 3, provided the sum of (n+m) is greater than or equal to two and less than or equal to five, if n=2, $(AA_1)_n$=Gln-Ala-, if n=3, $(AA_1)_n$=$(Xaa)_p$-Gln-Ala-, and Xaa=any amino acid and wherein if n=3, p=1, if m=1, $(AA_2)_m$=-Arg, if m=2, $(AA_2)_m$=-Arg-Gly, if m=3, $(AA_2)_m$=-Arg-Gly-$(Xaa)_q$, wherein if m=3, q=1.

The compound may be Ile-Gln-Ala-Cys-Arg-Gly (Seq. I.D. No. 1) or Gln-Ala-Cys-Arg-Gly (Seq. I.D. No. 3).

The present invention also provides for a compound having the structure:

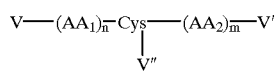

wherein n, m, $(AA_1)_n$ and $(AA_2)_m$ are as described above. In the compound each V, V' or V" is independently an agent capable of specifically directing the compound to a cell. V, V' or V" may be a polypeptide including at least a portion of an Antennepedia polypeptide. V, V' or V" may be at least a portion of a polypeptide including the sequence NPyS-Arg-Gln-Ile-Lys-Ile-Trp-Phe-Gln-Asn-Arg-Arg-Met-Lys-Trp-Lys-Lys-(Seq. I.D. No. 9). The compound may be NPyS-Arg-Gln-Ile-Lys-Ile-Trp-Phe-Gln-Asn-Arg-Arg-Met-Lys- Trp-Lys-Lys-Ile-Gln-Ala-Cys-Arg-Gly (Seq. I.D. No. 10). The compound may be NPyS-Arg-Gln-Ile-Lys-Ile-Trp-Phe-Gln-Asn-Arg-Arg-Met-Lys-Trp-Lys-Lys-Gln-Ala-Cys-Arg-Gly (Seq. I.D. No. 11). V, V' or V" may be independently an antibody, an adjuvant or a cell-specific ligand. The cell may be a neuronal cell, a cardiac cell or a liver cell.

The peptidomimetic compound may be at least partially unnatural. The peptidomimetic compound may be a small molecule mimic of Ile-Gln-Ala-Cys-Arg-Gly or of Gln-Ala-Cys-Arg-Gly. The compound may have increased stability, efficacy, potency and bioavailability by virtue of the mimic. Further, the compound may have decreased toxicity. The peptidomimetic compound may have enhanced mucosal intestinal permeability. The compound may be synthetically prepared. The compound of the present invention may include L-, D- or unnatural amino acids, alpha, alpha-disubstituted amino acids, N-alkyl amino acids, lactic acid (an isoelectronic analog of alanine). The peptide backbone of the compound may have at least one bond replaced with PSI-[CH=CH] (Kempf et al. 1991). The compound may further include trifluorotyrosine, p-Cl-phenylalanine, p-Br-phenylalanine, poly-L-propargylglycine, poly-D,L-allyl glycine, or poly-L-allyl glycine.

One embodiment of the present invention is a peptidomimetic compound having the biological activity of the structure: $(AA_1)_n$-Cys-$(AA_2)_m$ as described above wherein the compound has a bond, a peptide backbone or an amino acid component replaced with a suitable mimic. Examples of unnatural amino acids which may be suitable amino acid mimics include β-alanine, L-α-amino butyric acid, L-γ-amino butyric acid, L-α-amino isobutyric acid, L-ε-amino caproic acid, 7-amino heptanoic acid, L-aspartic acid, L-glutamic acid, cysteine (acetamindomethyl), N-ε-Boc-N-α-CBZ-L-lysine, N-ε-Boc-N-α-Fmoc-L-lysine, L-methionine sulfone, L-norleucine, L-norvaline, N-α-Boc-N-δCBZ-L-ornithine, N-δ-Boc-N-α-CBZ-L-ornithine, Boc-p-nitro-L-phenylalanine, Boc-hydroxyproline, Boc-L-thioproline. (Blondelle, et al. 1994; Pinilla, et al. 1995).

Another embodiment of the present invention is a pharmaceutical composition including an amount of a compound having the structure: $(AA_1)_n$-Cys-$(AA_2)_m$ or

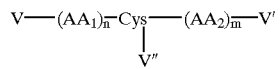

as described above effective to inhibit the death of a cell and a pharmaceutically acceptable carrier thereof. The cell may be a neuronal cell, a cardiac cell or a liver or a hepatic cell. The carrier may include a diluent. The carrier may include an appropriate adjuvant, a herpes virus, a liposome, a microencapsule, a neuronal cell receptor ligand, a neuronal-specific virus, a polymer encapsulated cell or a retroviral vector. The pharmaceutically acceptable carrier may include an aerosol, intravenous, oral or topical carrier.

Another embodiment of the present invention is a method of inhibiting death of a cell which includes contacting the cell with an amount of a compound having the structure:

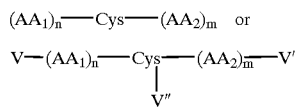

effective to inhibit death of the cell. The cell may be in a subject. The subject may be a human. The cell may be a neuronal cell, a cardiac cell or a hepatic cell.

Another embodiment of the present invention is a method for alleviating symptoms of a neurodegenerative disorder in a subject which includes administering to the subject the compounds described hereinabove, the compound being present in an amount effective to inhibit neuronal cell death and thus alleviate the symptoms of the neurodegenerative disorder in the subject.

The neurodegenerative disorder may be associated with aging, Alzheimer's disease, dentatorubral and pallidolyusian atrophy, Huntington's disease, Machoado-Joseph disease, multiple sclerosis, muscular dystrophy, Parkinson's disease, senility, spinocerebellar ataxia type I, spinobulbar muscular atrophy, stroke, trauma. The subject may be a mammal. The mammal may be a human. The administration may include aerosol delivery; intralesional, intraperitoneal, intramuscular or intravenous injection; infusion; liposome-mediated delivery; anal, nasal, oral, ocular, otic or topical delivery of the pharmaceutical composition.

The present invention also provides for a method for alleviating symptoms of a cardiovascular disorder in a subject which includes administering to a subject either of the compounds described hereinabove, the compound being present in an amount effective to inhibit cardiac cell death and thus alleviate the symptoms of the cardiovascular disorder in the subject.

The present invention also provides for a method of alleviating symptoms of a liver disorder in a subject which includes administering to the subject either of the compounds described hereinabove, the compound being present in an amount effective to inhibit liver cell death and thus, alleviate the symptoms of the liver disorder in the subject.

Previously, researchers have searched for an inhibitor of ICE which is capable of acting as a psuedosubstrate as discussed above. This invention provides an unusual approach to the problem of inhibiting the ICE enzyme. The present invention provides for compounds which are capable of inhibiting cell death. These compounds may be capable of inhibiting ICE and preventing cell death. Specifically, the compounds may be capable of preventing neuronal cell death, cardiac cell death or hepatic (liver) cell death.

The effectiveness of the compounds described herein as an enzyme inhibitor to prevent cell death is a surprising result that would not have been anticipated by one skilled in the art. The conventional approach to developing an inhibitor of an enzyme is to mimic the substrate of that enzyme. The non-active substrate mimic is usually designed to bind to the active site of the enzyme to be inhibited. This binding is usually at a higher affinity than the normal substrate. Thus, while the active site of the enzyme is bound to the mimic, it is non-productive and not active. Design of a compound which is capable of occupying the active site of an enzyme and competing with the normal substrate for binding is the classic approach to enzyme inhibition. The present invention, however, provides for an alternate approach to this problem utilizing a portion of the enzyme itself.

Also provided by the invention are pharmaceutical compositions comprising therapeutically effective amounts of polypeptide products of the invention together with suitable diluents, preservatives, solubilizers, emulsifiers, adjuvants and/or carriers. A "therapeutically effective amount" as used herein refers to that amount which provides a therapeutic effect for a given condition and administration regimen. Such compositions are liquids or lyophilized or otherwise dried formulations and include diluents of various buffer content (e.g., Tris-HCl., acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polyglycolic acid, hydrogels, etc, or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance. The choice of compositions will depend on the physical and chemical properties of the protein having the activity of inhibiting neuronal cell death. For example, a product derived from a membrane-bound form of the protein may require a formulation containing detergent. Controlled or sustained release compositions include formulation in lipophilic depots (e.g., fatty acids, waxes, oils). Also comprehended by the invention are particulate compositions coated with polymers (e.g., poloxamers or poloxamines) and the compound coupled to antibodies directed against tissue-specific receptors, ligands or antigens or coupled to ligands of tissue-specific receptors. Other embodiments of the compositions of the invention incorporate particulate forms protective coatings, protease inhibitors or permeation enhancers for various routes of administration, including parenteral, pulmonary, nasal, oral, injection or infusion by intravenous, intraperitoneal, intracerebral, intramuscular, intraocular, intraarterial or intralesional.

The present invention incorporates U.S. Pat. Nos. 5,446,128, 5,422,426 and 5,440,013 in their entireties as references which disclose the synthesis of peptidomimetic compounds and methods related thereto. The compounds of the present invention may be synthesized using these methods. The present invention provides for peptidomimetic compounds which have substantially the same three-dimensional structure as those peptide compounds described herein (Ojala et al., 1995; Bock et al., 1992; Lee et al., 1995).

In addition to the compounds disclosed herein having naturally-occurring amino acids with peptide or unnatural linkages, the present invention also provides for other structurally similar compounds such as polypeptide analogs with unnatural amino acids in the compound. Such compounds may be readily synthesized on a peptide synthesizer available from vendors such as Applied Biosystems, Dupont and Millipore.

The present invention includes a delivery system which links the polypeptide to an agent which directs the polypeptide to neuronal cells in order to facilitate entry into the cells. The Antennepedia protein may be used as such a delivery agent. The invention also includes therapeutic uses of the isolated polypeptide to prevent neuronal cell death, cardiac cell death or hepatic cell death. Related therapeutic uses include treating stroke, trauma, neurodegenerative disorders or regenerating neurons, cardiac ischemia, liver disease, pulmonary disease, congestive heart disease, myocardial infarction, Alzheimer's disease, Parkinson's disease, senility, aging, muscular dystrophy, multiple sclerosis, Huntington's disease, spinocerebellar ataxia type I, Machoado-Joseph disease, spinobulbar muscular atrophy or dentatorubral and pallidolyusian atrophy.

The present invention provides for a method of identifying a peptide compound as an enzyme inhibitor which includes preparing suitable peptide fragments chosen from an active site of an enzyme, assaying the fragments and identifying the fragments which are enzyme inhibitors. The present invention also encompasses a compound obtained by this method. The enzyme may include a protein kinase enzyme, an enzyme associated with cellular signaling, an enzyme associated with cell death, or a bcl-2 enzyme. The enzyme may also include an enzyme associated with cellular communication, cell division, cellular metabolism, cell adhesion, gene expression or protein processing. (Adams M. D. et al., 1995)

The present invention also provides for a method of inhibiting the activity of an enzyme on a substrate which includes contacting the enzyme with a peptide fragment or a peptidomimetic fragment from an active site of the enzyme under conditions that the fragment is capable of binding to the substrate of the enzyme and thus inhibiting the activity of the enzyme on the substrate.

Another embodiment of the present invention is a method of inhibiting the activity of an enzyme on a substrate in a cell which includes contacting the enzyme with a peptide fragment or a peptidomimetic fragment from an active site of the enzyme under conditions that the fragment is capable of binding to the substrate of the enzyme and thus inhibiting the activity of the enzyme on the substrate.

This invention is illustrated in the Experimental Detail section which follows. These sections are set forth to aid in an understanding of the invention but are not intended to, and should not be construed to, limit in any way the invention as set forth in the claims which follow thereafter.

Experimental Details

EXAMPLE 1

The Contrasting Roles of ICE-family Proteases and Interleukin-1β in Apoptosis Induced by Trophic Factor Withdrawal and by SOD1 Down-regulation Previous results have shown that down-regulation of $Cu^{++}$—$Zn^{++}$ superoxide dismutase (SOD1) in PC12 cells produces apoptosis by mechanisms that are distinguishable upstream from those utilized by trophic factor deprivation (Troy and Shelanski, 1994) but which may converge downstream in a final common pathway. To determine whether the ICE (interleukin 1β converting enzyme) family of proteases is required for apoptosis induced by oxidative stress as well as by trophic factor withdrawal, a novel Antennapedia-linked peptide inhibitor was developed that mimics the common catalytic site of these enzymes and thereby blocks their access to substrates, a unique approach to enzyme inhibition. Blockade of ICE family proteases by this inhibitor as well as by a permeant competitive antagonist, rescues PC12 cells from apoptotic death following trophic factor/NGF-deprivation as well as from peroxynitrite-dependent apoptosis induced by down-regulation of SOD1. In spite of the protection afforded by ICE family inhibitors in these two paradigms, blocking antibodies to IL-1β and the IL-1 receptor antagonist (IL-Ra) were fully protective only in the case of SOD1 down-regulation. The blocking antibody failed to protect PC12 cells from trophic factor withdrawal and the receptor antagonist was only partially protective at very high concentrations. Similarly, there were substantial differences in the concentrations of pseudo substrate inhibitors which rescued cells from SOD1 down-regulation and trophic factor deprivation. These results suggest the involvement of different members of the ICE family, different substrates or both in the two different initiating causes of cell death.

Introduction

Oxidative damage is a major contributor to cell death in a variety of degenerative disorders (Coyle and Puttfarcken, 1993). In model systems, it appears to be initiated by mechanisms that are distinguishable from apoptosis brought about by serum or trophic factor withdrawal (Troy and Shelanski, 1994). In the clonal rat pheochromocytoma line PC12, a commonly used model for neuronal differentiation and cell death (Greene and Tischler, 1976; Rukenstein et al., 1991; Ferrari et al., 1995; Pittman et al., 1993; and Ferrari and Greene, 1994), both trophic factor withdrawal and down-regulation of $Cu^{++}$—$Zn^{++}$ superoxide dismutase (SOD1) result in apoptosis (Troy and Shelanski, 1994 and Batistatou and Greene, 1991). The former, trophic factor withdrawal, is inhibited by CAMP analogues (Rukenstein et al., 1991), N-acetylcysteine (Ferrari et al., 1995) and a variety of growth factors including NGF (Rukenstein et al., 1991 and Pittman et al., 1993), but not by vitamin E (Ferrari et al., 1995) or inhibitors of nitric oxide synthase (Farinelli et al., 1995), and appears to be related to an abortive attempt to traverse the cell cycle (Ferrari and Greene, 1994). The latter, SOD1 down regulation, in contrast, is insensitive to cAMP analogs, N-acetylcysteine and growth factors, but is blocked by vitamin E and, consistent with a role for peroxynitrite generation, by nitric oxide synthase inhibitors (Troy and Shelanski, 1994). Despite these divergent initial causes of death, it has been shown that bcl-2 overexpression rescues PC12 cells from death induced by either trophic factor deprivation (Batistatou et al., 1993) or SOD1 down-regulation indicating that the apoptotic pathways ultimately converge. Inhibition of ICE-like proteases has also been shown to block apoptosis induced by trophic factor deprivation but the role of these enzymes in oxygen-radical induced death has not been previously explored. The studies presented here show an obligate role for ICE-like proteases in both paradigms and place them, together with bcl-2, on the shared branch of the apoptotic pathway. However, these studies also show that IL-1β itself can play a critical role in death initiated by SOD1 down-regulation, but only a minor role in apoptosis caused by withdrawal of trophic support and therefore suggest involvement of different members of the ICE family in the two initiating causes of cell death.

Materials and Methods

Cell Culture of PC12 Cells:

PC12 cells were grown as previously described (Greene and Tishcler, 1976) on rat-tail collagen-coated dishes in RPMI 1640 medium containing 5% fetal calf serum and 10% heat-inactivated horse serum (complete medium). NGF primed PC12 cells were grown for at least 7 days in RPMI 1640 medium plus 1% horse serum and NGF (100 ng/ml). For cell survival assays involving trophic factor deprivation, cells (either naive or NGF-pretreated) were extensively washed in serum-free RPMI 1640 medium and re-plated on fresh collagen-coated 24-well dishes as previously described (Rukenstein et al., 1991) in RPMI 1640 medium lacking serum or NGF. For SOD1 down-regulation survival assays, cells were re-plated in complete medium with V-ASOD1 (vector linked antisense oligonucleotide to SOD1, 50 nM). Various concentrations of ICE inhibitors were included in the medium as indicated. Numbers of viable cells per culture were determined by quantifying intact nuclei as previously described (Rukenstein et al., 1991). Counts were performed in triplicate and reported as means±SEM.

Cell Culture of Sympathetic Neurons:

Sympathetic neuron cultures were prepared from 2 day old rat pups, as previously described (Ferrari et al., 1995). Cultures were grown in 24-well collagen coated dishes in RPMI 1640 medium plus 10% horse serum with mouse NGF (100 ng/ml). One day following plating, uridine and 5-fluorodeoxyuridine (10 µM each) were added to the cultures and left for three days to eliminate non-neuronal cells. On the sixth day following plating NGF was removed by washing the cultures three times with RPMI 1640 medium plus 10% horse serum, followed by the addition of medium containing anti-mouse NGF (1:200, Sigma) with or without ICE inhibitors. Each culture was scored, as previously described (Rydel and Greene, 1988), as numbers of living, phase-bright neurons at various times. Three replicate cultures were assessed for each condition and data were normalized to numbers of neurons present in each culture at the time of NGF withdrawal and reported as mean±SEM.

Assay of ICE Activity:

Recombinant human pro-IL-1β was purchased from Cistron Biotechnology (Pine Brook, N.J.) as a 10 $\mu$g ml$^{-1}$ solution in 10 mM Tris (pH 8.1), 0.1% Triton X-100, 0.1 mM EDTA and 10% glycerol. The assay of pro-IL-1 cleavage was carried out in buffer containing 100 mM HEPES (pH 7.5), 0.1% CHAPS, 10 mM DTT and 10% sucrose. 10 ng of pro-IL-1-B was incubated with or without 1 mM IQACRG (Seq. I.D. No. 1) for 30 minutes at 37° C. 3 units of recombinant human ICE were then added and the reaction mixtures were incubated for 30 minutes at 25° C. (Thornberry, 1994). Reactions were stopped with 2× Laemmli sample buffer (Laemmli, 1970) containing 10 mM DTT and the samples were boiled for 3 minutes and subjected to SDS-PAGE (15% acrylamide) followed by immunoblotting. The blot was probed with a monoclonal antibody to human IL-1β (0.25 $\mu$g/ml, kindly provided by the National Cancer Institute), and then visualized by ECL using anti-mouse IgG peroxidase as secondary antibody.

Coupling of Antennapedia Peptide (Vector Peptide) with the Hexapeptide IQACRG (Seq. I.D. No. 1)—ICE Family Inhibitor:

IQACRG (Seq. I.D. No. 1) (synthesized by e.g., Multiple Peptide Systems (California), American Peptide Company (California), The Midland Certified Reagent Company (Texas)) was resuspended in TCEP (tris(2-carboxyethyl)-phosphine hydrochloride) buffer, an equimolar ratio of NPyS-pAntp$_{43-58}$ peptide (Penetratin 1, Oncor, Md.) hereafter called the vector peptide) was added and the mixture was incubated at 20° C. for 2 hours. The sequence of the vector peptide is NPyS-Arg-Gln-Ile-Lys-Ile-Trp-Phe-Gln-Asn-Arg-Arg-Met-Lys-Trp-Lys-Lys (Seq. I.D. No. 9). The yield of the reaction, estimated by SDS-PAGE followed by Coomasie blue staining, was routinely above 50%. Control peptides (GRCAQI (Seq. I.D. No. 4) and ICGRQA (Seq. I.D. No. 5) were coupled to the vector peptide in the same way.

Assay of IL-1β:

IL-1β was quantified by ELISA using the Intertest-1βX kit (Genzyme, Cambridge, Mass.). PC12 cells were grown as described above, on 24-well plates, in 500 $\mu$l of medium. After one day incubation, medium was removed and IL-1β measured following the manufacturer's instructions, and number of viable cells in each well quantified.

Additional Materials:

ZVAD-FMK (Seq. I.D. No. 2) was from Enzyme Systems Products, Inc. (Dublin, Calif.) and ZYVAD-CMK (Seq. I.D. No. 6) from Bachem (King of Prussia, Pa.). Monoclonal human and murine IL-1β antibody (3ZD) was kindly provided by the NCI, as was recombinant human IL-1β. Blocking monoclonal hamster anti-mouse IL-1β was purchased from Genzyme, (Cambridge, Mass.), blocking anti-murine IL-1a from R&D Systems.

Results

In these studies, three paradigms were used to induce apoptosis in cultured PC12 cells. In the first, naive PC12 cells without NGF exposure are induced to die by the withdrawal of serum. In the second, PC12 cells which have been "primed" by NGF pretreatment in serum-free medium for a week and which have a neuronal morphology undergo apoptosis upon withdrawal of NGF and serum. The third model induces apoptosis by down-regulating superoxide dismutase 1 (SOD1) in either primed or naive cells by exposure to an SOD1 antisense oligonucleotide. Withdrawal of serum results in the death of 50–85% of the cells within 24 hours and NGF/serum deprivation and SOD1 down-regulation in 50–60% mortality by this time (Troy and Shelanski, 1994; Rukenstein et al., 1991; and Ferrari et al., 1995).

Figure 1A:
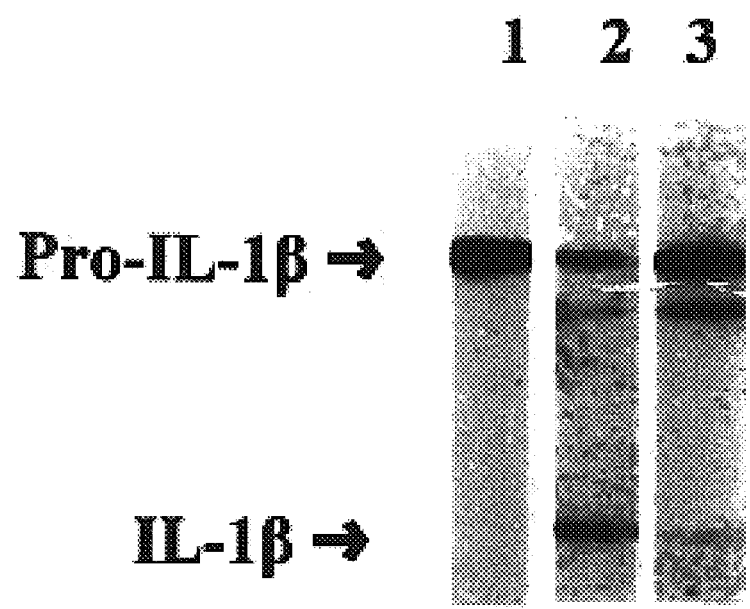
FIGS. 1A and 1B. (A) IQACRG (Seq. I.D. No. 1) blocks cleavage of pro-IL-1β by ICE. Enzyme digests were subjected to SDS-PAGE (15% acrylamide) followed by immunoblotting. The blot was probed with a monoclonal antibody to human and murine IL-1β (1 μg/ml), and then visualized by ECL using anti-mouse IgG peroxidase as a secondary antibody. Lane 1=pro-IL-1β, lane 2=pro-IL-Iβ+ICE, lane 3=pro-IL-1β+ICE+IQACRG (Seq. I.D. No. 1). (B) Schematic illustration of the coupling of Antennapedia peptide (vector peptide; hashed box) with the hexapaptide IQACRG (Seq. I.D. No. 1).
Figure 1B:
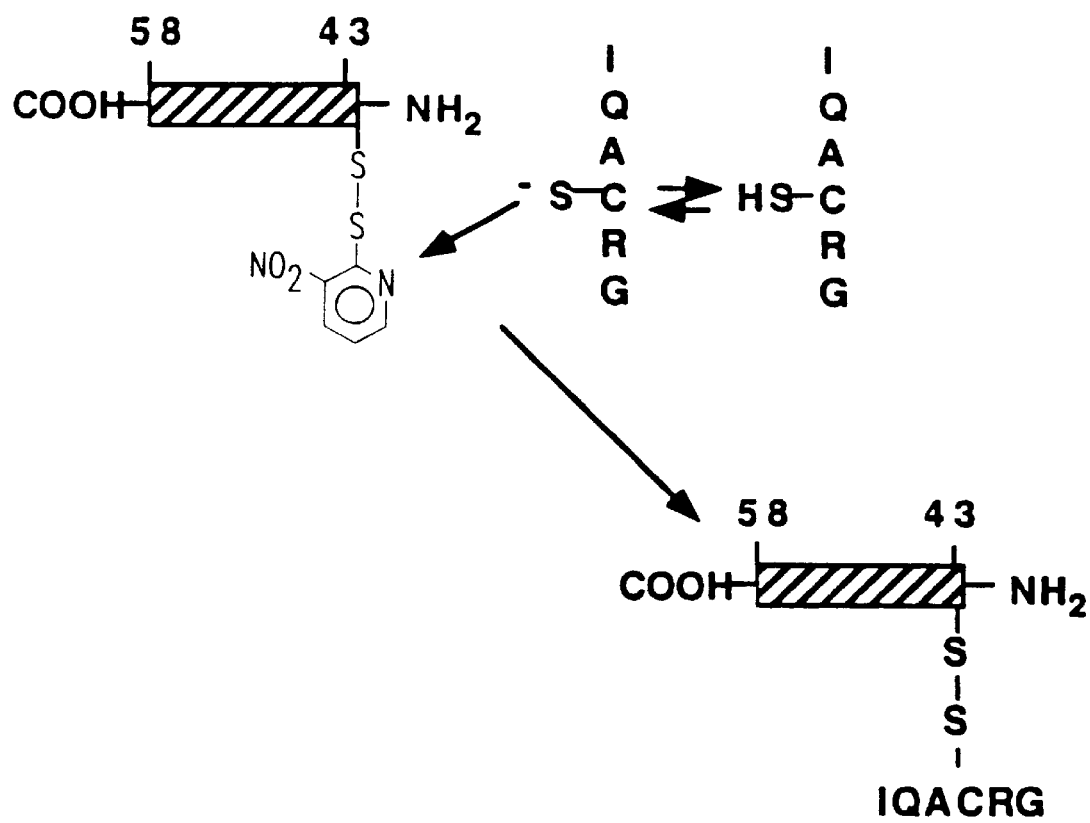

To investigate the role that ICE-like proteases play in apoptosis induced by these treatments, a peptide was utilized which mimics the conserved active site, IQACRG (Seq. I.D. No. 1), of the ICE-family of proteases (Wang et al., 1994) and which was anticipated to bind to substrates and thereby block their cleavage. IQACRG (Seq. I.D. No. 1) should inhibit activity regardless of the specific substrate, avoiding the problem posed by differences in the preferred substrate for individual members of the ICE family. A search of the Swiss Protein Bank revealed that only ICE family members have this sequence. This approach also minimizes the chance of blocking cysteine proteases other than those in the ICE-family. To verify that IQACRG (Seq. I.D. No. 1) blocks ICE activity, the capacity of recombinant ICE to cleave recombinant pro-IL-1β was tested in the presence or absence of the peptide. As shown in FIG. 1A, the peptide effectively inhibits ICE cleavage of pro-IL-1β in vitro. There is some cleavage in the presence of the inhibitor but much less than seen with ICE alone. Cellular uptake of the IQACRG (Seq. I.D. No. 1) peptide was facilitated by linking it to the highly penetrant 16 amino acid Antennapedia peptide (FIG. 1B) which greatly enhances cellular uptake of peptides as well as antisense oligonucleotides (Prochiantz and Theodore, 1995). The Antennapedia vector peptide (V-) was linked to IQACRG (Seq. I.D. No. 1) (ICE$_{inh}$) by a reducible disulfide bond to form V-ICE $_{inh}$. Previous studies have shown that after uptake, reduction of the S—S bond releases free peptide within the cell.

Inhibitors of ICE-like Proteases Protect PC12 Cells and Sympathetic Neurons from Death Induced by Withdrawal of Serum and NGF.

Figure 2A:
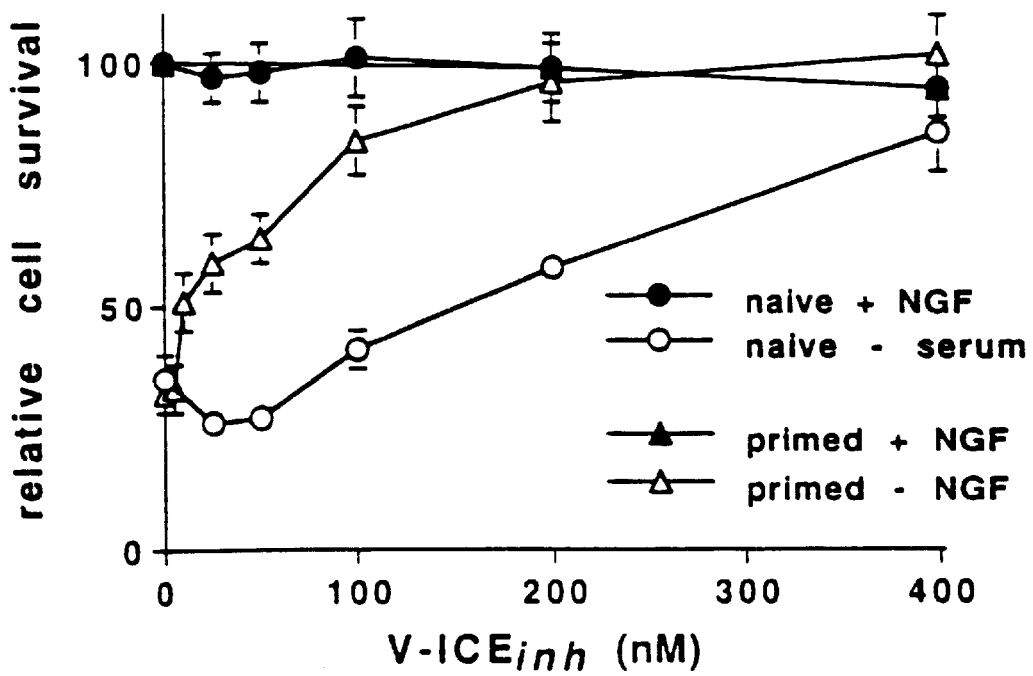
FIGS. 2A, 2B and 2C. V-ICE$_{inh}$ protects PC12 cells from death induced by withdrawal of serum/NGF. (A) Protection of PC12 cells from serum/trophic factor deprivation induced death. Naive and primed PC12 cells (PC12 cells treated with NGF for more than 7 days) were extensively washed and plated in serum-free RPMI 1640 with the indicated concentrations of V-ICE$_{inh}$. Control cultures received readditions of NGF. One day later, the numbers of surviving cells were determined by lysing the cultures and counting intact nuclei. Cell number is reported relative to those present in control cultures with NGF and without V-ICE$_{inh}$ (designated as 100). The numbers of cells in control cultures at 24 hrs were within 10% of those initially plated. (B) Time course of protection of NGF-deprived PC12 cells by V-ICE$_{inh}$. Primed PC12 cells were deprived of NGF as above and then maintained with or without V-ICE$_{inh}$ (200 nM) for the indicated times. V-ICE$_{inh}$ was added at time 0 (1 addition) or at time 0 and at 24 hours (2 additions), as indicated and quantifications of survival were made at the indicated times by lysing the cells and counting nuclei as described in (A). (C) ZVAD-FMK (Seq. I.D. No. 2) protects PC12 cells from withdrawal of trophic support. PC12 cells were washed free of serum as in FIG. 2A and plated in serum-free medium with the indicated concentrations of ZVAD-FMK (Seq. I.D. No. 2) (ZVAD-fluoromethylketone, Enzyme Systems Products, Dublin, Calif.). Control cultures received NGF. At one day of incubation cells were lysed and surviving numbers determined as in FIG. 2A.
Figure 2B:
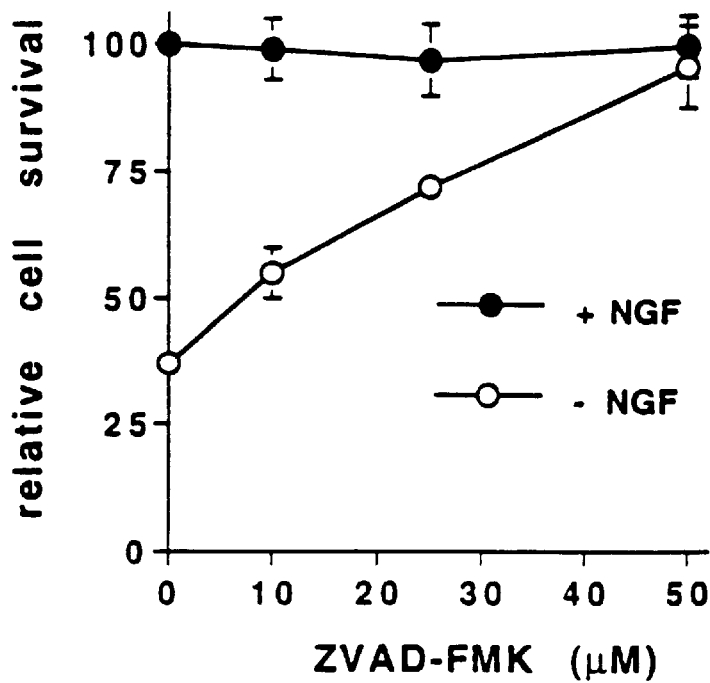
Figure 2C:
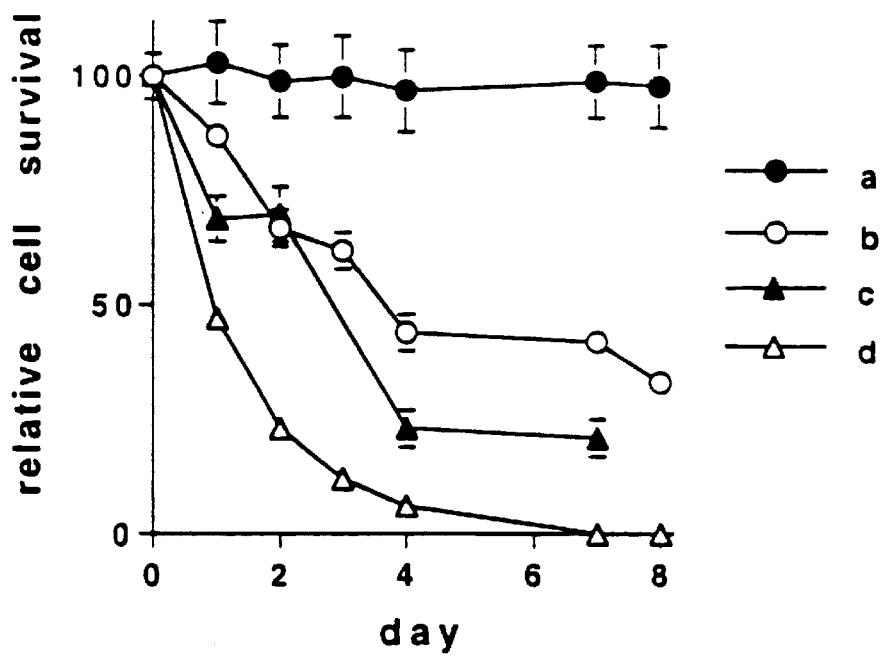

From the reported inhibition of cell death in NGF-deprived sensory neurons by crmA (Gagliardini et al., 1994), it was possible that if V-ICE$_{inh}$ significantly inhibits ICE-family proteases in vivo, it should block cell death caused by withdrawal of serum from naive PC12 cells and serum and NGF from neuronally-differentiated PC12 cells. The data in FIG. 2A show that this is the case with complete protection at 24 hours obtained with 200–400 nM peptide. Treatment with V-ICE$_{inh}$ provided partial protection of naive and primed PC12 cells (FIG. 2C) for at least 8 days. To control for possible non-specific actions of V-ICE$_{inh}$, reversed and scrambled V-linked peptides were also tested in the PC12 cell system and neither was found to be effective or toxic over the same concentration range. To further explore the role of ICE proteases in this system, the permeant competitive inhibitor ZVAD-FMK (Seq I.D. No. 2) (ZVAD-fluoromethylketone) was also assessed. This also blocked cell death, but required much higher concentrations (50 $\mu$M) to be fully protective (FIG. 2B). The peptide ZYVAD-CMK (Seq. I.D. No. 6) (ZYVAD-chloromethylketone) (Lazebnik et al., 1994), an additional competitive inhibitor of ICE family proteases, was only partially effective at 250 $\mu$M.

Figure 3A:
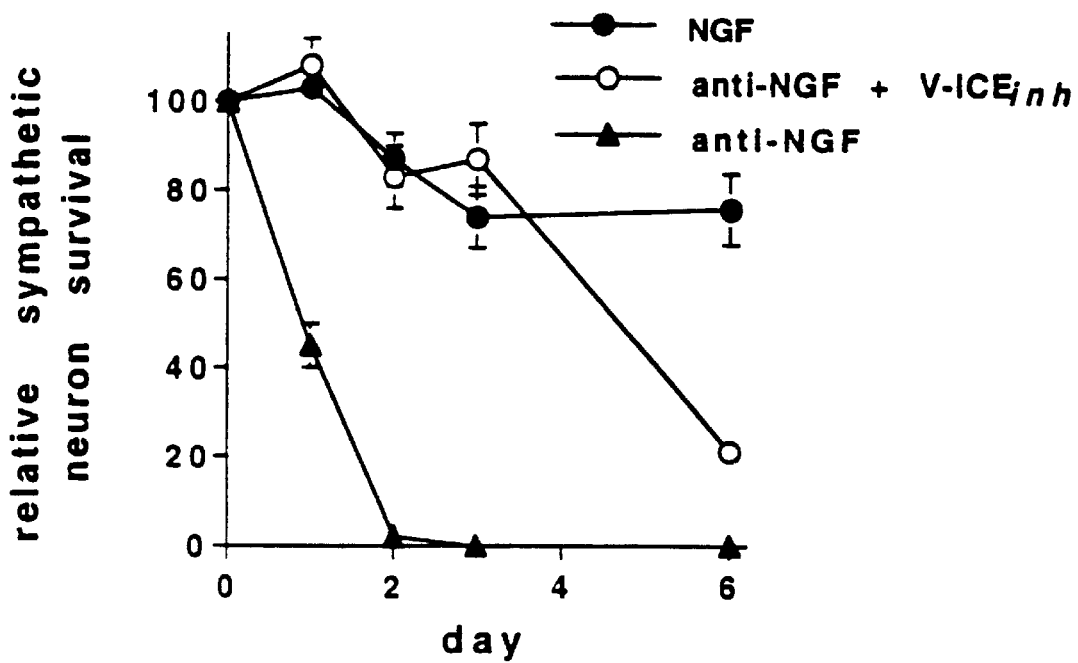
Figure 3B:
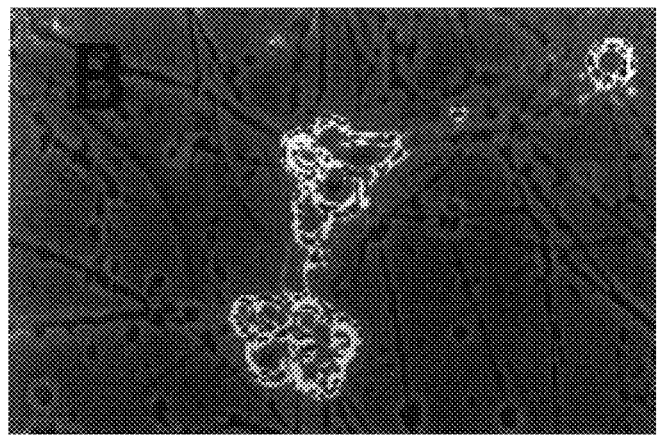
Figure 3C:
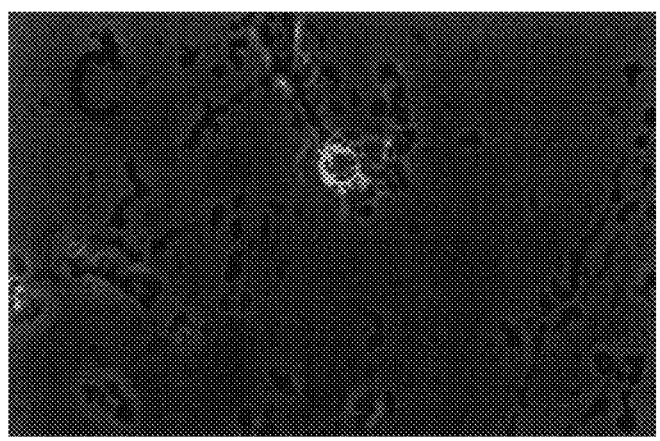
Figure 3D:
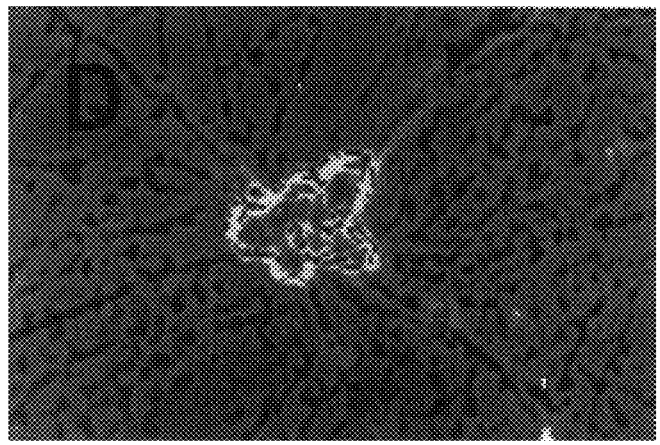

In parallel experiments, NGF-deprived sympathetic neurons exposed to V-ICE$_{inh}$ (50 nM) were completely protected from death for 3 days and death was retarded for at least 6 days (FIG. 3A). Although a second addition of V-ICE$_{inh}$ after 24 hr somewhat prolonged survival time, subsequent treatment at daily intervals did not. As reported with crmA protection (Gagliardini et al., 1994), cell bodies but not neurites are maintained with V-ICE$_{inh}$ (FIGS. 3B–D). ZVAD-FMK (Seq. I.D. No. 2) (100 μM) also protected from NGF deprivation, but ZYVAD-CMK (Seq. I.D. No. 9) had no effect even at 250 μM.

V-ICE$_{inh}$ Protects PC12 Cells from Death Induced by Down-regulation of SOD1.

Exposure of PC12 cell cultures to the antisense oligonucleotide ASOD1 results in rapid down-regulation of SOD1 activity and death of 50–60% of the cells within 24 hr (Troy and Shelanski, 1994). As shown in FIG. 4A, V-ICE$_{inh}$ protects both naive and NGF-treated PC12 cells from death in this paradigm. Control, scrambled and reversed V-linked peptides were, in contrast, without effect. V-ICE$_{inh}$ had no effect on the capacity of ASOD1 to lower cellular SOD1. Protection was the same whether the experiment was done in complete medium or in RPMI 1640 supplemented with 3 μM insulin. The protective effects of inhibiting ICE-family proteases were confirmed using the inhibitory ZVAD-FMK (Seq. I.D. No. 2) peptide (FIG. 4B). The dose of V-ICE$_{inh}$ (25–50 nM) required for maximal protection was again considerably lower than that for ZVAD-FMK (6 μM) (Seq. I.D. No. 2). However, the concentration of either required to protect cells from SOD1 down-regulation were significantly lower that those needed to block apoptosis caused by trophic factor withdrawal (compare FIGS. 2A and 4A). Moreover, ZYVAD-CMK (Seq. I.D. No. 9) afforded full protection from SOD1 down-regulation at 50 μM, in contrast to its partial protection from trophic factor withdrawal at 250 μM.

Both Antibodies Against IL-1 and an IL-1 Receptor Antagonist Protect Fully Against SOD1 Down-regulation but not Trophic Factor Withdrawal.

Figure 5A:
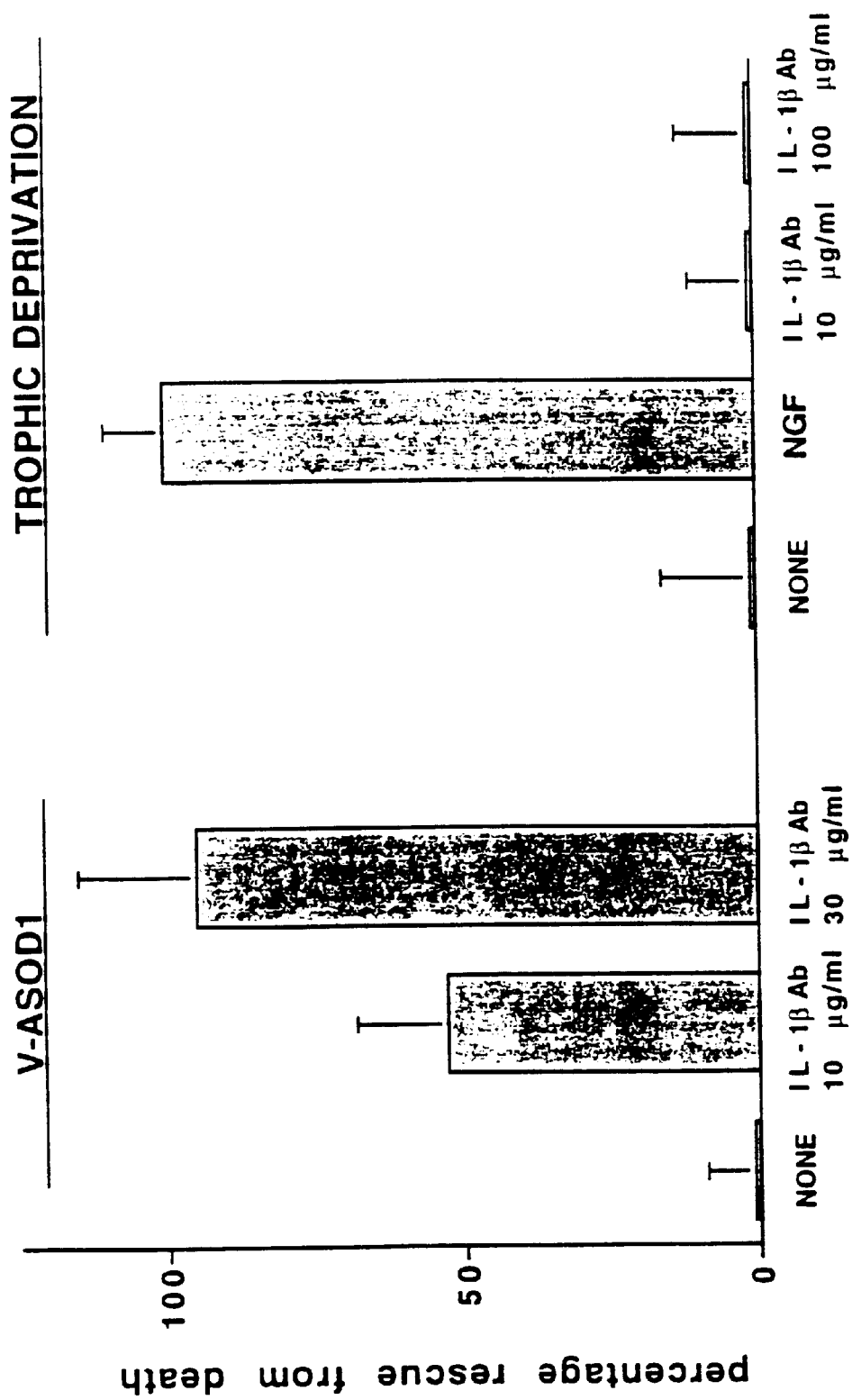
Figure 5B:
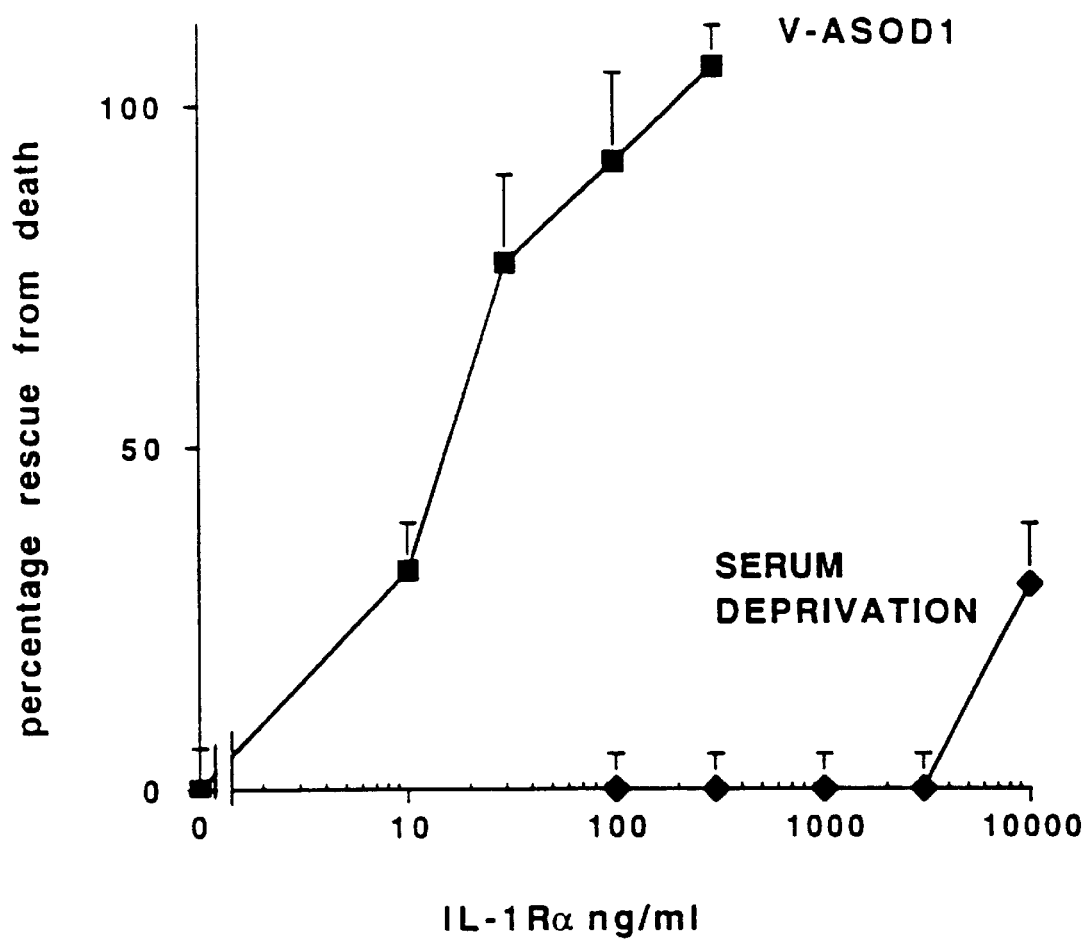

The inhibition of apoptosis by ICE inhibitors in each of the paradigms raised the question of whether IL-1β itself plays a direct role in cell death. Exposure of V-ASOD1 treated (SOD1 deficient) PC12 cells to blocking antibodies against mIL-1β at 30 μg/ml (FIG. 5A) or to the IL-1 receptor antagonist (rmIL-1Ra) at 100 ng/ml (FIG. 5B) completely suppressed cell death. Similar concentrations of antibodies against mIL-1a and a non-blocking antibody to mIL-1β failed to confer protection under these conditions. In contrast to the results in cells in which SOD1 had been down-regulated, the mIL-1β blocking antibody failed to protect cells from trophic factor withdrawal at concentrations up to 100 μg/ml (FIG. 5A). Furthermore, the IL-1 receptor antagonist improved survival under these conditions only modestly and then only at a concentration of 10,000 ng/ml (FIG. 5B), two orders of magnitude greater than the dose which fully protected cells from SOD1 down-regulation.

Figure 5C:
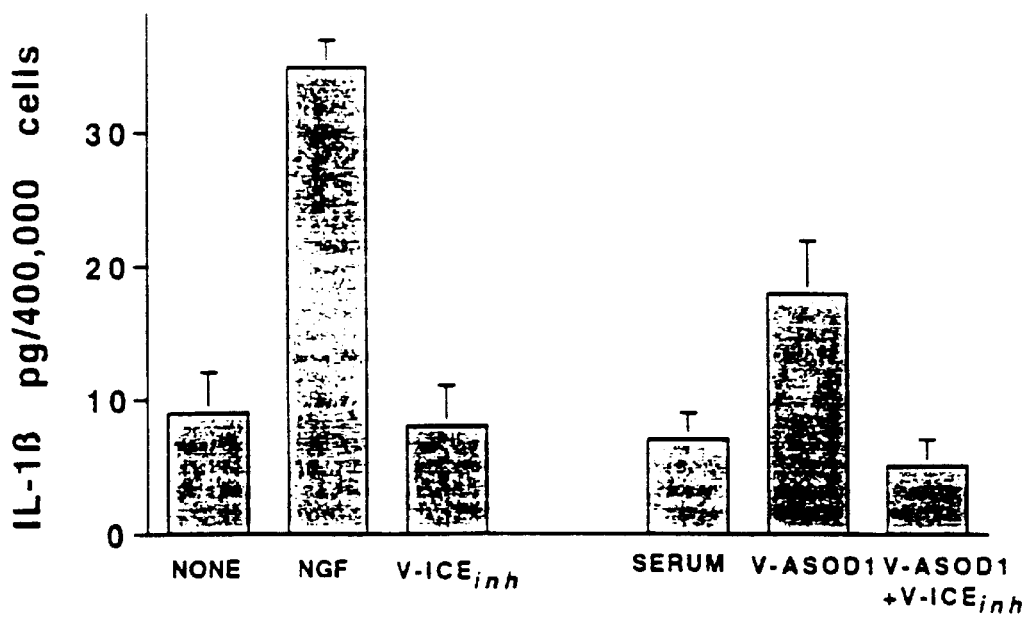
Figure 5D:
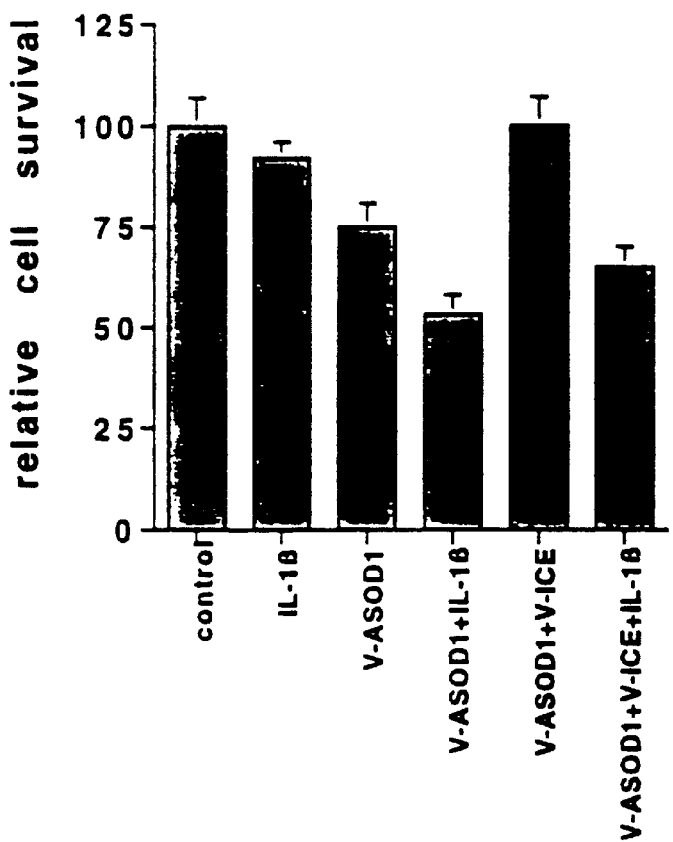

The disparity in effects afforded by blocking IL-1β or the IL-1 receptor in the two paradigms raised the issue of whether IL-1β secretion is differentially affected. When SOD1 is down-regulated there is an almost 3-fold increase in IL-1β secretion per cell at 24 h, an increase which is blocked by V-ICE$_{inh}$ (FIG. 5C). Upon withdrawal of trophic support there is no increase in IL-1β secretion at 24 h; in contrast cells treated with NGF manifest a 4-fold increase in IL-1β secretion (FIG. 5C). Similar trends were observed at 6 h of treatment in both paradigms.

The effectiveness of IL-1β blockade in protecting cells against SOD1 down-regulation led us to determine the effect of exogenous IL-1β in this paradigm. IL-1β itself has no effect, however IL-1β in conjunction with V-ASOD1 potentiates the cell death. IL-1β also abrogates the protection provided by V-ICE$_{inh}$.

Discussion:

Both the lack of trophic factors and damage by free radicals have been invoked as possible contributors to cell shrinkage and loss in neurodegenerative disorders including Parkinson's disease and Alzheimer's disease. In the studies presented here a single model neuronal culture system has been used to compare pathways leading to cell death resulting from either trophic factor withdrawal or from free radical damage following down-regulation of the copper-zinc superoxide dismutase. These pathways are quite divergent in their initial steps. For example, survival after trophic factor deprivation is promoted by cyclic AMP analogs (Rukenstein et al., 1991), N-acetylcysteine (Ferrari et al., 1995) and by nitric oxide generators (Farinelli et al., 1995) as well as by serum and growth factors (Rukenstein et al., 1991 and Pittman et al., 1993) but not by vitamin E (Ferrari et al., 1995). By comparison, cells are protected from SOD1 down-regulation by inhibitors of nitric oxide synthesis and by vitamin E (Troy and Shelanski, 1994), while death is unaffected by cAMP, growth factors (Troy and Shelanski, 1994), serum and N-acetylcysteine and enhanced by nitric oxide generators.

It has been previously demonstrated that inhibition of ICE-family proteases by crm-A protects neurons from trophic factor withdrawal (Gagliardini et al., 1994). By using a novel protease inhibitor designed to inhibit all members of the ICE family it is demonstrated herein that the same family of proteases is involved in free-radical induced apoptosis, suggesting that there is a shared downstream pathway leading to death from these two initially divergent causes. This finding of commonality is in agreement with earlier data showing that expression of bcl-2 also protects in both paradigms (Farinelli et al., 1995), as well as in a variety of systems in which cell death is initiated by different means (Korsmeyer, 1992a and Korsmeyer, 1992b). These recent findings indicate that PC12 cell death initiated by SOD1 down-regulation is dependent on generation of nitric oxide and therefore apparently on formation of peroxynitrite. The inhibition of cell loss by ICE family inhibitors suggests that free radicals-such as peroxynitrite themselves do not directly cause apoptotic death, but, more likely, that they function as signals that initiate a common death pathway.

Despite the presence of what appears to be a broadly shared final route to apoptosis, the data presented herein indicate that even this "final pathway" may show individuality, depending on the initiating causes of death. For example, significant distinctions were noted in the concentrations of ICE family inhibitors at which protection was obtained in the different paradigms presented herein. Cells were protected from SOD1 down-regulation at concentrations of V-ICE$_{inh}$ nearly an order of magnitude lower than those required to save them from trophic factor withdrawal. There was a comparable difference in the potency of ZVAD-FMK (Seq. I.D. No. 2) in the two systems. In addition, ZYVAD-CMK (Seq. I.D. No. 6) fully protected from SOD1 down-regulation while providing only partial protection from trophic deprivation, even at five-fold higher levels. For sympathetic neurons, cell death evoked by NGF deprivation was abrogated by V-ICE$_{inh}$ and ZVAD-FMK (Seq. I.D. No. 2) but was unaffected by ZYVAD-CMK (Seq. I.D. No. 6). It should be noted that ZYVAD-CMK (Seq. I.D. No. 6) would be expected to be more specific as an inhibitor of ICE, while ZVAD-CMK (Seq I.D. No. 2) may more generally inhibit ICE family proteases (Nicholson et al., 1995). These differences in the efficacy of these compounds in the two paradigms may reflect the involvement of different members of the ICE-family of proteases in each pathway, the availability of different substrates or a combination of the two.

The demonstration that the ICE family of proteases is involved in apoptosis in the models used here led to an investigation of the role of IL-1β itself. Once again differences in the "final pathway" are apparent. Both a blocking antibody to IL-1β and the naturally occurring IL-1 receptor antagonist, IL-1ra, provide almost complete protection against SOD1 down-regulation. In contrast, the blocking antibody failed to protect against trophic factor withdrawal and IL-1ra protected partially, but only at extremely high levels. Although there is an increase of IL-1β release after SOD1 down-regulation, there was no detectable change after withdrawal of trophic support. This rules out the possibility that loss of trophic support triggers a massive release of IL-1β that can be blocked only by enhanced concentrations of ICE inhibitors or that cannot be blocked by the levels of antibody or receptor antagonist that were employed. Moreover, it was noted that the largest increase in IL-1β release occurs after exposure to NGF. Because NGF prevents rather than causes death of PC12 cells deprived of trophic support, it appears that enhanced IL-1β production is not sufficient to evoke death in this system. Consistent with this, addition of 1 μg/ml rhIL-1β to PC12 cultures in the presence of NGF, insulin, or serum did not produce cell death. Therefore, apoptosis triggered by down-regulation of SOD1 does not appear due to increased secretion of IL-1β alone, but rather to an increased vulnerability to this cytokine. This could stem from a variety of mechanisms including enhanced IL-1β responsiveness. Another possible mechanism is by increased production of nitric oxide. IL-1β induces nitric oxide production in pancreatic cells. It has been shown that generation of nitric oxide enhances the death mediated by the down-regulation of SOD1, whereas nitric oxide is protective against serum-deprivation mediated apoptosis. The generation of nitric oxide by IL-1β may account for the differential effects of block of IL-1β on these systems.

Although it is tempting to exclude IL-1β as a major factor in death caused by trophic factor deprivation in the model system, another possibility cannot be ruled out. It is possible that loss of trophic support makes the cells so exquisitely sensitive to even basal levels of this interleukin that blockade can only be achieved by extremely high antibody and receptor antagonist levels.

In spite of the differences in the specifics of the final steps leading to cell death in the two paradigms tested, the data show the possibility of designing agents which could block cell loss in neurodegenerations of diverse etiology. For example, the novel inhibitor, V-ICE$_{inh}$ which was used in these experiments would be expected to inhibit all ICE family proteases by denying them access to their substrates. This differs from pseudosubstrate inhibitors such as those based on the YVAD (Seq. I.D. No. 7) or DVED (Seq. I.D. No. 8) motifs which distinguish between individual members of the ICE protease family by mimicking the cleavage site of the substrate (Nicholson et al., 1995). In additional contrast to pseudosubstrate inhibitors, V-ICE$_{inh}$ should also avoid the problem of inhibiting non-ICE cysteine proteases. Although in these experiments, a general substrate-directed inhibitor of ICE family proteases (V-ICE$_{inh}$) was purposely designed, the Antennapedia-linked vector should also be useful for facilitating internalization of pseudosubstrate ICE family inhibitors. Thus, this technology might be useful to target either all, or single members of the ICE protease family. V-ICE$_{inh}$ may therefore be viewed as a prototype of a potential new class of therapeutic agents.

The demonstration of a role for IL-1β in apoptosis induced by free radicals might have particular relevance to Alzheimer's Disease. The brains of patients dying from this disease have been reported to have elevated levels of IL-1 (Griffin et al., 1989). Several recent reports have raised the possibility that free radical generation by glycated tau (Yan et al., 1994), amyloid (Hensley et al., 1994) or both can occur in these brains. If this is the mechanism by which cell damage and loss occurs, it is likely that agents such as V-ICE$_{inh}$, which block ICE activity and anti-inflammatory agents which block IL-1 might be useful in the treatment of the disease. The latter have already been reported to show promise in preliminary clinical studies (Breitner et al., 1994; McGeer et al., 1992; and McGeer and Rogers, 1992).

EXAMPLE 2

Multiple Pathways of Neuronal Death Induced by DNA Damaging Agents, NGF Deprivation, and Superoxide Dismutase 1 Depletion Multiple Pathways of Neuronal Death.

Abstract

The pathways by which DNA damaging agents, NGF deprivation, and superoxide dismutase 1 (SOD1) depletion evoke apoptosis of cultured sympathetic neurons was studied. The hypothesis was raised that cell cycle signalling plays a required role in neuronal apoptosis elicited by both NGF deprivation and camptothecin, an agent surmised to damage DNA in neurons. To test this hypothesis, the investigation of DNA damaging agents was extended to both cytosine arabinoside (AraC) and UV irradiation. As with NGF deprivation and camptothecin treatment, the cyclin dependent kinase inhibitors flavopiridol and olomoucine protected neurons from apoptosis induced by AraC and UV treatment. These observations support the model that camptothecin, AraC, and UV treatment create double stranded breaks which lead to apoptosis by a mechanism that, as in the case of NGF deprivation, includes activation of cell cycle components. Flavopiridol and olomoucine, however, had no effect on death induced by SOD1 depletion, suggesting that cyclin dependent kinases do not play a role in this paradigm of neuronal death. To further compare the mechanisms of death evoked by NGF withdrawal, SOD1 depletion, and DNA damaging agents, their responses to inhibitors of cysteine aspartases, required elements in a variety of apoptotic pathways was investigated. The V-ICE$_{inh}$ peptide, a general inhibitor of cysteine aspartases, protected neurons in all three death paradigms. In contrast the cysteine aspartase inhibitory peptide zVAD-fmk conferred protection from NGF withdrawal and SOD1-depletion, but not DNA damaging agents, whereas acYVAD-cmk only protected from SOD-1 depletion. Taken together, these findings indicate that each of three separate apoptotic stimuli activates a unique pathway of death in the same neuron type.

Apoptosis is a tightly coordinated process of cell death which is integral to nervous system development (Oppenheim, 1991) as well as neuronal injury and disease (Boniece and Wagner, 1993; Cheng and Mattson, 1991). This death is accompanied by well characterized morphological changes including chromatin condensation, nuclear disruption and formation of apoptotic bodies (Wyllie et al., 1980) and is controlled by discreet signalling pathway(s) (Ellis et al., 1991), the orders and compositions of which appear to vary depending upon the initiating causes of death (Troy et al., 1996a; Park et al., 1997; Pronk et al., 1996).

Apoptotic death of neurons, even of the same type of neuron, can be evoked by different initiating events. One means is by loss of trophic support, a prototypic example of which is withdrawal of nerve growth factor (NGF) from cultured sympathetic neurons (Levi-Montalcini and Angeletti, 1963). A second initiating trigger for neuronal death is oxidative stress. Such death can be evoked in cultured sympathetic neurons by simultaneous exposure to NO generators and an antisense construct that depletes cellular levels of superoxide dismutase-1 (SOD1) (Troy et al, 1997). Although neither agent alone produces apoptosis, the combination causes rapid apoptotic death. Various types of evidence suggest that death in this instance (but not in the case of NGF withdrawal) is due to formation of peroxynitrite (Troy and Shelanski, 1994; Troy et al., 1996b). Exposure to DNA damaging agents represents a third means of evoking neuronal apoptosis. Although neurons are post-mitotic, a variety of DNA damaging agents, including the pyrimidine antimetabolite cytosine arabinoside (Martin et al., 1990), the topoisomerase I inhibitor camptothecin (Park et al., 1997; Morris and Geller, 1996), topoisomerase II inhibitors (Tomkins et al., 1994), and irradiation (Tomkins et al., 1994; Ferrer et al., 1993) also induce neuronal apoptosis. This occurs even in the presence of trophic factors.

The capacity of different initiating events to cause neuronal apoptotic death, even in the same type of nerve cell, raises several issues. Amongst these is the extent to which the pathways leading to apoptosis in each case are distinct and the degree to which they share and converge upon common elements. Two specific elements of neuronal apoptotic pathways will be considered here. The first is the cell cycle regulatory machinery. Multiple lines of evidence suggest that such components are involved in neuronal death evoked by loss of trophic support. Several agents that inhibit cell cycle progression, including chlorophenylthio-cyclic AMP (cAMP) (Rukenstein et al., 1991), dominant-negative Ras (Ferrari and Greene, 1994), and the G1/S blockers, mimosine, deferoxamine, and ciclopirox (Farinelli and Greene, 1996), promote survival of sympathetic neurons and/or neuronally-differentiated PC12 cells. Neuronal apoptosis is also accompanied by changes in CDK activity and cyclin expression (Brooks et al., 1993; Freeman et al., 1994; Gao and Zalenka, 1996). Consistent with this, the CDK inhibitors, flavopiridol and olomoucine, promote survival of neuronal PC12 cells and sympathetic neurons deprived of trophic support (Park et al, 1996a).

Components of the cell cycle machinery have also been suggested to play a role in neuronal death evoked by DNA damaging agents. In support of this, the CDK inhibitors flavopiridol and olomoucine, as well as several G1/S blockers were found to rescue sympathetic and cortical neurons from camptothecin-induced death (Park et al., 1997). A role for cell cycle elements in neuronal death evoked by SOD1 depletion has been less clear. The G1/S inhibitor deferoxamine blocked death of PC12 cells in which SOD1 was depleted, but did so at concentrations several orders of magnitude less than that required to affect DNA synthesis (Farinelli and Greene, 1996; Troy et al., 1996b).

Members of the cysteine aspartase (caspase) family of proteases represent a second required element for neuronal death pathways. A number of these family members, which include ICE, Nedd-2/ICH-1, and CPP32, among others, induce apoptosis in neurons as well as other cell types when overexpressed (Gagliardini et al, 1994; Miura et al., 1993; Wang et al., 1994; Kumar et al., 1994; Fernandez-Alnemri et al., 1994). With respect to trophic factor deprivation, crmA, a serpin-like inhibitor of ICE-like proteases from the pox virus, protects chicken dorsal root ganglion neurons from death induced by NGF withdrawal (Gagliardini et al., 1994; Miura et al., 1993). Furthermore, the cysteine aspartase inhibitors zVAD-fmk and V-ICE$_{inh}$ protect neuronal PC12 cells and sympathetic neurons from NGF deprivation (Troy et al., 1996a; Park et al., 1996b) as does exposure to an antisense oligonucleotide that diminishes Nedd-2 expression (Troy et al., 1997). In the case of SOD1 depletion, studies with naive PC12 cells have established that although death in this paradigm is blocked by the ICE-directed inhibitor acYVAD-cmk, the latter is ineffective in blocking death caused by trophic factor deprivation (Troy et al., 1996a). Moreover, the Nedd-2 antisense oligonucleotide that protects from NGF withdrawal does not protect PC12 cells from SOD1 depletion. Such findings have indicated that different caspases are involved in the pathways that regulate apoptosis evoked by depletion of SOD1 and NGF deprivation.

Caspase involvement in neuronal death caused by DNA damaging agents has been less clear. Although the caspase inhibitor zVAD-fmk protects sympathetic neurons from NGF withdrawal and SOD1 depletion (Park et al., 1996b; Troy et al., 1996a), it does not protect them from the DNA damaging agent camptothecin (Park et al., 1997). This not only indicates a divergence of death pathways, but also raises the general issue of whether caspases play a role in neuronal death evoked by DNA damaging agents.

The aim of the present studies has been to further test and refine the hypothesis about the pathways by which DNA damaging agents cause neuronal apoptosis and to compare this pathway of death with those invoked by SOD1 depletion and NGF deprivation. To eliminate potential cell-type-specific differences in death pathways, the examination focuses upon sympathetic neurons. As one means towards the objectives, the experiments with cultured sympathetic neurons have been extended to two additional treatments that have potential to damage DNA. One is the anti-tumour drug 1-b-arabinofuranosylcytosine (cytosine arabinoside; AraC). Although the toxic actions of AraC on dividing cells have been postulated to be due to blockade of DNA synthesis by chain termination (Ohno et al., 1988), this agent causes neuropathies and promotes death of cultured post-mitotic sympathetic neurons even in the presence of NGF (Tomkins et al., 1994; Martin et al., 1990). To account for the death-promoting actions of AraC on neurons, Martin et al. (1990) have suggested that it specifically interferes with the NGF signalling mechanism. In contrast, Tomkins et al. (1994) have proposed that AraC causes neuronal apoptosis by creating double stranded breaks in DNA. Irradiation is an additional treatment that damages DNA and it is by this means that it has been proposed to induce death of proliferating cells (Sanchez and Elledge; 1995). Various forms of irradiation also promote death of post-mitotic neurons (Tomkins et al., 1994; Ferrer et al., 1993), but by an unknown mechanism.

Herein, it is reported and demonstrated that neuronal death evoked by AraC or UV irradiation, as in the case of camptothecin treatment (Park et al., 1997) and NGF-deprivation (Park et al., 1996a), is inhibited by the CDK inhibitors flavopiridol and olomoucine, and therefore may involve cell cycle signalling components. In contrast, the same inhibitors fail to promote the survival of neurons depleted of SOD1, suggesting that CDKs do not play a role in neuronal death due to formation of excess peroxynitrite. Evidence is also provided to support the notion that death evoked by DNA damaging agents requires the actions of cysteine aspartases, but that these are distinct from those involved in apoptosis caused by withdrawal of trophic support or SOD1 depletion.

Materials and Methods

Materials.

Olomoucine (2-(2-hydroxyethylamino)-6-benzylamino-9-methylpurine) and isoolomoucine were purchased from LC® laboratories. Aphidicolin, mouse NGF, and anti-mouse NGF antiserum were obtained from Sigma® Chemical Co (St. Louis, Mo.). zVAD-fluoromethylketone (zVAD-fmk) was purchased from Enzyme Systems Products® (Dublin, Calif.). The $ICE_{inh}$ peptide (IQACRG, Chiron®; San Diego, Calif.) and ICEs peptide control (ICGRQA, Chiron®, San Diego Calif.) and ASOD1 antisense oligonucleotide were linked to the antennapedia delivery peptide (V; Oncor®) as previously described (Troy et al., 1996a).

Culture and Survival Assay of PC12 Cells.

Naive PC12 cells were cultured and passaged as previously described (Greene and Tischler, 1976). Neuronally-differentiated PC12 cells were generated by exposing PC12 cells to NGF in serum-free RPMI 1640 medium for 8–9 days. For survival experiments, neuronally-differentiated PC12 cells were plated onto collagen-coated 24-well tissue culture dishes at a density of approximately $2 \times 10_5$ cells per well. Neuronally-differentiated PC12 cells were cultured in serum-free RPMI 1640 medium containing NGF (100 ng/ml) throughout the course of survival experiments. At appropriate times of culture under the conditions described in the text, cells were lysed and the numbers of viable cells was evaluated as previously described (Rukenstein et al., 1991). All experimental points are expressed as a percentage of cells plated on day 0 and are reported as mean +/−SEM (n=3).

UV Irradiation.

Cells were exposed to UV irradiation using the Stratolinker UV crosslinker (Stratagene®). Sympathetic neurons were exposed to $3 \times 10^4$ µJ while neuronal PC12 cells were exposed to $6.5 \times 4$ µJ. Each well was exposed with 200 µl of medium containing NGF with or without the appropriate drug. After irradiation 300 µl of additional medium containing NGF with or without drug was added.

Culture and Survival Assay of Rat Sympathetic Neurons.

Primary cultures of rat sympathetic neurons were generated from dissociated superior cervical ganglia of postnatal day 1 rats (strain, Sprague-Dawley) as described previously (Lee et al., 1980). The cells were plated onto collagen-coated 24-well dishes at a density of approximately 0.5 ganglia per well and maintained in RPMI 1640 medium supplemented with 10% heat-inactivated horse serum and 60 ng/ml mouse NGF for a period of three days prior to the survival experiment. A mixture of uridine and 5-fluorodeoxyuridine (10 mM each) was also added to eliminate non-neuronal cells on day two. No pretreatment with survival agent, unless otherwise noted, was necessary for effective survival of neurons exposed to AraC. In the case of UV irradiation, the neurons died quite rapidly. Accordingly, neuronal cultures were pretreated overnight (18 hr) with survival-promoting agents prior to UV irradiation. NGF deprivation was performed by washing with NGF-free medium and addition of anti-NGF antiserum as previously described (Park et al., 1996a). V-ASOD1 oligonucleotides, in conjunction with the nitric oxide generator, S-nitrosopenicillamine (SNAP; 100 µM) were added to the cultured sympathetic neurons as previously described (Troy et al., 1997). At appropriate times, the numbers of viable, phase bright neurons were determined by strip counting as previously described (Rydel and Greene; 1988). All experimental points are expressed relative to the original number of neurons present in each well and are reported as mean+/−SEM (n=3).

Results

Figure 6B:
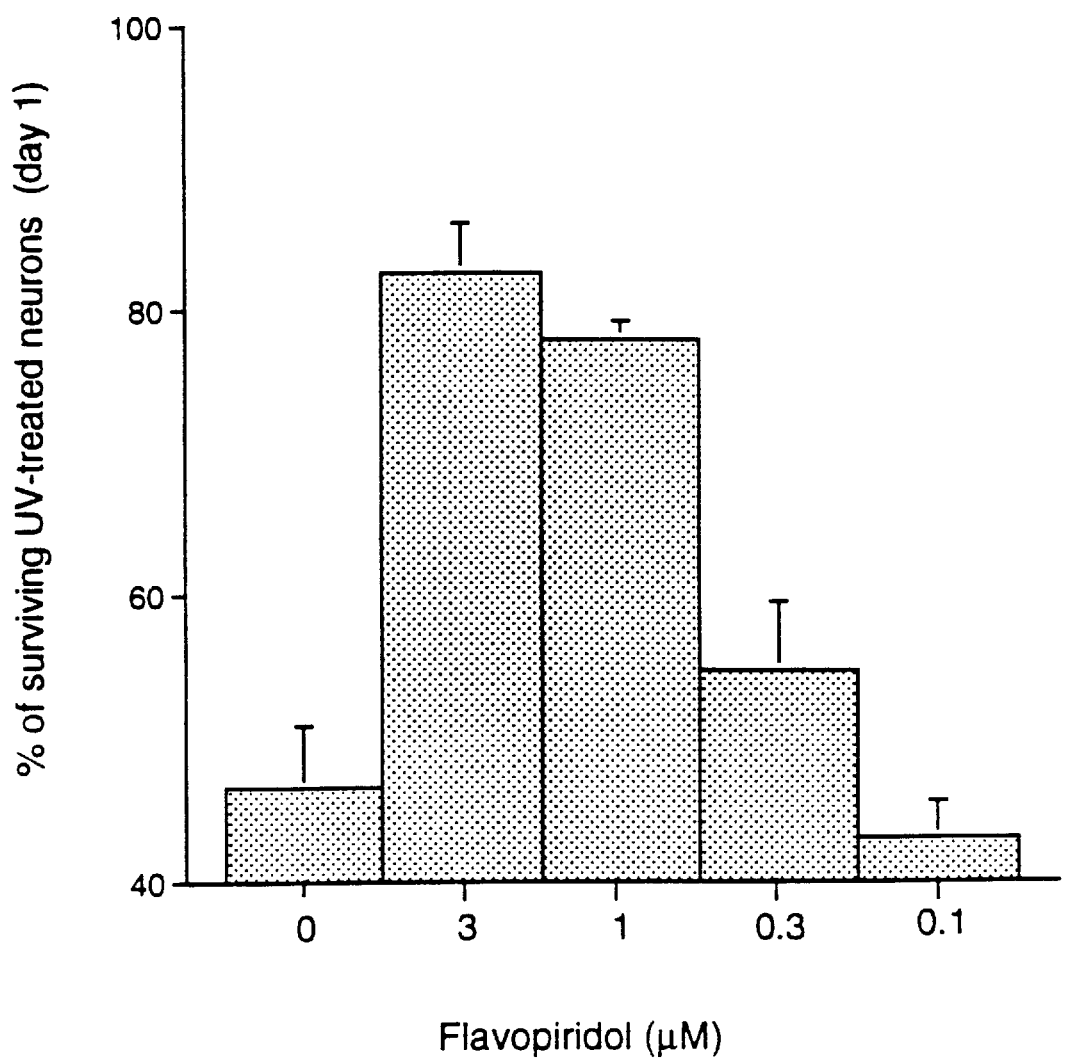
Figure 6C:
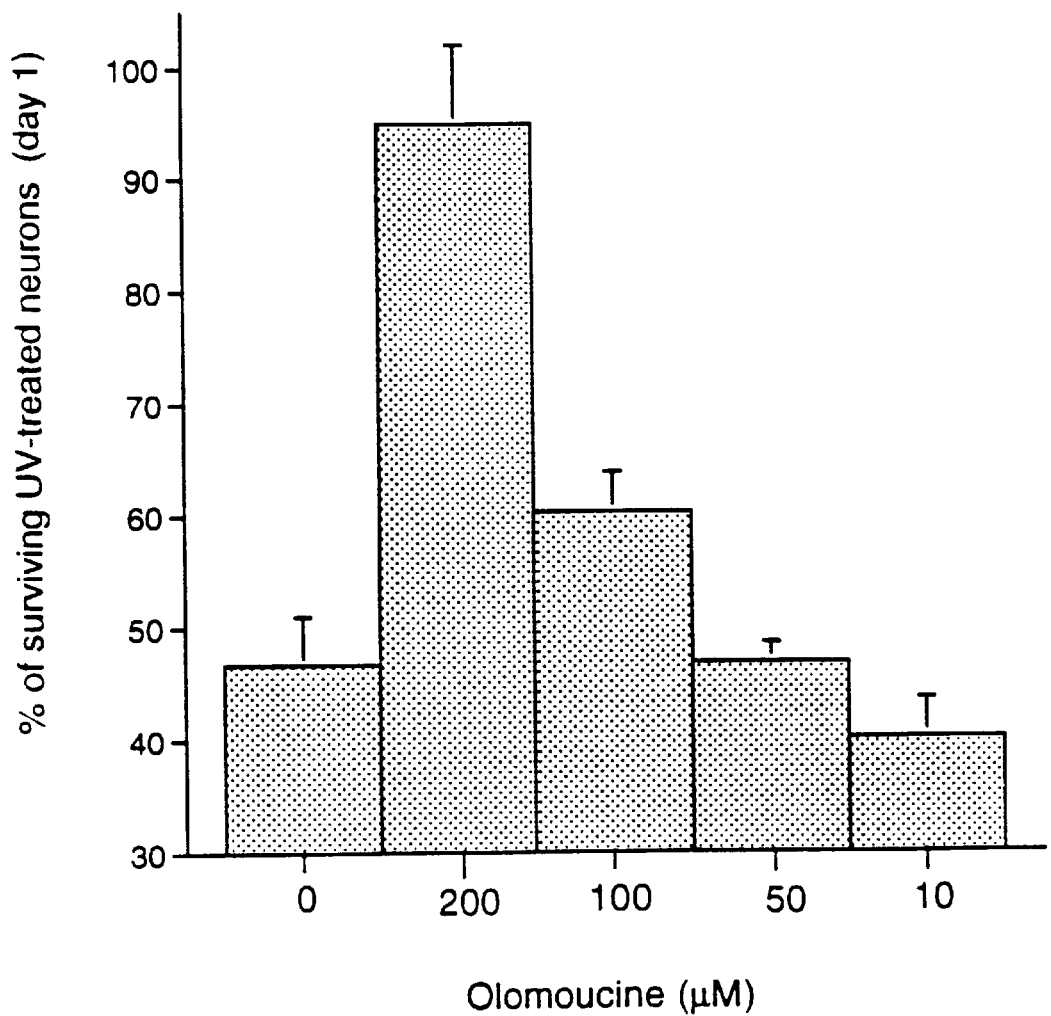

The CDK Inhibitors Flavopiridol and Olomoucine Promote Survival of Sympathetic Neurons Exposed to UV Irradiation or Treated with AraC It was demonstrated that the camptothecin-induced apoptotic death of neurons is inhibited by specific cell cycle blockers (Park et al., 1997) and it was postulated that camptothecin-induced neurotoxicity is due to transcriptionally-mediated DNA double strand break formation (Morris and Geller, 1996) and consequent cell cycle signalling components (Park et al., 1997). To assess whether this observation could be extended to other forms of DNA damaging agents, it was first determined whether the CDK-inhibitors flavopiridol and olomoucine could prevent the death of cultured sympathetic neurons exposed to UV irradiation in the presence of NGF. Flavopiridol, a flavanoid derivative, potently inhibits CDK1/2/and 4 activities (Losiewicz et al., 1994; Filgueira de Azevedo et al., 1996). Olomoucine, a purine derivative, specifically blocks cdk1/2/and 5 as well as ERK-1/MAP-kinase activities (Vesely et al., 1994). Both drugs block progression from G1 to S and G2 to M phases of the cell cycle and are ineffective in inhibiting other kinases tested (Vesely et al., 1994; Kaur et al., 1992). As shown in FIGS. 6A–E, both flavopiridol and olomoucine effectively promoted survival of UV-treated sympathetic neurons. Four days after UV treatment, approximately 75% to 80% of the neurons were alive with drug treatment, while only 25% were alive without the inhibitors. Maximal protection was observed with 1–3 µM flavopiridol (FIG. 6B) and 200 µM olomoucine (FIG. 6C). These are also the minimum concentrations required to fully inhibit DNA synthesis in proliferating PC12 cells (Park et al., 1996a). In addition, the dose-responses for protection against UV-induced death are nearly identical to those required for protection against both camptothecin treatment (Park et al., 1997) and NGF deprivation in sympathetic neuronal cultures (Park et al., 1996a).

Figure 6D:
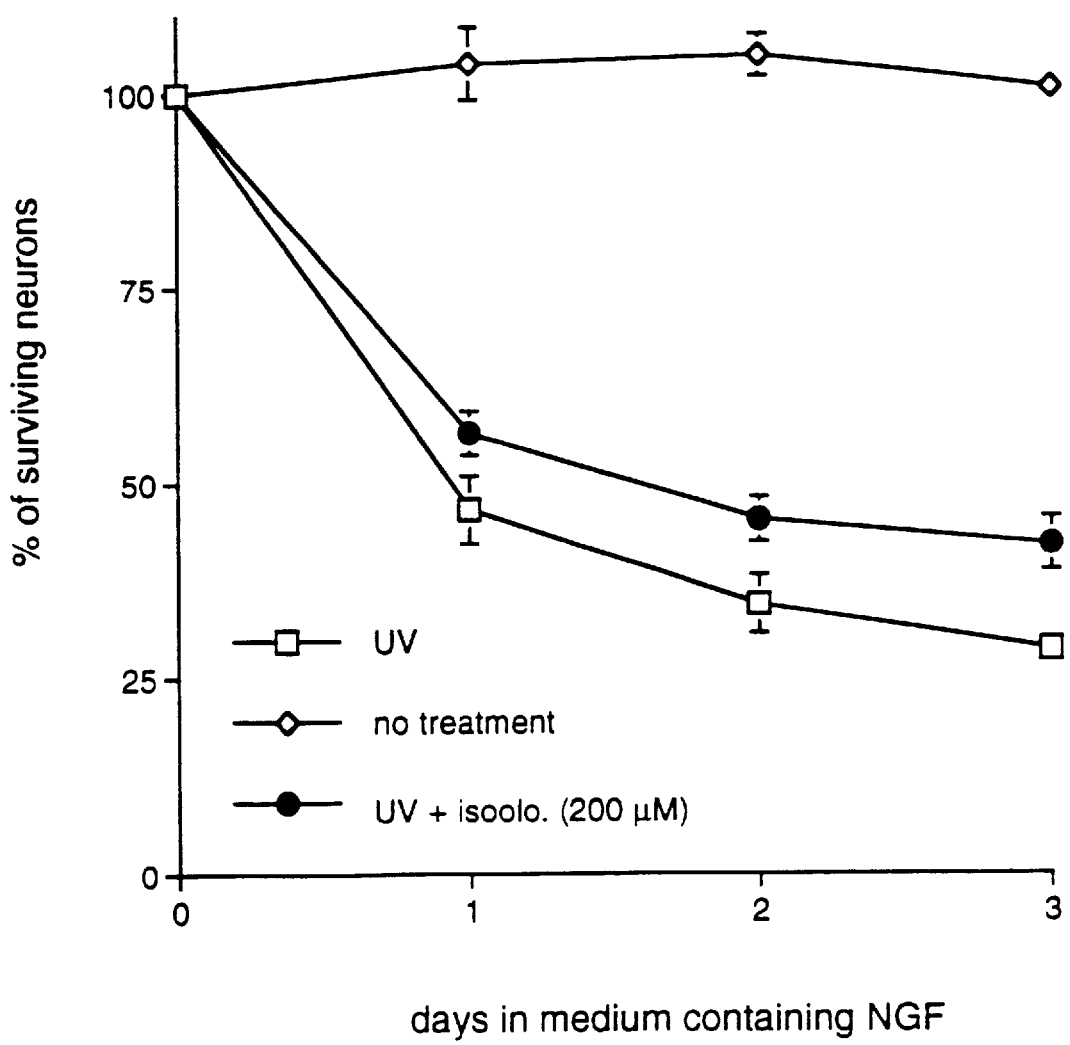
Figure 7A:
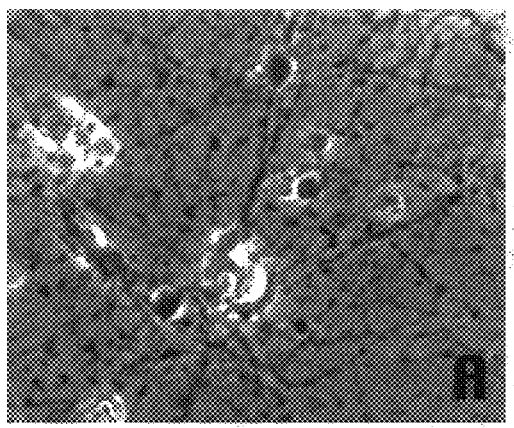
Figure 7B:
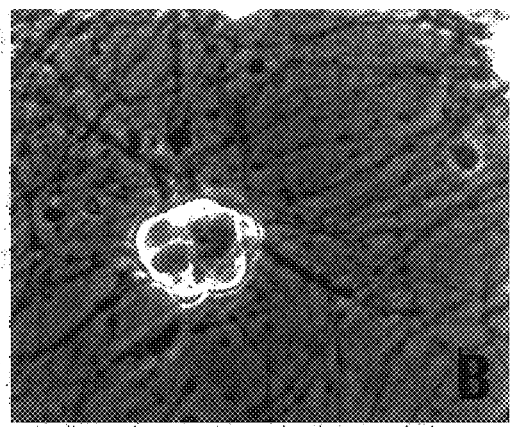
Figure 7C:
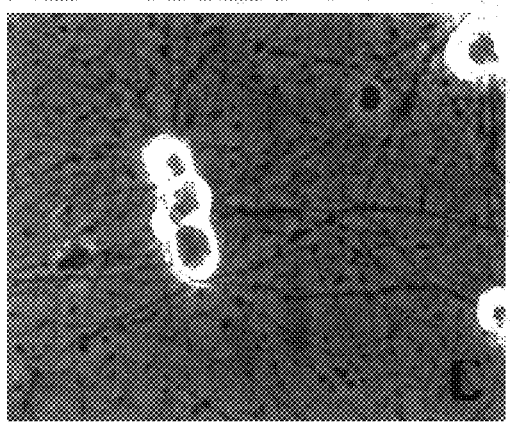
Figure 7D:
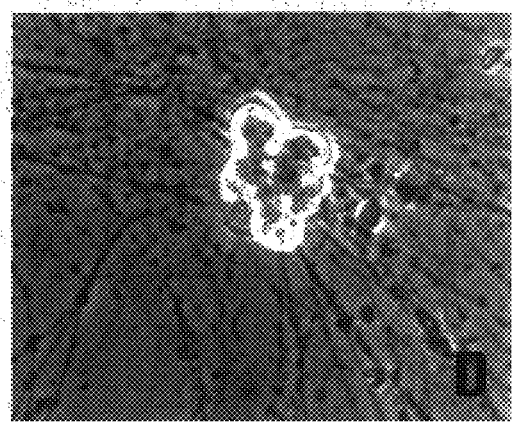

FIGS. 7A–C show the morphology of sympathetic neurons exposed to UV irradiation in the presence or absence of flavopiridol or olomoucine. Neurons treated with the CDK inhibitors show the phase bright cell bodies of viable neurons and intact neurites, while untreated cells show degenerating cell bodies and neurites. Isoolomoucine, an analogue control of olomoucine that differs in the location of one substituent methyl group and that poorly inhibits CDK activity or DNA synthesis (Park et al., 1996a), was nearly ineffective in promoting survival of UV-treated sympathetic neurons (FIG. 6D). The UV treatment experiments were extended to post-mitotic, neuronally-differentiated PC12 cells cultured in the presence of NGF, and similar survival effects were observed with olomoucine and flavopiridol.

Figure 8A:
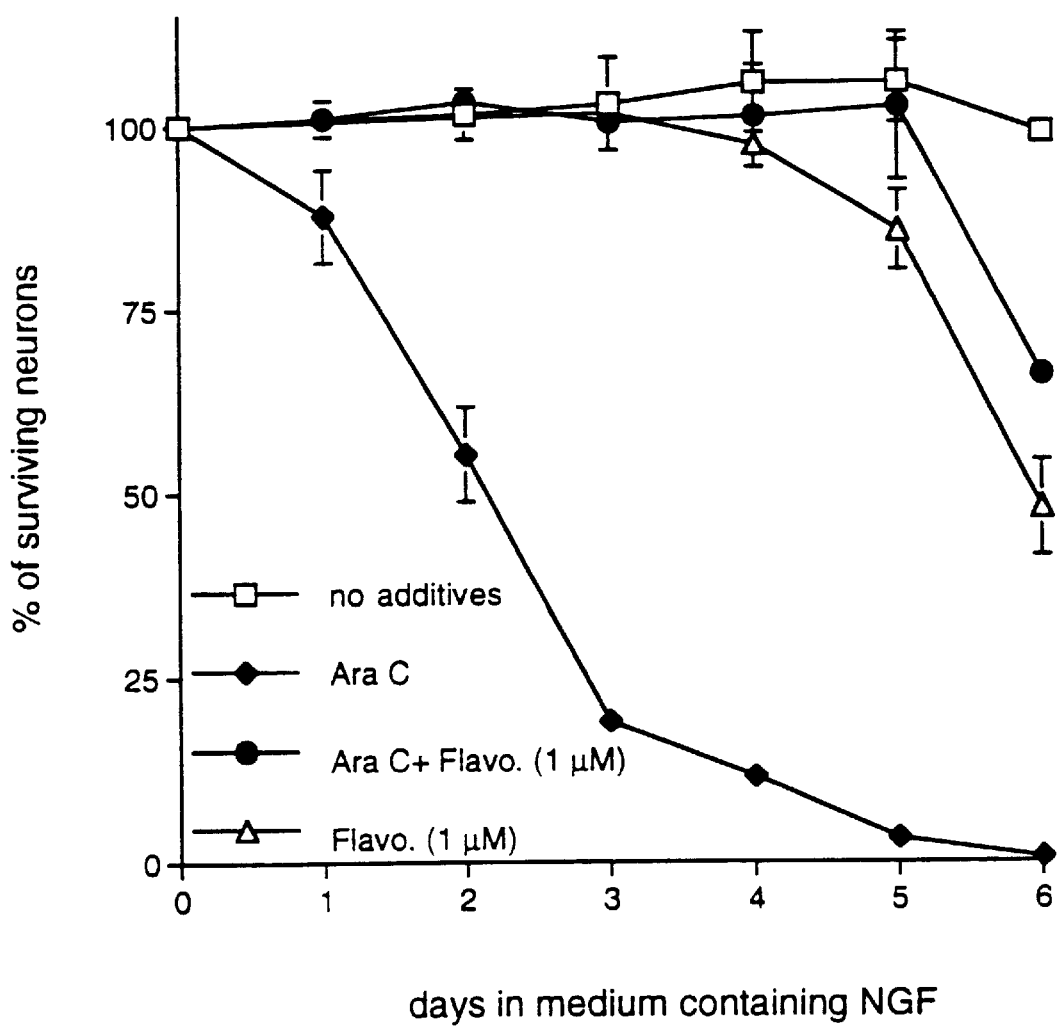
Figure 8B:
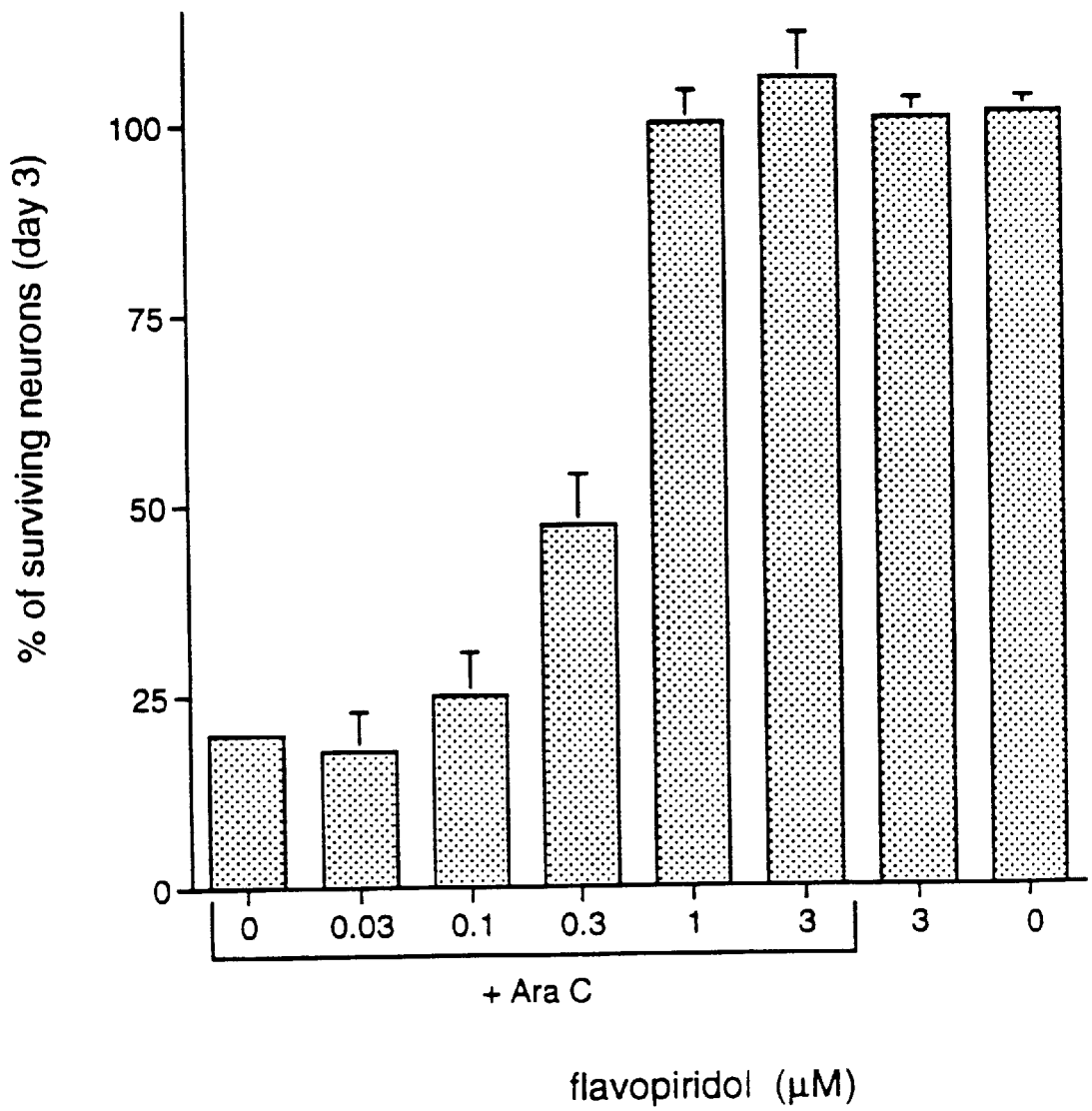
Figure 8D:
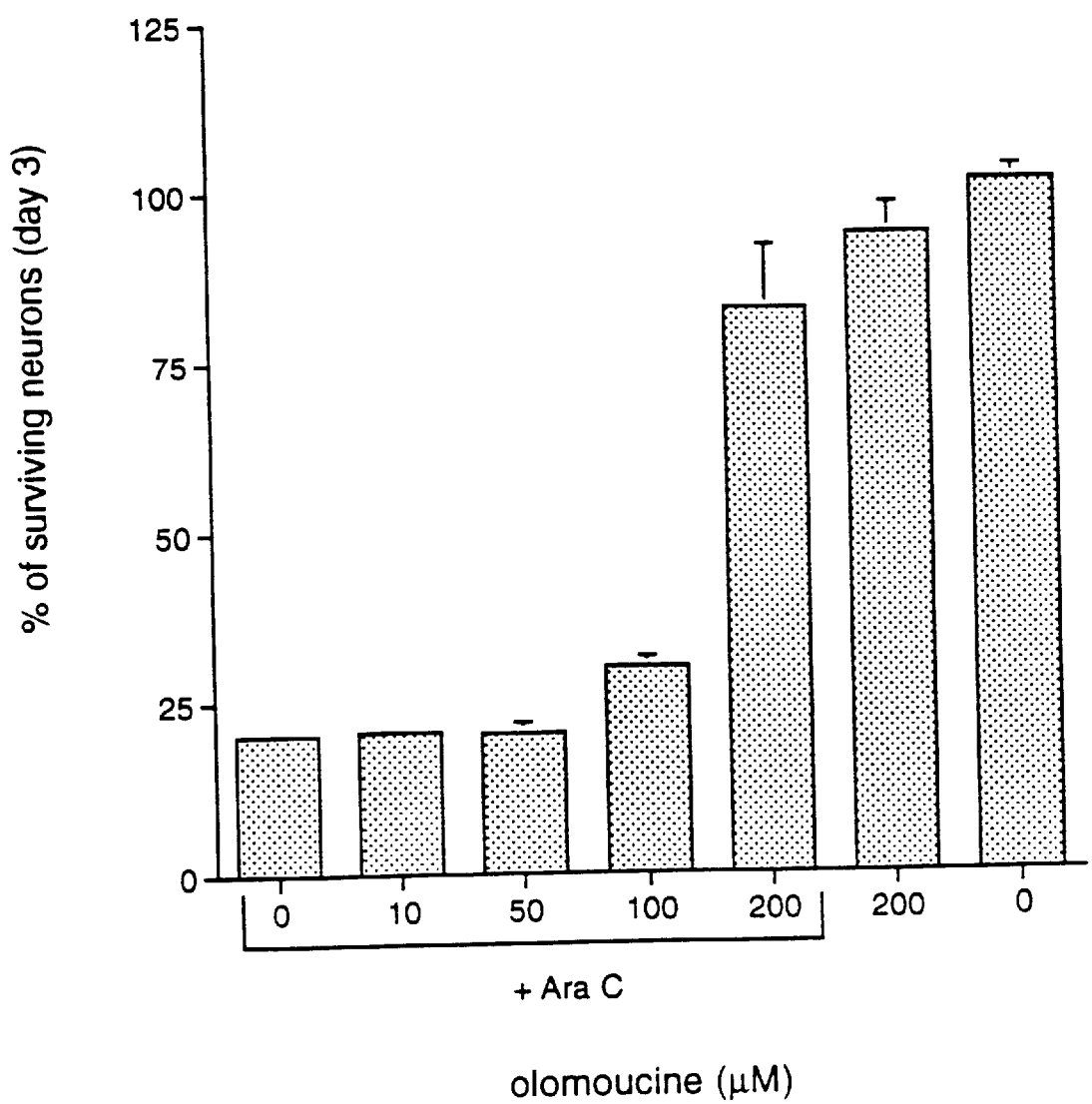

Martin et al. (1990) reported that sympathetic neurons undergo apoptosis when exposed to a sufficiently high concentration of AraC regardless of the presence of NGF, and Tomkins et al. (1994) suggested that this may be due to double stranded DNA breaks. Accordingly, it was next determined whether flavopiridol and olomoucine could also inhibit death of sympathetic neurons under these conditions. As FIGS. 8A–8E show, both drugs quite effectively promoted long term survival of AraC-treated sympathetic neurons. Approximately 80–100% of the treated neurons survived up to five days of AraC exposure while almost all of the control neurons were dead by this time. Beyond this time, toxicity of the CDK inhibitors was observed, even without AraC treatment (FIGS. 8A, 8C). As for UV irradiated sympathetic and neuronal PC12 cell cultures, the maximal concentrations of flavopiridol and olomoucine required to protect sympathetic neurons from AraC correlated with the minimum concentrations required to fully inhibit DNA synthesis by proliferating PC12 cells (1 μM for flavopiridol (FIG. 8B) and 200 μM for olomoucine (FIG. 8D). The control compound isoolomoucine was ineffective in promoting survival (FIG. 8C). Neurons treated with AraC and the CDK inhibitors showed the phase-bright morphology of viable neurite-bearing cells while cells treated with AraC form ghost-like cell bodies and degenerating processes (FIGS. 9A–9C). These results along with those made previously (Park et al., 1997) demonstrate that neuronal apoptosis induced by three different forms of DNA damaging conditions, UV irradiation, camptothecin and AraC treatment, are effectively blocked by inhibitors of CDK activity.

Figure 8E:
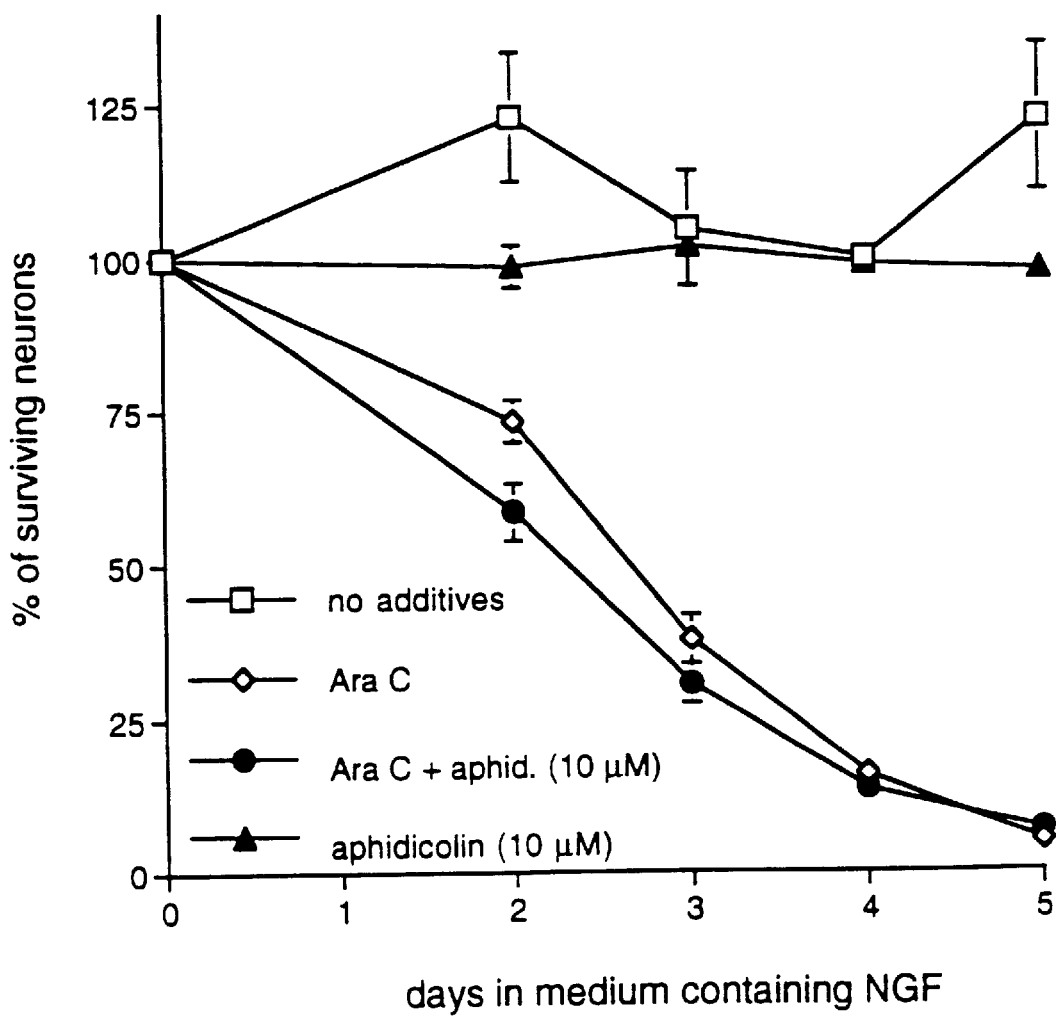

The S-phase Blocker Aphidicolin does not Promote Survival of Sympathetic Neurons Exposed to UV Irradiation or AraC It was demonstrated that neurons deprived of NGF or exposed to camptothecin cannot be rescued by cell cycle blocking agents that act beyond the G1/S border (Park et al., 1997; Farinelli and Greene, 1996). For example, the S-phase blocker, aphidicolin, is ineffective in blocking death of sympathetic neurons in both paradigms (Park et al., 1997; Farinelli and Greene, 1996). Consistent with this, aphidicolin also failed to block death of neurons exposed to either UV irradiation (FIG. 6E) or AraC (FIG. 8E). Such findings demonstrate that the neuronal death induced by UV, AraC, camptothecin, or NGF deprivation does not depend on DNA synthesis per se. In addition, they suggest that a cell cycle check point exists at the early G1/S border, beyond which rescue from death is not possible.

The CDK Inhibitors Flavopiridol and Olomoucine do not Promote Survival of Sympathetic Neurons Exposed to Oxidative Stress Evoked by Depletion of SOD1

Sympathetic neurons depleted of SOD1 by treatment with an SOD1 antisense oligonucleotide and exposed to nitric oxide generating compounds die apoptotically, presumably due to formation of peroxynitrite (Troy et al., 1996b; Troy et al., 1997). It was examined whether the CDK inhibitors would block death of neurons induced by this means. As shown in FIGS. 8A–E, neither flavopiridol nor olomoucine protected sympathetic neurons in this paradigm. However, in the same experiments both inhibitors effectively blocked the death of sympathetic neurons deprived of NGF. This suggests that cell cycle regulatory components do not control the neuronal death pathways induced by oxidative stress. The CDK inhibitors also failed to inhibit death of neuronal PC12 cells depleted of SOD1.

Differential Effects of Cysteine Aspartame Inhibitors on Sympathetic Neurons Deprived of NGF, Depleted of SOD1 or Exposed to DNA Damaging Agents It was next examined whether the cysteine-aspartase inhibitor zVAD-fmk protects sympathetic neurons from death evoked by DNA damaging agents and SOD1 depletion. Treatment with 50 μM zVAD-fmk protected sympathetic neurons depleted of SOD1 and exposed to nitric oxide generators (FIGS. 11A–C). It was found that the same concentration of caspase inhibitor protected PC12 cells from death evoked by SOD1 depletion (Troy et al., 1996a). In contrast, zVAD-fmk was ineffective in promoting survival of sympathetic cultures exposed to UV irradiation (FIG. 11A) or AraC (FIG. 11B). Similar results were reported for camptothecin (Park et al., 1997). As a positive control, it was shown that zVAD-fmk protects sympathetic neurons from death due to NGF-depletion (FIG. 11A)(Troy et al., 1996a; Park et al., 1997). These observations indicate a distinction between the pathways by which DNA damaging agents evoke death and by which oxidative stress and NGF deprivation do so. A study showed that sensitivity to the peptide acYVAD-cmk, a more specific inhibitor of ICE-like proteases than zVAD-fmk, blocks death of naive PC12 cells caused by SOD1 depletion but has no effect in the trophic factor deprivation paradigm (Troy et al., 1996a). FIG. 11C shows that acYVAD-cmk shows similar selectivity between these two causes of death in sympathetic neurons. Thus, cysteine protease inhibitors distinguish between each of the three causes of sympathetic neuron death studied here.

The question was then raised as to whether any cysteine aspartase is required for death induced by DNA damaging agents. To examine this issue, the general cysteine aspartase inhibitor, $ICE_{inh}$, was utilized linked to the antennapedia vector peptide (V). $ICE_{inh}$ is a peptide (IQACRG) that mimics the conserved active site of ICE-family proteases, thereby apparently binding to their substrates and preventing their cleavage (Troy et al., 1996a). Because nearly all known cysteine aspartases possess this conserved sequence, it is expected that $ICE_{inh}$ is a general inhibitor of this family. The antennapedia peptide rapidly crosses plasma membranes and functions as a vector to facilitate cellular uptake of the $ICE_{inh}$ peptide. The two peptides are linked by a reducible s—s bond, and V-ICE inh is cleaved within cells, releasing free ICEinh (Troy et al., 1996a). It was demonstrated that the antennapedia-linked peptide (V-$ICE_{inh}$) blocks death of sympathetic neurons deprived of trophic support and PC12 cells depleted of SOD1 (Troy et al., 1996a). As shown in FIGS. 12A–C, V-$ICE_{inh}$ protected sympathetic neurons from NGF deprivation. FIGS. 12A–C further shows that treatment with V-$ICE_{inh}$ also blocked death of sympathetic neurons exposed to UV (approximately 80% survival with the inhibitor vs. 25% without V-$ICE_{inh}$ treatment) and of AraC-treated sympathetic neurons (approximately 90% survival with V-$ICE_{inh}$ vs. 50% without inhibitor treatment on day 2). V-$ICE_{inh}$ additionally blocked death of sympathetic neurons either exposed to camptothecin or depleted of SOD1. A scrambled peptide (ICGRQA) linked to antennapedia (termed V-ICEs) was utilized as a control for non-specific effects and was ineffective in promoting survival of neurons in all four paradigms of death. Taken together, these data indicate that the death pathways evoked by DNA damaging agents requires cysteine aspartase(s), but that these are different from those that act in the pathay triggered by NGF deprivation and SOD1 depletion.

Discussion

In the present studies, the signalling pathways by which DNA damaging agents cause death of post-mitotic neurons were explored and compared such mechanisms with those involved in neuronal apoptosis caused by loss of neurotrophic support and oxidative stress.

Involvement of Cell Cycle Signals in Neuronal Death Due to DNA Damaging Agents

The studies considered three conditions that damage DNA and trigger apoptotic death: UV irradiation, camptothecin and AraC treatment. UV irradiation produces direct DNA damage that is mediated primarily by formation of pyrimidine dimers (Schreiber et al., 1995). This is likely to be the case for both proliferating cells and post-mitotic cells such as neurons. Camptothecin binds to and inhibits topoisomerase I, forming a cleaveable complex consisting of topo-I covalently linked to the severed DNA strand (Hsiang et al., 1989). For cycling cells, DNA double strand breaks are created as the replication fork collides with this complex during DNA synthesis. In postmitotic neurons, it is postulated that the transcription machinery can act in a similar manner resulting in a lethal DNA lesion (Morris and Geller;

1996). The chain-terminating nucleoside, AraC, which selectively kills proliferating cells in S-phase by inhibiting DNA synthesis, also kills postmitotic neurons. However, the mechanism of AraC neurotoxicity currently remains unclear. Martin et al. (1990) suggested that AraC-induced death of sympathetic neurons was due to inhibition of a deoxycytidine-dependent phase of the NGF signaling pathway. However, NGF-induced c-fos expression is not affected by AraC treatment (1994) suggesting that AraC does not interfere with all aspects of NGF signaling. Tomkins et al. (1994) have suggested that AraC-induced death of sympathetic neurons could be due to either inhibition of topo-II-mediated DNA repair or inhibition of DNA ligase, both of which would lead to the persistent formation of DNA strand breaks. They also observed that teniposide and mitoxanthrone, agents that bind to topo-II and induced DNA double-strand break formation, also kill neurons by an apoptotic mechanism.

How might DNA damage lead to neuronal death? At least for proliferating cells, a growing body of evidence suggests the involvement of cell cycle-related components. For instance, the cell cycle-related tumor suppressor protein p53 appears to mediate the responses of many cell types to UV-evoked DNA damage (Sanchez and Elledge, 1995). For proliferating cells exposed to UV irradiation, p53 functions at a cell cycle "check point" at which the cells either undergo DNA repair or death. It appears that p53 expression is also required for AraC-evoked death of neurons (Enokido et al., 1996). Of additional relevance, UV irradiation induces transcription factors such as c-jun, which is often associated with stimulation of cell cycle progression as well as apoptosis (Gillardon et al., 1994). Furthermore, AraC treatment has been reported to increase cyclin E-associated cdk activities in HL 60 cells (Ping Dou et al., 1995) while camptothecin upregulates cdc2 (Shimizu et al., 1995) and cyclin D1 (Chen et al., 1995) levels in HL60 and RKO cells, respectively.

The hypothesis that components of the cell cycle machinery contribute to the death of post-mitotic neurons caused by loss of trophic support has found support (Ferrari and Greene, 1994; Farinelli and Greene, 1996; Park et al., 1996a). For instance, a number of cell cycle blockers that act prior to the G1/S border inhibit the apoptotic death of sympathetic neurons and neuronally-differentiated PC12 cells deprived of NGF (Farinelli et al., 1996; Park et al., 1996a). These observations, along with those suggesting cell cycle involvement of DNA damage-induced death of proliferating cells, led us to propose that neuronal death evoked by DNA damaging agents also involves inappropriately regulated cell cycle components. To test this, it was examined whether cell cycle blockers promote survival of neurons exposed to DNA damaging conditions. In an initial study, it was found that death of neurons caused by camptothecin is suppressed by certain G1/S cell cycle blockers and by the CDK inhibitors olomoucine and flavopiridol (Park et al., 1997).

Presently, the investigations have been extended to include UV irradiation and AraC treatment. It was found that flavopiridol and olomoucine effectively suppress neuronal death caused by these two treatments. Moreover, as with camptothecin, the concentrations of CDK inhibitors required to block death correlate well with the levels of the drugs required to inhibit DNA synthesis in proliferating PC12 cells. The findings extend to two additional treatments that are quite distinct from one another and from camptothecin with respect to initial mechanism, but that also have the capacity to cause double stranded DNA breaks. Such observations support the proposals 1) that double stranded DNA breaks are a common element in the pathways by which these treatments cause neuronal apoptosis and 2) that death in each instance involves disregulated elements of the cell cycle machinery. For all three DNA damaging agents, aphidicolin, which blocks S-phase by inhibiting DNA polymerase a, was ineffective in providing protection. This suggests that inhibition of the cell cycle per se is not sufficient to promote survival and that there is a checkpoint prior to the G1/S border beyond which neurons are irreversibly committed to death.

The finding point to CDK's and their cognate cyclins as elements in the neuronal apoptotic pathways triggered by DNA damaging agents as well as by trophic factor withdrawal. This is consistent with prior findings with proliferating cells as well as neurons. For instance, a variety of agents that induce apoptosis of cycling cells also upregulate cyclin A-associated CDK activity (Meikrantz et al., 1994). Furthermore, expression of dominant-negative mutants of cdk1, 2, and 3 block apoptotic death of HELA cells brought about by staurosporine and tumor necrosis factor a (Meikrantz et al., 1996). Following NGF deprivation, increases in cdc2 activity and cyclin B expression (Gao and Zalenka., 1995) as well as in cyclin D1 transcript levels (Freeman et al, 1994) have been reported for neuronally-differentiated PC12 cells and sympathetic neurons, respectively. In another set of studies, differentiated neuroblastoma cells were reported to require the CDK inhibitor p21cip/waf1 (Kranenburg et al., 1996) for survival while the CDK inhibitor p16ink4 (Poluha et al., 1996) protected neuroblastoma cells from death caused by trophic factor deprivation.

The findings with olomoucine and flavopiridol suggest the involvement of CDKs in the pathway by which DNA damaging agents lead to neuronal apoptosis, alternative interpretations must be considered. In particular, the possibility that flavopiridol and olomoucine act on required elements in death signalling other than CDK's cannot be ruled out. Effects of these drugs on JNK activity or activation have been eliminated (Park et al., 1996a) which appear to be required for death of NGF-deprived neuronally-differentiated PC12 cells (Xia et al., 1996). Although all the findings to date have pointed to the highly selective nature of these CDK inhibitors, it remains possible they affect kinases yet to be examined.

CDK Inhibitors do not Protect Neurons from SOD1 Depletion

Depletion of SOD1 in the case of PC12 cells, and SOD1 depletion combined with exposure to NO generators in the case of sympathetic neurons, leads to apoptotic death by what appears to be a peroxynitrite-dependent mechanism (Troy et al., 1996b). Evidence has been presented for the role of peroxynitrite in neurodegenerative disorders and so the mechanism by which this agent results in apoptosis is of both basic and clinical relevance (Coyle and Puttfarcken, 1993). Since peroxynitrite can lead to cellular DNA damage, the possibility that, like DNA damaging agents, it might evoke death by a mechanism dependent on cell cycle regulatory components was considered. However, in contrast to observations with NGF deprivation and DNA damaging agents, death in the SOD1 depletion paradigm was insensitive to flavopiridol and olomoucine. This suggests that cell cycle components do not regulate death of sympathetic neurons in all paradigms of neuronal death.

Different Cysteine Aspartases Mediate the Death of Neurons Either Deprived of NGF, Depleted of SOD1, or Exposed to DNA Damaging Conditions.

Although the findings suggest that CDK activity may mediate some part of the apoptotic signalling response in the case of trophic factor deprivation and DNA damage, it is not clear whether these two apoptotic stimuli activate similar signalling pathways or if the nature/consequence of the cell cycle signals may differ. In addition, a notable feature of the experiments was that AraC, UV irradiation, and camptothecin each evoked apoptosis in the presence of NGF.

Accordingly, an alternative interpretation, as has been suggested for AraC (Martin et al., 1990), is that all or some of the apoptosis-evoking conditions that were employed work by blocking the signalling pathway by which NGF promotes survival. To address these issues, it was examined whether death of sympathetic neurons caused by different stimuli can be blocked by inhibitors of cysteine aspartases. zVAD-fmk, a broadly acting, but not universal inhibitor of cysteine aspartases, blocked death evoked by NGF deprivation and SOD1 depletion, but not by AraC or UV irradiation. There are similar findings for camptothecin (Park et al., 1997). In addition, it was shown herein that NGF deprivation and SOD1 depletion in sympathetic neurons, as in PC12 cells (Troy et al., 1996a), also differ in their response to caspase inhibitors. acYVAD-cmk, an inhibitor more specific to the ICE-like caspases, blocks death evoked by SOD1 depletion but not death due to NGF deprivation. These observations indicate that the death pathways triggered by NGF deprivation, SOD1 depletion, and DNA-damaging agents are distinct from one another. They also rule out the action of DNA damaging agents, including AraC, as inhibitors of proximal elements of the NGF signalling mechanism.

The observations with zVAD-fmk raise the possibility that death evoked by DNA damaging agents does not depend on cysteine aspartases. Alternatively, death elicited by NGF withdrawal and DNA damaging agents might involve different members of the cysteine protease family which in the case of DNA damaging agents is insensitive to zVAD-fmk. To address these possibilities, the peptide inhibitor, V-ICE$_{inh}$, was employed which mimics the active site of almost all known cysteine aspartase family members and which should function as a general inhibitor of these enzymes (Troy et al., 1996). This inhibitor suppresses death of sympathetic neurons evoked by NGF withdrawal and by downregulation of SOD1. It was found that V-ICE$_{inh}$ also suppresses death evoked by all three DNA damaging agents. Taken together, these data indicate that apoptosis caused by DNA damaging agents is dependent on one or more cysteine aspartase family members, and that the identity of this/these is different from the family member(s) that mediate apoptosis caused by NGF withdrawal and SOD-1 depletion.

The identity of the cysteine aspartase(s) required for neuronal death due to DNA damaging agents is presently unknown. Cysteine aspartases that mediate death of PC12 cells were compared with sympathetic neurons caused by either NGF deprivation or down-regulation of SOD1 (Troy et al., 1996). Although death in both cases was inhibited by V-ICE inh and zVAD-fmk, antisense oligonucleotides to Nedd-2 rescued PC12 cells and sympathetic neurons from withdrawal of NGF, but not from SOD1 downregulation (Troy et al., 1996; Troy et al., 1997). Conversely, acYVAD-cmk as well as blocking antibodies to mature IL-1 b and an IL-1 receptor antagonist were reported to protect PC12 cells from SOD1 depletion, but not NGF withdrawal (Troy et al., 1996a). The experiments extend the observations with acYVAD-cmk to sympathetic neurons and thus lend further support to the model that distinct caspase-dependent pathways mediate neuronal apoptosis evoked by NGF withdrawal (Nedd-2 dependent) and SOD1 depletion (ICE-like dependent). Thus, even in the same neuron type, at least three different apoptotic pathways can be activated depending on the initiating stimulus of death. The properties of these pathways are summarized in FIG. 13.

The distinction between the cysteine proteases required for death evoked by NGF deprivation and DNA damaging agents was somewhat surprising. Recent work in the PC12 cell system indicates that although cysteine protease inhibitors do not affect proliferation, antimitotic agents that suppress death inhibit induction of cysteine protease activity (Stefanis et al., 1996). This indicates that the cell cycle-related events involved in apoptosis are upstream of cysteine protease activation. Given that olomoucine and flavopiridol block death evoked by both NGF deprivation and DNA damaging agents in the same cell type (Park et al., 1996a; Park et al., 1997), one of the expectations might have been that similar cell cycle-related machinery is involved in death in both cases and that this would lead to activation of the same cysteine aspartases. The evidence presented herein that different cysteine aspartases mediate the two causes of death, however, suggests the converse, namely that the cell cycle-related components involved in death initiated by NGF deprivation and DNA damaging agents may not be identical to one another. It is interesting to note that death of neurons due to NGF deprivation is p53 independent (Martinou et al., 1995) while that for DNA damage is dependent on p53 (Enokido et al., 1996). This observation, may serve as one possible explanation of the differential caspase activation reported here.

REFERENCES

Adams, M. D. et al., (1995) Nature 377, 3–17.
Baron et al., (1982) Cell 28, 395–404.
Batistatou, A. & Greene, L. A. (1991) J. Cell Biol. 115,
Batistatou, A., Merry, D. E., Korsmeyer, S. J. & Greene, L. A. (1993) J. Neurosci. 13, 4422–4428.
Blondelle, S. E. et al., (1994) Antimicrobial Agents and Chemotherapy 38, 2280–2286.
Bock, M. G. et al., (1992) Journal of Controlled Release 21, 73–80.
Boniece, I. R., and J. A. Wagner. 1993. J. Neurosci. 13:4220–4228.
Boudreau, N., Sympson, C. J., Werb, Z. & Bissell, M. J. (1995) Science 267, 891–893.
Breitner, J. C. S., Gau, B. A., Welsh, K. A., Plassman, B. L., McDonald, W. M., Helms, M. J. & Anthony, J. C. (1994) Neurology. 44, 227–232.
Brooks, S. F., Gibson, L. A., and L. L. Rubin. 1993.Soc. Neurosci. 1:885.
Chen, X., Bargonetti, J., and C. Prives. 1995. Cancer Res. 55:4257–4263.
Cheng, B., and M. P. Mattson. 1991. Neuron 7:1031–1041
Coyle, J. T. & Puttfarcken, p. (1993) Science 262, 689–695.
Dressman et al., (1982) Nature 295, 185–160.
Ellis, R. E., Yuan, J., and H. R. Horvitz. 1991.Annu. Rev. Cell Bio. 7:663–698.
Enokido, Y., Araki, T., Aizawa, S., and H. Hatanaka. 1996.Neurosci. Letters 203:1–4.
Enari, M., Hug, H. & Nagata, S. (1995) Nature 375, 78–81.
Farinelli, S. E., Joyce, M. P. & Greene, L. A. (1995) Soc. for Neurosci.21, 1787.
Fernandes-Alnemri, T., Litwack, G. & Alnemri, E. S. (1994) J. Bid. Chem. 269, 30761–30764.
Ferrari, G. & Greene, L. A. (1994) EMBO J. 13, 5922–5928. 461–471.
Ferrari G., Yan C. Y. I. & Greene, L. A. (1995) J. Neurosci. 15, 2857–2866.
Farinelli, S.E., and L.A. Greene. 1996. J. Neurosci 16:1150–1162.
Ferrari, G., and L. A. Greene. 1994.EMBO J. 13:5922–5928.
Ferrer, I., Serrano, T., Alcantara, S., Tortosa, A., and F. Graus. 1993. J. Neuropath. Exp. Res. 52:370–378.
Filgueira de Azevedo, W., Mueller-Dieckmann, H-J., Schulze-Gahrnen, U., Worland, P. J., Sausville, E., and S-H. Kim. 1996. Proc. Natl. Acad. Sci. USA 93:2735–2740.
Freeman, R. F., Estus S., and E. M. Johnson Jr. 1994. Neuron 12:343–355.
Gao, C. Y., and P. S. Zalerika. 1995 Exp. Cell. Res 219:612–618.

Gillardon, F., Eschenfelder, C., Uhlman, E., Hartschuh, W., and M. Zimmermann. 1994.Oncogene, 9:3219–3225.

Gagliardini, V., Fernandez, P–A., Lee, R. K. K., Drexler, H. C. A., Rotello, R. J., Fishman, M. C. & Yuan, J. (1994) Science 263, 826–828.

Griffin, W. S. T., Stanley, L. C. & Ling, C. (1989) Proc. Natl. Acad. Sci. USA 86, 7611–7615.

Greene, L. A. & Tischler, A. S. (1976) Proc. Natl. Acad. Sci. U.S.A. 73, 2424–2428.

Hengartner, M. O., Ellis, R. E. & Horvitz, H. R. (1992) Nature 356, 494–499.

Hensley, K., Carney, J. M., Mattson, M. P., Aksenova, M., Harris, M., Wu, J. F., Floyd, R. A. and Butterfield, D. A. (1994) Proc. Natl. Acad. Sci. USA 91, 3270–3274.

Hsiang, Y. H., Lihou, M. G., and L. F. Liu. 1989. Cancer Res. 49:5077–5082.

Kaiser et al. (1984) Science 223 249–255.

Kaur, G., Stetler-Stevenson, M., Sebers, S., Worland, P., Sedlacek,H., Myers, C., Czech, J., Naik, R., and E. Sausville. 1992. J. Natl. Cancer Inst. 22:1736–1740.

Kempf et al. (1991) Intl. J. Peptide and Prot. Res. 38, 237–241.

Korsmeyer S. J. (1992a) Immunol. Today. 13:285–288.

Korsmeyer S. J. (1992b) Blood. 80:879–886.

Kranenburg, 0., van der Eb, A. J., and A. Zantema. 1996. EMBO 15:46–54.

Kuida, K., Lippke, J. A., Ku, G., Harding, M. W., Livingston, D. J., Su, M. S.-S. & Flavell, R. A. (1995) Science 267, 2000–2003.

Kumar, S., Knioshita, M., Noda, M., Copeland, N. G. & Jenkins, N. A. (1994) Genes & Develop. 8, 1613–1626.

Laemmli, U. K. (1970) Nature 227, 680–685.

Lazebnik, Y. A., Kaufmann, S. H., Desnoyers, S., Poiriers, G. G. & Earnshaw, W. C. (1994) Nature 371, 346–347.

Lee, J. Barrett, R. E. and Bovy, P. R. (1995) Letters in Peptide Science 2, 253–258.

Lee, V. M., Shelanski,, M. L., and L. A. Greene. 1980. Neuroscience 5:2239–2245.

Levi-Montalcini R., and Angeletti P. U. 1963. Dev. Biol. 7:653–657.

Lerner, (1983) Scientific American 248, 66–74.

Los, M., Van de Craen, M., Penning, L. C., Shenk H., Westendorp, M., Baeuerle, P. A., Droge, W., Krammer, P. H., Fiers, W. & Schulze-Osthoff, K. (1995) Nature 375, 81–83.

Losiewitz, M. D., Carlson, B. A., Kaur, G., Sausville, E. A., and

P.J. Worland. 1994. Biochem. Biophy. Res. Comm. 201:589–595.

Lerner et al., Cell 23, 309–310 (1981);

Martin, D. P., Wallace, T. L., and E. M. Johnson Jr. 1990. J. Cell Biol. 10:184–193.

Martinou, I., Fernandez, P. A., Missotten, M., White, E., Allet, B., Sadoul, R., and J. C. Martinou. 1995. J. Cell Bio. 128:201–208.

Meikrantz, W., Gisselbrecht, S., Tam, S. W., and R. Schlegel. 1994. Proc. Natl. Acad. Sci. 91:3754–3758.

Meikrantz, W., and R. Schlegel. 1996. J. Biol.Chem. 271:10205–10209.

Morris, E. J., and H. M. Geller. 1996. J. Cell Biol. 134:757–770.

McGeer, P. L., McGeer, E., Rogers, J. & Sibley, J. (1992) Lancet 335, 1037.

McGeer, P. L. & Rogers, J. (1992) Neurology 42, 447–449.

Ankarcrona, M., Dypbukt, J. M., Brune, B & Nicotera, P. (1994) Exp. Cell Res. 213, 172–177.

Milligan, C. E., Prevette, D., Yaginuma, H., Homma, S., Cardwell, C., Fritz, L. C., Tomaselli, K. J., Oppenheim, R. W. & Schwartz, L. M. (1995) Neuron 15, 385–393.

Miura, M., Zhu, H., Rotello, R., Hartweig, E. A. & Yuan, J. (1994) Cell 75, 653–660.

Nicholson, D. W., Au, A., Thornberry, N. A., Vaillancourt, J. P., Ding, C. K., Gallant, M., Gareau, Y., Griffin, P. R., Labelle, M., Lazabnik, Y., Munday, N. A., Raju, S. M., Smulson, M. E., Yamin, T.-T., Yu, V. L. & Miller, D. K. (1995) Nature 376, 37–43.

Ohno, Y., Spriggs, D., Matsukage, A., Ohno, T., and D. Kufe. 1988. Cancer Res. 48:1494–1498.

Ojala, W. H., Ojala, C. R. and Gleason, W. B. (1995) Antiviral Chemistry and Chemotherapy 6, 25–33.

R. W. Oppenheim. 1991. Cell death during development of the nervous system. Annu. Rev. Neurosci. 14:453–501.

Park, D. S., Farinell,i S. E., and L. A. Greene. 1996a. J. Biol. Chem. 271:8161–8170.

Park, D. S., Stefanis, L., Farinelli, S. E., Yan, C. Y. I., and L. A. Greene. 1996b. J. Biol. Chem. 271:21898–21906.

Park, D. S., Morris, E. J., Greene, L. A., and H. M. Geller. 1997. J. Neurosci. 17:1256–1270.

Ping Dou, Q., An, B., and C. Yu. 1995. Biochem. Biophys. Res. Comm. 214:771–780.

Pinilla, C., et al. (1995) Peptide Science 37, 221–240.

Pittman, R. N., Wang, S., DiBenedetto, A. J. & Mills, J. C. (1993) J. Neurosci. 13, 3669–3680.

Poluha, W., Poluha, D. K., Chang, B., Crosgie, N. E., Schonoff, C. M., Kilpatrick, D. L., and A. H. Ross. 1996. Mol. Cell. Biol. 16:1334–1341.

Pronk, G. J., Ramer, K., Amiri, P., and L. T. Williams. 1996. Science 271:808–810.

Prochiantz, A. & Theodore, L. (1995) Bioessays 17, 39–45.

Ross et al., (1981) Nature, 294, 654–658.

Rukenstein, A., Rydel, R. E. & Greene, L. A. (1991) J. Neurosci. 11, 2552–2563.

Rydel, R. E. & Greene, L. A. (1988) Proc. Natl. Acad. Sci. USA 85, 1257–1261.

Sanchez, Y. and S. J. Elledge. 1995. Bioessays 17:545–548.

Schreiber, M., Baumann, B., Cotten, M., Angel, P., and E. F. Wagner. 1995.EMBO 14:5338–5349.

Shaw, E. (1990) in Advances in Enzymology, ed. Meister, A. (John Wiley & Sons, New York), pp. 271–347.

Shimizu, T., O'Connor, P. M., Kahn, K. W., and Y. Pommier. 1995. Cancer Res. 55:228–231.

Stefanis, L., Park, D. S., Yan, C. Y. I., Farinelli, S. E., Tray, C. M., Shelanski, M. L., and L. A. Greene. 1996. J. Biol. Chem. 271:30663–30671.

Tewari, M. & Dixit, V. M. (1995) J. Biol. Chem. 270, 3255–3260.

Tewari, M., Beidler, D. R. & Dixit, V. M. (1995) J. Biol. Chem. 270, 18738–18741.

Tewari, M., Quan, L. T., O'Rourke, K., Desnoyers, S., Zeng, Z., Beidler, D. R., Poirier, G. G., Salvesen, G. S. & Dixit, V. M. (1995) Cell 81, 801–809.

Thornberry, N. A. (1994) Methods in Enzymology 244, 615–631.

Tomkins, C. E., Edwards, S. N., and A. M. Tolkovsky. 1994. J. Cell Sci. 107:1499–1507.

Troy, C. M., Stefanis, L., Prochiantz, A., Greene, L. A., and M. L. Shelanski. 1996a. Proc. Natl. Acad. Sci. USA 93:5635–5640.

Troy, C. M., Derossi, D., Prochiantz, A., Greene, L. A., and M. L. Shelanski. 1996b. J. Neurosci. 16:253–261.

Troy, C. M. & Shelanski, M. L. (1994) Proc. Natl. Acad. Sci. USA 91, 6384–6387.

Vesely, J., Havlicek, L., Strnad, M., Blow, J. J., Donella-Deanna, A., Pinna L., Letham D. S., Kato J., Detivaud L., Leclerc S., and L. Mieijer. 1994. Eur. J. Biochem. 224:771–786.

Walter et al., (1981) Proc. Natl. Acad. Sci. USA 78, 4882–4886. Wang, L., Miura, M., Bergeron, L., Zhu, H., & Yuan, J. (1994) Cell 78, 739–750.

Wang, L., Miura, M., Bergeron, L., Zhu, H., and J. Yuan. 1994. Cell 78:739–750.

Wang et al., (1982) Proc. Natl. Sci. USA 79, 5322–6326.

Wyllie, A. H., Kerr, J. F. R., and A. R. Currie. 1980. Intern. Rev. Cytol. 68:251–306.

Xia Z., Dickens M., Raingeaud J., Davis R. J., Greenberg M. E. 1996. Science 270:1326–1331.

Yan, S. D., Brett, J., Godman, G., Zou, Y. S., Scott, C. W., Caputo, C., Frappier T., Smith, M. A. et al. (1994) Proc. Natl. Acad. Sci. USA 91, 7787–7791.

Yuan, J., Shahan, S., Ledoux, S., Ellis, H. M. & Horvitz, H. R. (1993) Cell 74, 641–652.

What is claimed is:

1. A method for determining whether a peptide suppresses the rate of cell death in a cell population comprising contacting cells in the cell population with the peptide, and determining whether the rate of cell death in the cell population has been suppressed, thereby determining whether the peptide suppresses the rate of cell death in the cell population, wherein the peptide consists of the structure $(AA_1)_n\text{-Cys-}(AA_2)_m$ and (a) n and m are independently 0, 1, 2, 3, 4 or 5, provided that $2 \geq (n+m) \geq 5$;

(b) if n=1, $(AA_1)_n$=Ala-;

(c) if n=2, $(AA_1)_n$=Gln-Ala-;

(d) if ≦3, $(AA_1)_n$=(Xaa)$_p$-Gln-Ala-, wherein Xaa is any amino acid, and (i) if n=3, p=1, (ii) if n=4, p=2, and (iii) if n=5, p=3;

(e) if m=1, $(AA_2)_m$=-Arg;

(f) if m=2, $(AA_2)_m$=-Arg-Gly; and (g) if m≧3, $(AA_2)_m$=-Arg-Gly-(Xaa)$_q$, wherein (I) if m=3, q=1, (ii) if m=4, q=2, and (iii) if m=5, q=3.

2. The method of claim 1, wherein the cell population is a human cell population.

3. The method of claim 1, wherein the cell population is a neuronal cell population, a cardiac cell population or a hepatic cell population.

4. A method for determining whether a peptide suppresses the rate of cell death in a cell population comprising contacting cells in the cell population with the peptide, and determining whether the rate of cell death in the cell population has been suppressed, thereby determining whether the peptide suppresses the rate of cell death in the cell population, wherein the peptide consists of the structure $(AA_1)_n\text{-Cys-}(AA_2)_m$ and (a) n and m are independently 0, 1, 2, 3, 4 or 5, provided that $2 \leq (n+m) \leq 5$;

(b) if n=1, $(AA_1)_n$=Ala-;

(c) if n=2, $(AA_1)_n$=Gln-Ala-;

(d) if n≧3, $(AA_1)_n$=(Xaa)$_p$-Gln-Ala-, wherein Xaa is any amino acid, and (i) if n=3, p=1, (ii) if n=4, p=2, and (iii) if n=5, p=3;

(e) if m=1, $(AA_2)_m$=-Arg;

(f) if m=2, $(AA_2)_m$=-Arg-Gly; and (g) if m≧3, $(AA_2)_m$=-Arg-Gly-(Xaa)$_q$, wherein (i) if m=3, q=1, (ii) if m=4, q=2, and (iii) if m=5, q=3, and wherein the compound is linked to an agent capable of specifically directing the peptide to a cell.

5. The method of claim 4, wherein the cell population is a human cell population.

6. The method of claim 4, wherein the cell population is a neuronal cell population, a cardiac cell population or a hepatic cell population.

* * * * *